United States Patent [19]

Olson

[11] Patent Number: 4,729,986

[45] Date of Patent: Mar. 8, 1988

[54] FUNGICIDAL TRIAZOLES AND IMIDAZOLES

[75] Inventor: Richard E. Olson, Wilmington, Del.

[73] Assignee: E. I. Du Pont de Nemours and Company, Wilmington, Del.

[21] Appl. No.: 23,747

[22] Filed: Mar. 18, 1987

Related U.S. Application Data

[63] Continuation-in-part of Ser. No. 855,297, Apr. 24, 1986, abandoned.

[51] Int. Cl.$^4$ .................... A01N 55/00; C07F 7/18
[52] U.S. Cl. ..................................... 514/63; 548/510
[58] Field of Search ........................... 548/110; 514/63

[56] References Cited

U.S. PATENT DOCUMENTS

| | | | |
|---|---|---|---|
| 3,692,798 | 9/1972 | Bareza | 260/309 |
| 4,118,461 | 10/1978 | Miller et al. | 424/273 R |
| 4,301,166 | 11/1985 | Regal et al. | 424/269 |
| 4,414,210 | 11/1983 | Miller et al. | 424/245 |
| 4,510,136 | 4/1985 | Moberg | 514/63 |
| 4,530,922 | 7/1985 | Moberg | 514/63 |
| 4,595,406 | 6/1986 | Parry et al. | 71/76 |

FOREIGN PATENT DOCUMENTS

| | | |
|---|---|---|
| 817243 | 1/1975 | Belgium . |
| 867245 | 11/1978 | Belgium . |
| 0003373 | 1/1979 | European Pat. Off. . |
| 0001654 | 6/1979 | European Pat. Off. . |
| 036153 | 9/1981 | European Pat. Off. . |
| 0101288 | 2/1984 | European Pat. Off. . |
| 2610022 | 8/1976 | Fed. Rep. of Germany . |
| 2640823 | 3/1977 | Fed. Rep. of Germany . |
| 2846127 | 4/1980 | Fed. Rep. of Germany . |
| 3121676 | 12/1982 | Fed. Rep. of Germany . |
| 3238006 | 4/1984 | Fed. Rep. of Germany . |
| 7162609 | 8/1971 | Netherlands . |
| 346306 | 7/1972 | U.S.S.R. . |

OTHER PUBLICATIONS

The Reaction of 1,2,4-Triazole-3-tione with Chloroacetonitryle, Valenia Rudnicha et al., Ann. Acad. Geclan., 1975, No. 5, 165-174.

Structure-Activity Relations in Derivatives of 1-(o-nitrophenyl)-and 1-(o-methylsulfurophenyl)ethanol, Alfonso Mugraini et al., Boll. Chim. Farm., 105(8), 595-605 (abstract only).

*Primary Examiner*—Richard L. Raymond

[57] ABSTRACT

Substituted silylmethyl 1,2,4-triazoles and imidazoles also having selected substituents on the heterocyclic ring, agriculturally useful compositions comprising such compounds and the use of such compounds as fungicides.

24 Claims, No Drawings

FUNGICIDAL TRIAZOLES AND IMIDAZOLES

CROSS REFERENCE TO RELATED APPLICATION

This application is a continuation-in-part of my co-pending application U.S. Ser. No. 855,297 filed Apr. 24, 1986, now abandoned.

BACKGROUND OF THE INVENTION

U.S. Pat. No. 4,510,136 issued on Apr. 9, 1985 to W. K. Moberg claims 1,2,4-triazole derivatives of the following formula:

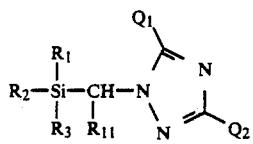

and their use as fungicides. The substitutent groups, $Q_1$ and $Q_2$, are limited to H or $CH_3$.

U.S. Pat. No. 4,530,922 issued on July 23, 1985 to W. K. Moberg discloses fungicidal imidazoles and triazoles containing silicon of the following formula:

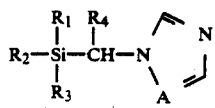

The A group in the ring is limited to CH or N.

U.S. Pat. No. 3,692,798 discloses compounds of the formula:

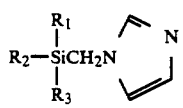

wherein $R_1$, $R_2$ and $R_3$ can be lower alkyl and phenyl. It is stated that these compounds are useful as antimicrobial agents.

U.S.S.R. Pat. No. 346,306 discloses silylmethylazoles of the formula:

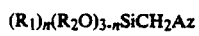

$(R_1)_n(R_2O)_{3-n}SiCH_2Az$ wherein $R_1$ and $R_2$ are alkyl groups, n is 0-3, and Az is a pyrazole, imidazole, or benzimidazole ring, optionally substituted.

European Pat. No. 11,769 teaches that compounds of the general formula:

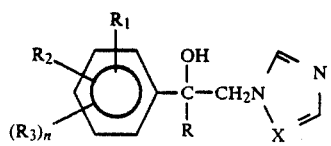

wherein

R is a substituted phenyl, naphthyl or tetrahydronaphthyl ring;

$R_1$ is a substituted phenyl or cycloalkyl ring;

$R_2$ is H, or together with $R_1$ it may form an annelated aryl or alkyl ring;

$R_3$ is halogen, alkyl, alkoxy or haloalkyl;

n is 0, 1, 2 or 3; and

X is CH or N, are useful as antimicrobial agents.

European Pat. No. 15,756 discloses compounds of the formula:

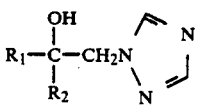

wherein $R_1$ is alkyl, cycloalkyl, or substituted phenyl; and $R_2$ is substituted phenyl or benzyl, and their use as agricultural fungicides.

European Pat. No. 36,153 discloses compounds of the formula:

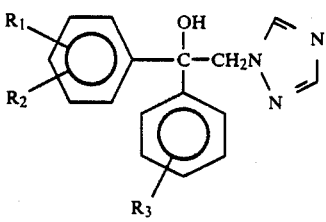

wherein $R_1$, $R_2$ and $R_3$ are H or Cl, provided that at least one of $R_1$ or $R_3$ is Cl, and their use as antimicrobials.

Belgian Pat. No. 867,245 discloses compounds of the formula:

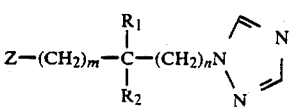

wherein

Z is aryl;

$R_1$ is CN, H, alkyl, cycloalkyl, alkenyl, cycloalkenyl, alkynyl, substituted aryl, or substituted aralkyl;

$R_2$ is H, alkyl, cycloalkyl, alkenyl, cycloalkenyl, alkynyl, substituted aryl, substituted aralkyl, alkoxy, alkenoxy, alkynoxy, OH, substituted aryloxy, or substituted aralkyloxy;

m is 0 or 1; and n is 1 or 2, and their use as agricultural fungicides.

U.S. Pat. No. 4,414,210 discloses compounds of the formula:

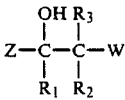

wherein

Z is an aryl or substituted aryl group;

$R_1$, $R_2$, and $R_3$ are independently H, CN, alkyl, cycloalkyl, alkenyl, alkynyl, aryl, substituted aryl, aralkyl, or substituted aralkyl; and W is a 1- or 4-(1,2,4-triazole), and their use as agricultural fungicides.

SUMMARY OF THE INVENTION

This invention pertains to silylmethyl triazoles and imidazoles, having the formula

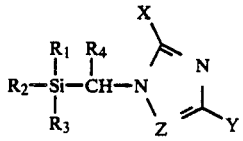

I to compositions containing such triazoles or imidazoles, and to their use as fungicides.

In the formula $R_1$ is

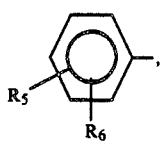

naphthyl, $-CR_7=CHR_8$, or $-C\equiv CR_7$;

$R_2$ and $R_3$ are independently $C_1-C_6$ alkyl, vinyl, $CH_2CR_9=CR_{10}R_{11}$,

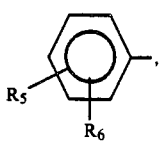

or $OR_{12}$ provided that both $R_2$ and $R_3$ may not be $OR_{12}$;

$R_4$ is H or $CH_3$;

$R_5$ and $R_6$ are independently H, F, Cl, Br, $OCH_3$, $SCH_3$, $OCF_2H$, $OCF_3$, $C_1-C_4$ alkyl, $C_1-C_4$ haloalkyl, phenyl, or halophenyl;

$R_7$ and $R_8$ are independently H, $C_1-C_4$ alkyl; or

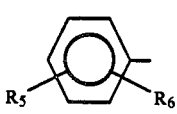

$R_9$, $R_{10}$ and $R_{11}$ are independently H or $CH_3$:

X is H, $C_2-C_4$ alkenyl, ethynyl, F, Cl, Br, I, $NO_2$, SH and its corresponding disulfide, SeH and its corresponding diselenide,

-continued

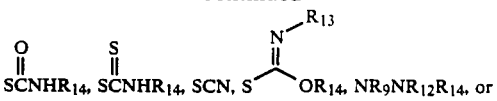

Y is H, F, Cl, Br, I,

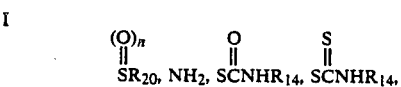

$SSR_{17}$, $CO_2CH_3$, CHO, or SH and its corresponding disulfide;

Z is CH or N;

m is 0 or 1;

n is 0, 1, or 2;

$R_{12}$ is H or $C_1-C_4$ alkyl;

$R_{13}$ is H, $C_1-C_4$ alkyl, allyl, benzyl, $C_1-C_4$ alkylcarbonyl, $C_1-C_4$ haloalkylcarbonyl;

$R_{14}$ and $R_{15}$ are independently H, $C_1-C_4$ alkyl, allyl, benzyl, or phenyl optionally substituted with 1–3 substituents independently selected from halogen, $C_1-C_4$ alkyl, $C_1-C_4$ haloalkyl, $C_1-C_4$ alkoxy, $NO_2$ or $SCH_3$;

$R_{16}$ is H, $C_1-C_8$ alkyl, $C_3-C_8$ cycloalkyl, $C_2-C_8$ alkenyl, $C_4-C_8$ cycloalkenyl, alpha-pinenyl, aralkyl, aralkenyl, or phenyl optionally substituted with 1–3 substituents independently selected from halogen, $C_1-C_4$ alkyl, $C_1-C_4$ haloalkyl, $C_1-C_4$ alkoxy, $NO_2$ or $SCH_3$;

$R_{17}$ is $C_1-C_4$ alkyl, $C_1-C_4$ haloalkyl, allyl, benzyl or phenyl optionally substituted with 1–3 substituents independently selected from halogen, $C_1-C_4$ alkyl, $C_1-C_4$ haloalkyl, $C_1-C_4$ alkoxy, $NO_2$ or $SCH_3$;

$R_{18}$ is $C_1-C_5$ alkyl, $C_1-C_4$ haloalkyl, $CH_2SCN$, $C_2-C_4$ alkenyl, $CHR_9(CHR_{10})_mCN$, $CH_2CO_2R_{14}$, $C_3-C_4$ alkynyl, $CH_2NO_2$, benzyl, $CH_2OCH_3$,

$R_{19}$ is $CH_3$, phenyl, or benzyl;

$R_{20}$ is $C_1-C_4$ alkyl, $CH_2CN$, $CH_2SCN$, or allyl;

$R_{21}$ is $C_2-C_4$ alkyl, $CH_2CN$, or $CH_2SCN$;

provided that: (1) either X or Y must be H, but both X and Y cannot be H simultaneously; and (2) when Z is CH, then Y is H and X is $S(O)_nR_{21}$, $SO_2OH$, I or SH and its corresponding disulfide.

Preferred

Preferred for their high fungicidal activity, or their ease of synthesis, or both, are compounds wherein $R_1$ is 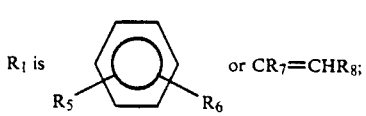 or $CR_7=CHR_8$;

$R_5$ and $R_6$ are independently H, F, Cl, Br, phenyl, or halophenyl;

$R_2$ is $C_1-C_4$ alkyl or

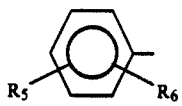

$R_3$ is $C_1$-$C_4$ alkyl, vinyl, allyl, or $OR_{12}$;
$R_4$ is H;
X is F, Cl, I,

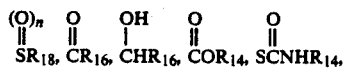

$SSR_{17}$, or SH and its corresponding disulfide; and
Y is H.
More preferred are compounds wherein
$R_3$ is $C_1$-$C_4$ alkyl, allyl, or $OR_{12}$;
$R_5$ and $R_6$ are independently H, F, Cl, Br, phenyl, or halophenyl substituted at the 4-position; and
X is I,

$SSR_{17}$, or SH and its corresponding disulfide.
Most preferred are compounds wherein X is I,

$SSR_{17}$, or SH and its corresponding disulfide.
Specifically preferred for reasons of greatest ease of synthesis or highest fungicidal activity or both are:
1. 1-[bis(4-fluorophenyl)(methyl)silylmethyl]-1H-1,2,4-triazole-5-thiol;
2. 1-[bis(4-fluorophenyl)(methyl)silylmethyl]-5-iodo-1H-1,2,4-triazole;
3. 1-[bis(4-fluorophenyl)(methyl)silylmethyl]-5-(cyanomethylsulfonyl)-1H-1,2,4-triazole; and
4. 1-[bis(4-fluorophenyl)(methyl)silylmethyl]-2-iodo-1H-imidazole.

DETAILED DESCRIPTION OF THE INVENTION

Synthesis

I. Synthesis of 1,5-Disubstituted-1,2,4-Triazoles

The compounds of Formula Ia, in which Y is H, can be prepared from compounds of Formula II by the methods described below.

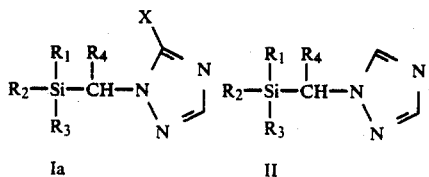

Compounds of Formula II can be prepared by various methods, as disclosed in U.S. Pat. Nos. 4,510,136 and 4,530,922.

A. Metalation and Subsequent Functionalization

The metalation of II with strong bases (Equation 1) provides the 5-metalated triazoles III (R. G. Micetich et al., Heterocycles 1985, 23, 1645-49).

Equation 1

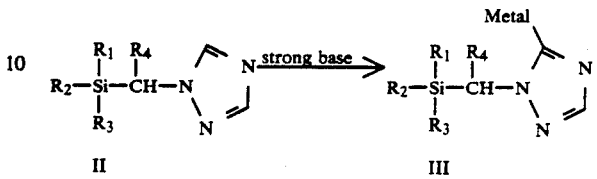

Suitable bases include organoalkali metal compounds, such as n-butyllithium, and alkali metal amides, such as lithium diisopropylamide. Appropriate solvents for the metalation include hydrocarbons such as toluene, and ethereal solvents such as tetrahydrofuran (THF), dimethoxyethane (DME) and diethyl ether. The metalations can be carried out from −80° C. to 60° C. for periods of 1 to 120 minutes, depending on the choice of base, solvent and substrate. Typical conditions involve treatment of a solution of II in THF at −70° C. with n-butyllithium for 15 minutes, which gives III where the metal is lithium. When $R_2$ or $R_3$ is OH, two equivalents of base are required.

Other methods for the preparation of organo-metallic compounds which are known to one skilled in the art are applicable to the preparation of III, and include halogen-metal exchange between halotriazoles and organometallic compounds, reductive metalation of halotriazoles and the reaction of III with anhydrous metal salts. For a review, see J. March. *Advanced Organic Chemistry*, 3rd Edition, J. Wiley and Sons, New York, N.Y., 1985, p. 1169-1170.

The use of organometallic compounds of Formula III in appending a wide variety of functional groups to metalated carbon centers has been reviewed (H. G. Gschwend and H. R. Rodriguez, *Organic Reactions*, Volume 26, W. G. Dauben, Ed., J. Wiley and Sons, New York, N.Y., 1979, p. 1; J. March, op. cit., see Index under Grignard reagents, p. 1314). More specifically, transformations of III to compounds of this invention are discussed below according to the type of bond formed to C-5 of the triazole ring.

Metalation of a 1-substituted imidazole, by analogy to Equation 1 above, yields a 2-metalated imidazole analogous to the compound of Formula III. Subsequent treatment according to the methods described for triazoles provides 1,2-disubstituted imidazoles analogous to the compounds of Formula Ia.

1. Bonds to Carbon

The conversion of compounds of Formula III to compounds of this invention having C-5 carbon bonds is outlined in Scheme I and involves standard transformations known to one skilled in the art. Some examples are given below.

Scheme I

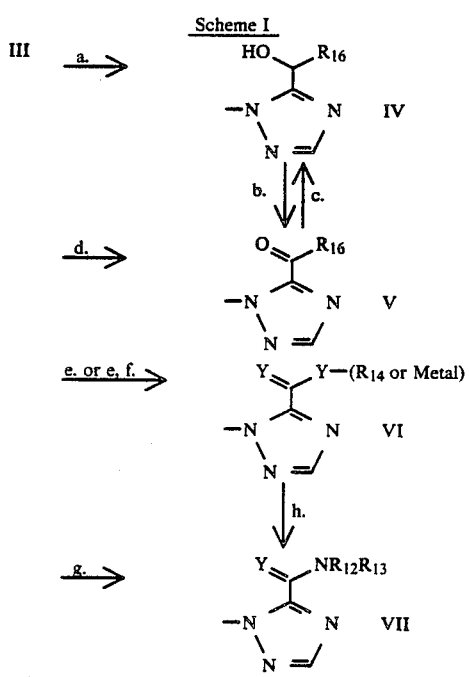

Y = O or S.
a. R₁₆CHO;
b. pyridinium chlorochromate;
c. NaBH₄ or LiAlH₄;
d. R₁₆C(O)N(alkyl)₂;
e. CY₂;
f. R₁₄—halogen or R₁₄—OSO₂Ar;
g. R₁₃NCY or R₁₂R₁₃NCYCl;
h. (CO)₂Cl₂, then HNR₁₂R₁₃, when R₁₄ in VI is H.

The reaction of compounds of Formula III with acid derivatives such as dialkylamides provides acyltriazoles V (S. Ohta et. al., Heterocycles 1985, 23, 1759-64).

Treatment of III with $CO_2$, COS or $CS_2$ provides the metal salts of the 5-triazole carboxylic acids, thioacids and dithioacids. In some cases, the parent carboxylic acids readily decarboxylate. (Micetich, op.cit.). Alkylation of these metal salts with, for example, non-aryl $R_{14}$ iodides in methyl ethyl ketone or THF provides esters, thioesters or dithioesters of Formula VI. These esters are precursors of VI where $R_{14}$ constitutes an aryl group, via exchange reactions of $R_{14}OH$ or $R_{14}SH$ under the influence of basic or acidic catalysis.

The 5-formyltriazoles of Formula V are intermediates for the preparation of other C-5 carbon bond compounds of this invention using methods known to one skilled in the art, as shown in Scheme II. For example, the reaction of 5-formyltriazoles with dibromomethylenetriphenylphosphorane provides dibromoolefins VIII (W=Br) which may be converted to alkynes of Formula IX using n-butyllithium (E. J. Corey et al., Tetrahedron Lett. 1972, 3769).

Scheme II

Scheme II

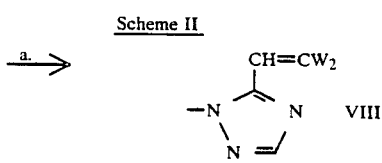

-continued
Scheme II

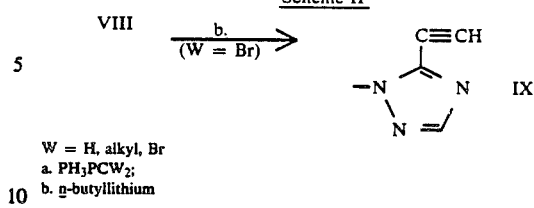

W = H, alkyl, Br
a. PH₃PCW₂;
b. n-butyllithium

2. Bonds to Sulfur or Selenium

The conversion of compounds of Formula III to mercaptan metal salts or mercaptans X (X=SH) can be carried out using standard procedures (see March, op. cit., p. 550). These can be converted to other compounds of this invention having C-5 sulfur bonds following procedures known to one skilled in the art, as shown in Scheme III. For example, disulfides of Formula XIV can be prepared by treatment of thiols X with sulfenyl chlorides or phthalimidosulfides in inert solvents (D. N. Harpp et al., Tetrahedron Lett. 1970, 3551). Sulfenamides of Formula XIII are available by the reaction of disulfides XII with lithium dialkylamides (H. Ikehira et al., Synthesis 1983, 716) and by treatment of sulfenyl halides with amines (R. Lejeune et al., J. Pharm. Belg. 1984, 39, 217).

Scheme III

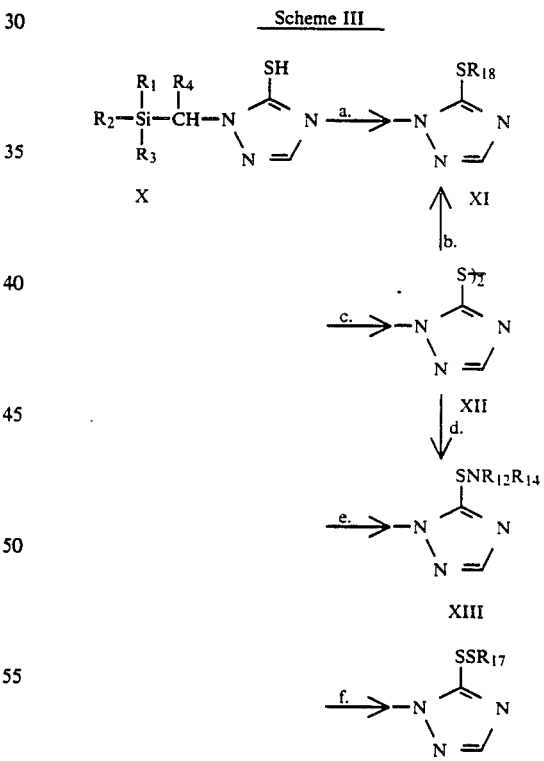

a. R₁₈I; b. R₁₈—Metal; c. Br₂; d. LiNR₁₂R₁₄; e. Cl₂, then HNR₁₂R₁₄; f. R₁₇S—Phthalimido Sulfides of Formula XI can be converted to sulfoxides and sulfones using standard procedures.

The selenides and selenoxides of the present invention can be prepared using methods similar to those employed for the preparation of sulfides of Formula XI and corresponding sulfoxides.

The thiols of Formula X are precursors to other C-5 sulfur substituted compounds of this invention as shown in Scheme IV. For example, treatment of thiols X with cyanogen halides provides thiocyanates of Formula XV (C. Temple and J. A. Montgomery, *Triazoles*, Vol. 37 of *Heterocyclic Compounds*, A. Weissberger and E. C. Taylor, Eds., J. Wiley and Sons, New York, N.Y., 1981, p. 257). Treatment of X with $R_{14}NCY$ (Y=O or S) provides thiocarbamates XVI (ibid.).

Scheme IV

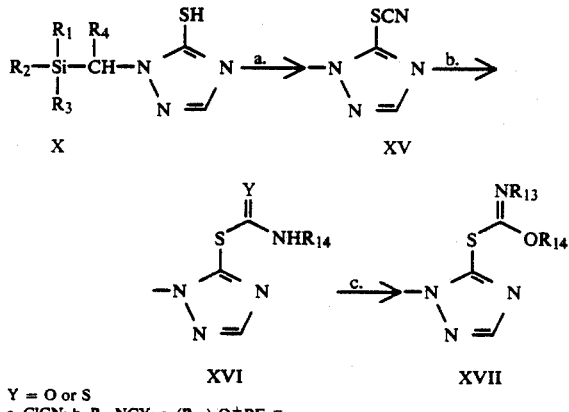

Y = O or S
a. ClCN; b. $R_{14}NCY$; c. $(R_{14})_3O^+BF_4^-$.

3. Bonds to Other Elements

The preparation of 5-halotriazoles of Formula Ia can be carried out using methods known to one skilled in the art (see Gschwend, op. cit., p. 83 and March, op. cit., p. 551). For example, treatment of III, where the metal is lithium, with iodine provides Ia where X is iodine (Equation 2).

Equation 2

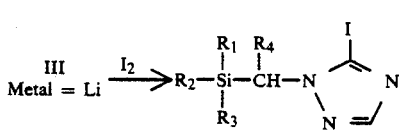

Treatment of III in ethereal solvents such as THF with $R_{15}O(R_{14}O)P(Cl)O$ where $R_{15}$, $R_{14}\neq H$ gives C-5 phosphates. Treatment with iodotrimethylsilane, then water, where $R_{15}$, $R_{14}$ are n-alkyl or benzyl, gives the C-5 phosphonic acids.

Amination of III can be carried out using $CH_3ONHR_{12}$ (March, op. cit., p. 553). Alternatively, III can be reacted with an arenesulfonyl azide, followed by reduction with, e.g., $NaBH_4$ (J. N. Reed and V. Snieckus, *Tetrahedron Lett*. 1983, 24, 3795). The resulting amines can be alkylated or oxidized to compounds where $X=NO_2$ using methods known to one skilled in the art.

B. Other Methods

Compounds of the present invention where $X=NR_9NR_{12}R_{14}$ are available by the reaction of, for example, the 5-bromotriazoles with hydrazines (Temple and Montgomery, *Triazoles*, op. cit., p. 291).

Compounds of Formula II react with sulfenyl halides, such as perchloromethylmercaptan in inert solvents such as methylene chloride, in the presence of triethylamine to give sulfides of Formula XI.

II. Synthesis of 1,3-Disubstituted-1,2,4-Triazoles

The compounds of Formula Ib in which X is H, can be prepared by alkylation of silylmethyl halides XXII or sulfonate esters with metal salts of $Z^1$-substituted triazoles, where $Z^1$ is Y or can be converted to Y using known procedures. Examples of

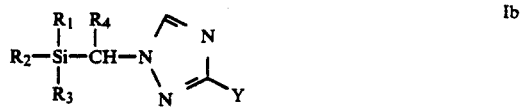

$Z^1$ to Y conversions are given in Section I: Synthesis of 1,5-Disubstituted-1,2,4-Triazoles. It is understood that with this procedure, mixtures of 1,3- and 1,5-disubstituted-1,2,4-triazoles may be produced, from which the desired isomers can be isolated using standard techniques.

A variety of substituted triazoles are available using literature procedures (Temple and Montgomery, *Triazoles*, op. cit., see Index). Alkylation of halomethylsilanes as described in U.S. Pat. Nos. 4,510,136 and 4,530,922 with $Z^1$-substituted triazoles, where $Z^1$ is Y or can be converted to Y using standard procedures, provides silylmethyl-($Z^1$-substituted) triazoles. For example, 1,2,4-triazole-3-thiol can be alkylated with trityl chloride (T. W. Greene, *Protective Groups in Organic Synthesis*, J. Wiley and Sons, New York, N.Y., 1981, p. 201). The potassium salt of the resulting tritylthiotriazole can be allowed to react with halomethylsilanes and the product deprotected (Greene, loc. cit.) (Equation 3). The 3-mercaptotriazole XX can be converted to other compounds of Formula Ib having C-3 sulfur bonds.

Equation 3

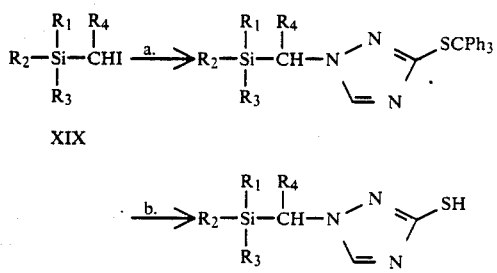

a. 3-Triphenylmethylthio-1,2,4-triazole, potassium salt;
b. Protic or Lewis acid.

Similarly, alkylation of halomethylsilanes with a metal (e.g., potassium) salt of 3-nitro-1,2,4-triazole provides the analogous 3-nitro-1-silylmethyltriazole, which can be reduced to give the 3-amino compound.

Similar reactions are possible for other values of $Z^1(X, Y)$, and in many cases no protection-deprotection is required. Depending on $Z^1(X, Y)$ and the reaction conditions used, varying amounts of 5-substituted 1-silylmethyltriazoles may also be prepared. The 3- and 5-substituted triazoles may be separated by standard methods, such as chromotography.

In the following examples, temperatures are reported in degrees Celsius. Abbreviations for nuclear magnetic resonance (nmr) spectra are s=singlet, d=doublet, t=triplet, q=quartet, m=multiplet, br=broad; peak positions are reported as parts per million downfield from tetramethylsilane. Hexanes refers to a mixture of

EXAMPLE 1

Metalation of 1-Silylmethyl-1,2,4-triazoles

Preparation of
bis(4-Fluorophenyl)methyl[5-(3-phenylpropen-1-ol)-1H-1,2,4-triazol-1-ylmethyl]silane To a solution of 3.2 g (0.010 mol) of bis(4-fluorophenyl)methyl(1H-1,2,4-triazol-1-ylmethyl)silane in 15 mL of THF cooled to −78° was added 6.5 mL (0.010 mol) of 1.6M n-butyllithium in hexane over 3 minutes. After 15 minutes, 1.3 g (0.010 mol) of cinnamaldehyde was added and the solution was stirred 30 minutes. Saturated aqueous NH$_4$Cl was added and the mixture was extracted with 1:1 ether/hexanes. The organic extracts were washed with brine, dried over MgSO$_4$ and evaporated. The crude product was flash chromatographed using 10% ether/methylene chloride to give 3.5 g of the title compound as a viscous glass: ir (neat) 3400–3000 (br), 1900, 1585, 1490, 1100, 965 cm$^{-1}$; nmr (CDCl$_3$) δ 0.7 (3H, s), 3.5 (1H, br s), 4.2 (2H, s), 5.4 (1H, d, J=6 Hz), 6.2 (1H, dd, J=16, 6 Hz), 6.6 (1H, d, J=16 Hz), 7.0 (4H, m), 7.3 (5H, s), 7.4 (4H, m), 7.8 (1H, s).

EXAMPLE 2

Preparation of
bis(4-Fluorophenyl)methyl(5-formyl-1H-1,2,4-triazol-1-ylmethyl)silane Bis(4-fluorophenyl)methyl(1H-1,2,4-triazol-1-ylmethyl)silane (1.3 g, 0.004 mol) was lithiated as described in Example 1 using 3.7 mL (0.0044 mol) of 1.2M n-butyllithium in 10 mL of THF. DMF (1.2 mL, 0.016 mol) was added and the solution was allowed to warm to 0° C. After 1 hour, the reaction mixture was diluted with 1:1 ether/hexanes, washed with 7% aqueous NaHCO$_3$ and brine, dried over Na$_2$SO$_4$ and evaporated. Flash chromatography using 10% ether/methylene chloride gave 1.1 g of the title compound as a clear oil: n$^D$ 1.5612; ir (neat) 2840, 1705, 1587, 1499, 1228, 1160, 1106, 821 cm$^{-1}$; nmr (CDCl$_3$) δ, 0.7 (3H, s), 4.7 (2H, s), 7.0 (4H, t), 7.4 (4H, m), 7.9 (1H, s), 9.8 (1H, s).

EXAMPLE 3

Oxidation of Alcohols IV

Preparation of
bis(4-Fluorophenyl)methyl[5-(2,5-dimethylbenzoyl)-1H-1,2,4-triazol-1-ylmethyl]silane To a mixture of 1.5 g (0.0033 mol) of bis(4-fluorophenyl)methyl[5-(2,5-dimethylphenyl)hydroxymethyl-1H-1,2,4-triazol-1-ylmethyl]silane and 2.2 g of Celite in 20 mL of CH$_2$Cl$_2$ was added 1.1 g (0.005 mol) of pyridinium chlorochromate. The mixture was stirred overnight, filtered and evaporated, leaving a dark residue. Flash chromatography (CH$_2$Cl$_2$) gave 1.2 g of the title compound as a yellow oil: ir (neat) 2940, 1665, 1595, 1505, 1240, 1170, 1118, 950, 830 cm$^{-1}$; nmr (CDCl$_3$) δ 0.8 (3H, s), 2.30 (6H, s), 4.9 (2H, s), 7.0–7.3 (7H, m), 7.5 (4H, t), 7.9 (1H, s).

EXAMPLE 4

Preparation of
bis(4-Fluorophenyl)methyl(5-methylthiocarbonyl-1H-1,2,4-triazol-1-ylmethyl)silane To a −78° C. solution of 0.016 mol of lithio[bis(4-fluorophenyl)methyl(1H-1,2,4-triazol-1-ylmethyl)silane, prepared in 75 mL of THF as described in Example 1, was added 1 mL of liquid carbonyl sulfide. The solution was allowed to warm to 0° over 1 hour, and 1.0 mL (0.016 mol) of iodomethane was added. The reaction mixture was stored at 25° for 3 days, then poured into saturated aqueous NH$_4$Cl. The aqueous layer was extracted twice with ether, and the combined organic layers were dried (MgSO$_4$) and evaporated to give 5.2 g of the title compound as a yellow oil: n$^D$ 1.5694; ir (neat) 1710 (w), 1663; nmr (CDCl$_3$) δ 0.7 (3H, s), 2.3 (3H, s), 4.6 (2H, s), 7.0 (4H, m), 7.4 (4H, m), 7.8 (1H, s).

EXAMPLE 5

Preparation of
bis(4-Fluorophenyl)methyl(5-iodo-1H-1,2,4-triazol-1-ylmethyl)silane A solution of 3.14 g (0.010 mol) of bis(4-fluorophenyl)methyl(1H-1,2,4-triazol-1-ylmethyl)silane in 15 ml of THF was lithiated as described in Example 1, using 7.1 ml (0.011 mol) of 1.55M n-butyllithium in hexane. To this solution was added 1.4 g (0.011 mol) of iodine. The reaction mixture was allowed to warm to 0°, stirred 3 hours, poured into 1:1 ether/hexanes, washed with 7% aqueous NaHCO$_3$ and brine, dried over Na$_2$SO$_4$, filtered and evaporated. The crude product was flash chromatographed (5% ether/methylene chloride) to give 0.83 g of the title compound as a white solid: m.p. 102°–104°; nmr (CDCl$_3$) δ 0.7 (3H, s), 4.2 (2H, s), 7.1 (4H, m), 7.5 (4H, m), 7.8 (1H, s).

EXAMPLE 6

Preparation of
bis(4-Fluorophenyl)methyl(5-methylthio-1H-1,2,4-triazol-1-ylmethyl)silane A solution of 1.5 g (0.005 mol) of bis(4-fluorophenyl)methyl(1H-1,2,4-triazol-1-ylmethyl)silane in 10 mL of THF was treated with n-butyllithium as described in Example 1. To this solution was added 0.63 mL (0.007 mol) of dimethyl disulfide. The reaction mixture was allowed to warm to 0°, stirred 30 minutes, then poured into 1:1 ether/hexanes, washed with 7% aqueous NaHCO$_3$ and brine, dried over Na$_2$SO$_4$, filtered and evaporated. The crude product was flash chromatographed (5% ether/methylene chloride) to give 1.4 g of the title compound as a clear oil: n$^D$ 1.5750; ir (neat) 3030 (w), 2935 (w), 1587, 1496, 1230, 1160, 1106, 1035, 822 cm$^{-1}$; nmr (CDCl$_3$) δ 0.7 (3H, s), 2.6 (3H, s), 4.0 (2H, s), 7.1 (4H, m), 7.5 (4H, m), 7.8 (1H, s).

EXAMPLE 7

PREPARATION of
bis(4-Fluorophenyl)methyl(5-mercapto-1H-1,2,4-triazol-1-ylmethyl)silane To a solution of 134 g (0.424 mol) of bis(4-fluorophenyl)methyl(1H-1,2,4-triazol-1-ylmethyl)silane in 850 mL of THF cooled to −70° was added 265 mL (0.424 mol) of 1.6M n-butyllithium in hexane over 15 minutes, keeping the temperature below −60°. After 20 minutes, 13.6 g (0.424 mol) of sulfur was added all at once. The reaction mixture was allowed to warm to 0° over 1 hour, during which time the sulfur was taken up, then the reaction mixture was brought to pH 1 with 475 mL of 1N HCl. The aqueous layer was extracted with ether and the combined organic layers were washed with brine, dried over Na$_2$SO$_4$ and evaporated to a light orange oil. This was taken up in 150 mL of hot 1:9 benzene/cyclohexane. Cooling, seeding with crystals produced by ether trituration, and filtration gave 104 g of the title compound as ivory crystals: m.p. 97°–99°; ir (nujol) 3030 (br), 1578, 1222, 1150, 1098, 951, 813 cm$^{-1}$; nmr (CDCl$_3$) δ 0.7 (3H, s), 4.2 (2H, s), 7.0 (4H, t), 7.5 (4H, m), 7.6 (1H, s), 12.0 (1H, br s).

The filtrate was diluted with cyclohexane and allowed to stand at 25°. A second crop of 15 g of less pure material was collected.

EXAMPLE 8

Preparation of bis(4-Fluorophenyl)methyl[5-(thiocyanatomethylthio)-1H-1,2,4-triazol-1-ylmethyl]silane A −78° solution of 0.010 mol of lithio-[bis(4-fluorophenyl)methyl(1H-1,2,4-triazol-1-ylmethyl)silane] in 15 mL of THF, prepared as described in Example 1, was treated with 0.32 g (0.010 mol) of sulfur, allowed to warm to 25° over 1 hour, then cooled to −78° and treated with 0.86 mL (0.011 mol) of chloromethylthiocyanate. The reaction mixture was allowed to warm to 25° C. and was stirred 3 hours, then poured into 1:1 ether/hexanes and 7% aqueous NaHCO$_3$. The aqueous layer was extracted with 1:1 ether/hexanes and the combined organic layers were washed with brine, dried over Na$_2$SO$_4$ and evaporated. Flash chromatography using 2–20% ether/methylene chloride gave 2.7 g of the title compound as an oil: ir (neat) 3010, 2155, 1590, 1499, 1230, 1163, 1109, 1040, 825 cm$^{-1}$; nmr (CDCl$_3$) δ 0.7 (3H, s), 4.0 (2H, s), 4.6 (2H, s), 7.1 (4H, t), 7.5 (4H, m), 7.9 (1H, s).

EXAMPLE 9

Preparation of bis(4-Fluorophenyl)methyl(5-mercapto-1H-1,2,4-triazol-1-ylmethyl)silane, disulfide To a solution of 3.5 g (0.010 mol) of bis(4-fluorophenyl)methyl(5-mercapto-1H-1,2,4-triazol-1-ylmethyl)silane and 1.0 mL (0.012 mol) of pyridine in 20 mL of methylene chloride cooled to 5° C. was added a solution of 0.25 mL (0.005 mol) of bromine in 10 mL of methylene chloride over 5 minutes, causing the reaction temperature to rise to 12°. The solution was stirred at 25° for 30 minutes, diluted with ether, washed with 7% aqueous NaHCO$_3$ (foaming) and brine, and evaporated. Flash chromatography using 20% ether/methylene chloride gave 2.4 g of the title compound as a viscous oil: ir (neat) 3420 (br), 1590, 1500, 1390, 1235, 1165, 1110, 1012, 825, 680 cm$^{-1}$; nmr (CDCl$_3$) δ 0.7 (3H, s), 4.2 (2H, s), 7.1 (4H, t), 7.4 (4H, m), 7.8 (1H, s); mass spectrum: highest m/e 347.

EXAMPLE 10

Preparation of bis(4-Fluorophenyl)methyl[5-(1,2-dithiapentyl)-1H-1,2,4-triazol-1-ylmethyl]silane To a solution of 1.4 g (0.004 mol) of bis(4-fluorophenyl)methyl(5-mercapto-1H-1,2,4-triazol-1-ylmethyl)silane in 10 mL of chloroform at 25° was added 1.1 g (0.005 mol) of propylthiophthalimide. The mixture was stirred two hours, filtered, and evaporated. The residue was flash chromatographed using 0–10% ether/methylene chloride to give 1.5 g of the title disulfide as a thick oil: ir (neat) 2950, 1585, 1495, 1230, 1160, 1104, 820 cm$^{-1}$; nmr (CDCl$_3$) δ 0.7 (3H, s), 1.0 (3H, t), 1.7 (2H, m), 2.8 (2H, t), 4.2 (2H, s), 7.1 (4H, m), 7.5 (4H, m), 7.8 (1H, s).

EXAMPLE 11

Preparation of bis(4-Fluorophenyl)methyl(5-methylsulfinyl-1H-1,2,4-triazol-1-ylmethyl)silane To a solution of 1.8 g (0.005 mol) of bis(4-fluorophenyl)methyl(5-methylthio-1H-1,2,4-triazol-1-ylmethyl)silane in 15 mL of methylene chloride cooled to 0° C. was added 1.1 g (0.005 mol) of m-chloroperbenzoic acid (80%). The reaction temperature rose to 10°. The reaction mixture was stirred at 25° for 3 hours, then diluted with methylene chloride, washed with 7% aqueous NaHCO$_3$ and brine, dried over Na$_2$SO$_4$ and evaporated to give 2.1 g of the title compound as an oil, pure except for traces of solvent and starting material: n$_D$ 1.5717; ir (neat) 3020, 1590, 1500, 1232, 1164, 1110, 1070, 825 cm$^{-1}$; nmr (CDCl$_3$) δ 0.7 (3H, s), 2.8 (3H, s), 4.6 (2H, ABq), 7.1 (4H, m), 7.5 (4H, m), 7.9 (1H, s).

EXAMPLE 12

Preparation of bis(4-Fluorophenyl)methyl(5-methylsulfonyl-1H-1,2,4-triazol-1-ylmethyl)silane To a solution of 2.7 g (0.0074 mol) of bis(4-fluorophenyl)methyl(5-methylthio-1H-1,2,4-triazol-1-ylmethyl)silane in 50 mL of methylene chloride cooled to 0° was added 3.2 g (0.015 mol) of m-chloroperbenzoic acid (80%). The reaction mixture was allowed to warm to 25° and after 2 hours, was diluted with methylene chloride, washed with 3 portions of 7% aqueous NaHCO$_3$ and brine, dried over MgSO$_4$ and evaporated. Flash chromatography (2% ether/methylene chloride) gave 2.6 g of the title compound as a colorless oil: n$_D$ 1.5595; ir (neat) 3025, 1590, 1500, 1328 (br), 1232, 1164, 1145, 1108, 957, 825, 764 cm$^{-1}$; nmr (CDCl$_3$) δ 0.74 (3H, s), 3.1 (3H, s), 4.6 (2H, s), 7.1 (4H, t), 7.5 (4H, m), 7.8 (1H, s).

EXAMPLE 13

Preparation of bis(4-Fluorophenyl)methyl[5-(N-phenylcarbamothio)-1H-1,2,4-triazol-1-ylmethyl]silane To a solution of 3.5 g (0.010 mol) of bis(4-fluorophenyl)methyl(5-mercapto-1H-1,2,4-triazol-1-ylmethyl)silane and a catalytic amount of 4-dimethylaminopyridine in 10 mL of methylene chloride at 25° was added 1.3 mL (0.012 mol) of phenyl isocyanate over 5 minutes, with ice bath cooling. The mixture was stirred 2 hours at 25°, then diluted with ether, washed with 7% aqueous NaHCO$_3$ and brine, dried over Na$_2$SO$_4$ and evaporated. Flash chromatography (methylene chloride) gave 4.1 g of the title compound as ivory crystals: m.p. 126°–128°; ir (nujol) 3450 (br), 1742, 1588, 1405, 1235, 1106, 826 cm$^{-1}$; nmr (CDCl$_3$) δ 0.8 (3H, s), 4.2 (2H, s), 7.0–7.7 (13H, m), 8.5 (1H, s), 12.4 (1H, br s).

EXAMPLE 14

Preparation of
bis(4-Fluorophenyl)methyl(5-trichloromethylthio-1H-1,2,4-triazol-1-ylmethyl)silane To a solution of 4.0 g (0.013 mol) of bis(4-fluorophenyl)methyl(1H-1,2,4-triazol-1-ylmethyl)silane and 2.0 mL (0.014 mol) of triethylamine in 50 mL of methylene chloride at 6° was added 1.4 mL (0.013 mol) of perchloromethylmercaptan over 2 minutes. The reaction temperature rose 6°. The dark solution was stirred at 25° for 2 hours, then diluted with methylene chloride, washed with water and brine, and evaporated to give 3.6 g of the title compound as an oil: ir (neat) 3100, 3020, 2960, 1590, 1500; nmr (CDCl$_3$) δ 0.7 (3H, s), 4.4 (2H, s), 7.1 (4H, t), 7.5 (4H, dd), 8.1 (1H, s); mass spectrum: m/e 464.

EXAMPLE 15

Preparation of
bis(4-Fluorophenyl)methyl(5-bromo-1H-1,2,4-triazol-1-ylmethyl)silane A mixture of 1.5 g (0.0050 mol) of bis(4-fluorophenyl)(methyl)(1H-1,2,4-triazol-1-ylmethyl)silane, 0.98 g (0.0055 mol) of N-bromosuccinimide and ~1 mg of azobisisobutyltronitrile in 10 mL of CCl$_4$ was warmed to 60°, then illuminated with a high intensity lamp (Roxter Model 5900) for 20 minutes. The mixture was cooled, filtered, and evaporated, and the residue was flash chromatographed (10% ether/methylene chloride) to give 1.7 g of the title compound as an oil: ir (neat) 3030, 2960, 1590, 1498, 1479, 1339, 1265, 1231, 1162, 1108, 1033, 825, 789, 733 cm$^{-1}$. nmr (CDCl$_3$) δ0.7 (s, 9H), 4.2 (s, 2H), 7.1 (t, 4H), 7.5 (m, 4H), 7.8 (s, 1H).

The compounds of Formula I set forth in the following table can be prepared using the methods described hereinabove.

In the tables, Ph is phenyl, and substituted phenyl groups are abbreviated, e.g., 4-F-Ph is 4-fluorophenyl, 2,6-MeO$_2$-Ph is 2,6-dimethoxyphenyl and 4-(4-F-Ph)-Ph is 4-(4-fluorophenyl)phenyl. The substituent "-SS-" for X denotes the disulfide dimer of the corresponding mercaptans; "-SeSe-" denotes the analogous diselenides.

TABLE I

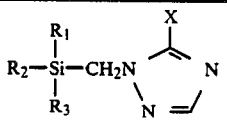

| Cmpd. No. | R$_1$ | R$_2$ | R$_3$ | X | |
|---|---|---|---|---|---|
| 1. | 4-F—Ph | 4-F—Ph | Me | vinyl | oil[46] |
|  | 4-F—Ph | 4-F—Ph | Me | allyl |  |
|  | 4-F—Ph | 4-F—Ph | Me | 2-propenyl |  |
|  | 4-F—Ph | 4-F—Ph | Me | 1-butenyl |  |
|  | 4-F—Ph | 4-F—Ph | Me | ethynyl |  |
|  | 4-F—Ph | 4-F—Ph | Me | F |  |
| 2. | 4-F—Ph | 4-F—Ph | Me | Cl | $n^D$ 1.5595 |
| 3. | 4-F—Ph | 4-F—Ph | Me | Br | oil[1] |
| 4. | 4-F—Ph | 4-F—Ph | Me | I | m.p. 102–104°[2] |
|  | 4-F—Ph | 4-F—Ph | Me | NO$_2$ |  |
| 5. | 4-F—Ph | 4-F—Ph | Me | NH$_2$ | m.p. 151–153° |
|  | 4-F—Ph | 4-F—Ph | Me | MeNH |  |
|  | 4-F—Ph | 4-F—Ph | Me | n-BuNH |  |
|  | 4-F—Ph | 4-F—Ph | Me | i-PrNH |  |
|  | 4-F—Ph | 4-F—Ph | Me | CH$_2$=CHCH$_2$NH |  |
|  | 4-F—Ph | 4-F—Ph | Me | PhCH$_2$NH |  |
|  | 4-F—Ph | 4-F—Ph | Me | Me$_2$N |  |
| 6. | 4-F—Ph | 4-F—Ph | Me | SH | m.p. 97–99° |
| 7. | 4-F—Ph | 4-F—Ph | Me | —SS— | oil[3] |
| 8. | 4-F—Ph | 4-F—Ph | Me | SMe | $n^D$ 1.5750 |
| 9. | 4-F—Ph | 4-F—Ph | Me | S(O)Me | $n^D$ 1.5717 |
| 10. | 4-F—Ph | 4-F—Ph | Me | SO$_2$Me | $n^D$ 1.5595 |
|  | 4-F—Ph | 4-F—Ph | Me | SCF$_2$H |  |
|  | 4-F—Ph | 4-F—Ph | Me | S(O)CF$_2$H |  |
|  | 4-F—Ph | 4-F—Ph | Me | SO$_2$CF$_2$H |  |
| 11. | 4-F—Ph | 4-F—Ph | Me | SCCl$_3$ | oil[19] |
|  | 4-F—Ph | 4-F—Ph | Me | S(O)CCl$_3$ |  |
|  | 4-F—Ph | 4-F—Ph | Me | SO$_2$CCl$_3$ |  |
|  | 4-F—Ph | 4-F—Ph | Me | SEt |  |
|  | 4-F—Ph | 4-F—Ph | Me | S(O)Et |  |
|  | 4-F—Ph | 4-F—Ph | Me | SO$_2$Et |  |
|  | 4-F—Ph | 4-F—Ph | Me | SCF$_2$CF$_2$H |  |
|  | 4-F—Ph | 4-F—Ph | Me | S(O)CF$_2$CF$_2$H |  |
|  | 4-F—Ph | 4-F—Ph | Me | SO$_2$CF$_2$CF$_2$H |  |
|  | 4-F—Ph | 4-F—Ph | Me | SCH$_2$CF$_3$ |  |
|  | 4-F—Ph | 4-F—Ph | Me | S(O)CH$_2$CF$_3$ |  |
|  | 4-F—Ph | 4-F—Ph | Me | SO$_2$CH$_2$CF$_3$ |  |
|  | 4-F—Ph | 4-F—Ph | Me | SCH$_2$CH$_2$F |  |
|  | 4-F—Ph | 4-F—Ph | Me | S(O)CH$_2$CH$_2$F |  |
|  | 4-F—Ph | 4-F—Ph | Me | SO$_2$CH$_2$CH$_2$F |  |
|  | 4-F—Ph | 4-F—Ph | Me | SCH$_2$CH$_2$CH$_2$CH$_2$Br |  |
| 12. | 4-F—Ph | 4-F—Ph | Me | S—n-Pr | $n^D$ 1.5637 |
| 13. | 4-F—Ph | 4-F—Ph | Me | S(O)—n-Pr | $n^D$ 1.5477 |

TABLE I-continued $$R_2-\underset{\underset{R_3}{|}}{\overset{\overset{R_1}{|}}{Si}}-CH_2N\underset{N=\!\!\!/}{\overset{X}{\underset{|}{\diagdown}}}$$

| Cmpd. No. | $R_1$ | $R_2$ | $R_3$ | X | |
|---|---|---|---|---|---|
| 14. | 4-F—Ph | 4-F—Ph | Me | $SO_2$—n-Pr | $n^D$ 1.5518 |
| | 4-F—Ph | 4-F—Ph | Me | $SCH_2CHMe_2$ | |
| | 4-F—Ph | 4-F—Ph | Me | $S(O)CH_2CHMe_2$ | |
| | 4-F—Ph | 4-F—Ph | Me | $SO_2CH_2CHMe_2$ | |
| 15. | 4-F—Ph | 4-F—Ph | Me | $SCH_2CH_2CHMe_2$ | $n^D$ 1.5528 |
| 16. | 4-F—Ph | 4-F—Ph | Me | $S(O)CH_2CH_2CHMe_2$ | $n^D$ 1.5467 |
| 17. | 4-F—Ph | 4-F—Ph | Me | $SO_2CH_2CH_2CHMe_2$ | $n^D$ 1.5281 |
| 18. | 4-F—Ph | 4-F—Ph | Me | $SCH_2CH=CH_2$ | oil[4] |
| | 4-F—Ph | 4-F—Ph | Me | $S(O)CH_2CH=CH_2$ | |
| 19. | 4-F—Ph | 4-F—Ph | Me | $SO_2CH_2CH=CH_2$ | oil[5] |
| 20. | 4-F—Ph | 4-F—Ph | Me | $SCH_2SCN$ | oil[6] |
| 21. | 4-F—Ph | 4-F—Ph | Me | $S(O)CH_2SCN$ | m.p. 109–112° |
| 22. | 4-F—Ph | 4-F—Ph | Me | $SO_2CH_2SCN$ | m.p. 73–76° |
| | 4-F—Ph | 4-F—Ph | Me | $SCH=CH_2$ | |
| | 4-F—Ph | 4-F—Ph | Me | $S(O)CH=CH_2$ | |
| | 4-F—Ph | 4-F—Ph | Me | $SO_2CH=CH_2$ | |
| | 4-F—Ph | 4-F—Ph | Me | $SCH=CHCH_2CH_3$ | |
| | 4-F—Ph | 4-F—Ph | Me | $S(O)CH=CHCH_2CH_3$ | |
| | 4-F—Ph | 4-F—Ph | Me | $SO_2CH=CHCH_2CH_3$ | |
| | 4-F—Ph | 4-F—Ph | Me | $SCH=CMe_2$ | |
| | 4-F—Ph | 4-F—Ph | Me | $S(O)CH=CMe_2$ | |
| | 4-F—Ph | 4-F—Ph | Me | $SO_2CH=CMe_2$ | |
| 23. | 4-F—Ph | 4-F—Ph | Me | $SCH(Me)CN$ | oil[44] |
| 24. | 4-F—Ph | 4-F—Ph | Me | $SCH_2CN$ | oil[7] |
| 25. | 4-F—Ph | 4-F—Ph | Me | $S(O)CH_2CN$ | oil[8] |
| 26. | 4-F—Ph | 4-F—Ph | Me | $SO_2CH_2CN$ | oil[9] |
| 27. | 4-F—Ph | 4-F—Ph | Me | $SCH_2COMe$ | oil[37] |
| 28. | 4-F—Ph | 4-F—Ph | Me | $SO_2CH_2COMe$ | oil[42] |
| 29. | 4-F—Ph | 4-F—Ph | Me | $SCH_2COCH_2CO_2Et$ | oil[43] |
| 30. | 4-F—Ph | 4-F—Ph | Me | $SCH_2CO_2H$ | oil[36] |
| | 4-F—Ph | 4-F—Ph | Me | $S(O)CH_2CO_2H$ | |
| | 4-F—Ph | 4-F—Ph | Me | $SO_2CH_2CO_2H$ | |
| 31. | 4-F—Ph | 4-F—Ph | Me | $SCH_2CO_2Me$ | oil[10] |
| 32. | 4-F—Ph | 4-F—Ph | Me | $S(O)CH_2CO_2Me$ | m.p. 86–89° |
| 33. | 4-F—Ph | 4-F—Ph | Me | $SO_2CH_2CO_2Me$ | semi-solid[11] |
| | 4-F—Ph | 4-F—Ph | Me | $SCH_2CO_2$—n-Pr | |
| | 4-F—Ph | 4-F—Ph | Me | $S(O)CH_2CO_2$—n-Pr | |
| | 4-F—Ph | 4-F—Ph | Me | $SO_2CH_2CO_2$—n-Pr | |
| | 4-F—Ph | 4-F—Ph | Me | $SCH_2CO_2$—t-Bu | |
| | 4-F—Ph | 4-F—Ph | Me | $S(O)CH_2CO_2$—t-Bu | |
| | 4-F—Ph | 4-F—Ph | Me | $SO_2CH_2CO_2$—t-Bu | |
| | 4-F—Ph | 4-F—Ph | Me | $SCH_2CO_2CH_2CH=CH_2$ | |
| | 4-F—Ph | 4-F—Ph | Me | $S(O)CH_2CO_2CH_2Ph$ | |
| | 4-F—Ph | 4-F—Ph | Me | $SO_2CH_2CO_2Ph$ | |
| | 4-F—Ph | 4-F—Ph | Me | $S(O)CH_2CO_2$—3,5-$Cl_2$—Ph | |
| 34. | 4-F—Ph | 4-F—Ph | Me | $SCH_2C\equiv CH$ | oil[12] |
| | 4-F—Ph | 4-F—Ph | Me | $S(O)CH_2C\equiv CH$ | |
| | 4-F—Ph | 4-F—Ph | Me | $SO_2CH_2C\equiv CH$ | |
| | 4-F—Ph | 4-F—Ph | Me | $SCH_2C\equiv CMe$ | |
| | 4-F—Ph | 4-F—Ph | Me | $SC\equiv CCH_2CH_3$ | |
| | 4-F—Ph | 4-F—Ph | Me | $SO_2CH_2CH_3C\equiv CH$ | |
| | 4-F—Ph | 4-F—Ph | Me | $SCH_2NO_2$ | |
| | 4-F—Ph | 4-F—Ph | Me | $S(O)CH_2NO_2$ | |
| | 4-F—Ph | 4-F—Ph | Me | $SO_2CH_2NO_2$ | |
| 35. | 4-F—Ph | 4-F—Ph | Me | $SCH_2Ph$ | oil[13] |
| 36. | 4-F—Ph | 4-F—Ph | Me | $S(O)CH_2Ph$ | oil[30] |
| 37. | 4-F—Ph | 4-F—Ph | Me | $SO_2CH_2Ph$ | oil[31] |
| 38. | 4-F—Ph | 4-F—Ph | Me | $SCH_2OCH_3$ | oil[14] |
| | 4-F—Ph | 4-F—Ph | Me | $S(O)CH_2OCH_3$ | |
| | 4-F—Ph | 4-F—Ph | Me | $SO_2CH_2OCH_3$ | |
| 39. | 4-F—Ph | 4-F—Ph | Me | SSMe | oil[15] |
| | 4-F—Ph | 4-F—Ph | Me | SSEt | |
| 40. | 4-F—Ph | 4-F—Ph | Me | SS—n-Pr | oil[16] |
| 41. | 4-F—Ph | 4-F—Ph | Me | SS—i-Pr | oil[17] |
| | 4-F—Ph | 4-F—Ph | Me | SS—n-Bu | |
| 42. | 4-F—Ph | 4-F—Ph | Me | $SSCH_2Ph$ | oil[32] |
| 43. | 4-F—Ph | 4-F—Ph | Me | $SSCCl_3$ | m.p. 98°(d) |
| 44. | 4-F—Ph | 4-F—Ph | Me | SSPh | oil[18] |
| | 4-F—Ph | 4-F—Ph | Me | SS—4-F—Ph | |
| | 4-F—Ph | 4-F—Ph | Me | SS—3-$CF_3$—Ph | |
| | 4-F—Ph | 4-F—Ph | Me | SS—4-MeO—Ph | |
| | 4-F—Ph | 4-F—Ph | Me | $SNH_2$ | |
| | 4-F—Ph | 4-F—Ph | Me | SNHMe | |

TABLE I-continued $$R_2-\underset{\underset{R_3}{|}}{\overset{\underset{|}{R_1}}{Si}}-CH_2N\underset{N=}{\overset{\overset{X}{|}}{\diagdown}}\diagup$$

| Cmpd. No. | R₁ | R₂ | R₃ | X | |
|---|---|---|---|---|---|
| | 4-F—Ph | 4-F—Ph | Me | SNHCH₂CH=CH₂ | |
| | 4-F—Ph | 4-F—Ph | Me | SNHPh | |
| | 4-F—Ph | 4-F—Ph | Me | SNMe₂ | |
| | 4-F—Ph | 4-F—Ph | Me | SN(i-Bu)Ph | |
| | 4-F—Ph | 4-F—Ph | Me | SN(CH₂Ph)Me | |
| | 4-F—Ph | 4-F—Ph | Me | SNEt₂ | |
| | 4-F—Ph | 4-F—Ph | Me | SNH—2-Me—Ph | |
| | 4-F—Ph | 4-F—Ph | Me | SeH | |
| | 4-F—Ph | 4-F—Ph | Me | —SeSe— | |
| | 4-F—Ph | 4-F—Ph | Me | SeMe | |
| | 4-F—Ph | 4-F—Ph | Me | Se(O)Me | |
| | 4-F—Ph | 4-F—Ph | Me | SePh | |
| | 4-F—Ph | 4-F—Ph | Me | Se(O)Ph | |
| | 4-F—Ph | 4-F—Ph | Me | SCN | |
| | 4-F—Ph | 4-F—Ph | Me | NHNH₂ | |
| | 4-F—Ph | 4-F—Ph | Me | NMeNMe₂ | |
| | 4-F—Ph | 4-F—Ph | Me | NHNHPh | |
| | 4-F—Ph | 4-F—Ph | Me | NMeNHMe | |
| 45. | 4-F—Ph | 4-F—Ph | Me | NHCOCF₃ | m.p. 139–142° |
| 46. | 4-F—Ph | 4-F—Ph | Me | NH₃⁺Cl⁻ | m.p. 240–245° |
| | 4-F—Ph | 4-F—Ph | Me | $\underset{SCNH_2}{\overset{\overset{O}{\|}}{}}$ | |
| 47. | 4-F—Ph | 4-F—Ph | Me | $\underset{SCNHMe}{\overset{\overset{O}{\|}}{}}$ | oil[20] |
| | 4-F—Ph | 4-F—Ph | Me | $\underset{SCNHEt}{\overset{\overset{O}{\|}}{}}$ | |
| | 4-F—Ph | 4-F—Ph | Me | $\underset{SCNH-n\text{-}Pr}{\overset{\overset{O}{\|}}{}}$ | |
| 48. | 4-F—Ph | 4-F—Ph | Me | $\underset{SCNH-n\text{-}Bu}{\overset{\overset{O}{\|}}{}}$ | oil[21] |
| 49. | 4-F—Ph | 4-F—Ph | Me | $\underset{SCNH-i\text{-}Pr}{\overset{\overset{O}{\|}}{}}$ | oil[34] |
| | 4-F—Ph | 4-F—Ph | Me | $\underset{SCNH-t\text{-}Bu}{\overset{\overset{O}{\|}}{}}$ | |
| | 4-F—Ph | 4-F—Ph | Me | $\underset{SCNH-s\text{-}Bu}{\overset{\overset{O}{\|}}{}}$ | |
| | 4-F—Ph | 4-F—Ph | Me | $\underset{SCNHCH_2Ph}{\overset{\overset{O}{\|}}{}}$ | |
| 50. | 4-F—Ph | 4-F—Ph | Me | $\underset{SCNHCH_2CH=CH_2}{\overset{\overset{O}{\|}}{}}$ | oil[33] |
| 51. | 4-F—Ph | 4-F—Ph | Me | $\underset{SCNHPh}{\overset{\overset{O}{\|}}{}}$ | m.p. 126–128° |
| 52. | 4-F—Ph | 4-F—Ph | Me | $\underset{SCNH-4\text{-}Cl-Ph}{\overset{\overset{O}{\|}}{}}$ | m.p. 121–124° |
| 53. | 4-F—Ph | 4-F—Ph | Me | $\underset{SCNH-4\text{-}F-Ph}{\overset{\overset{O}{\|}}{}}$ | m.p. 94–97° |

TABLE I-continued

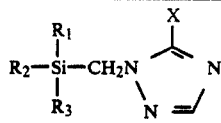

| Cmpd. No. | R₁ | R₂ | R₃ | X | |
|---|---|---|---|---|---|
| 54. | 4-F—Ph | 4-F—Ph | Me | $\underset{\|\|}{\overset{O}{SCNH-3-Me-Ph}}$ | m.p. 121-124° |
| | 4-F—Ph | 4-F—Ph | Me | $\underset{\|\|}{\overset{O}{SCNH-2-CF_3-Ph}}$ | |
| | 4-F—Ph | 4-F—Ph | Me | $\underset{\|\|}{\overset{O}{SCNH-4-MeO-Ph}}$ | |
| | 4-F—Ph | 4-F—Ph | Me | $\underset{\|\|}{\overset{O}{SCNH-4-Me-Ph}}$ | |
| | 4-F—Ph | 4-F—Ph | Me | $\underset{\|\|}{\overset{O}{SCNH-3,5-Cl_2-Ph}}$ | |
| | 4-F—Ph | 4-F—Ph | Me | $\underset{\|\|}{\overset{O}{SCNH-3-MeO-Ph}}$ | |
| | 4-F—Ph | 4-F—Ph | Me | $\underset{\|\|}{\overset{O}{SCNH-4-NO_2-Ph}}$ | |
| | 4-F—Ph | 4-F—Ph | Me | $\underset{\|\|}{\overset{O}{SCNH-2,6-Cl_2-Ph}}$ | |
| | 4-F—Ph | 4-F—Ph | Me | $\underset{\|\|}{\overset{O}{SCNH-4-CN-Ph}}$ | |
| | 4-F—Ph | 4-F—Ph | Me | $\underset{\|\|}{\overset{O}{SCNH-4-MeO-Ph}}$ | |
| | 4-F—Ph | 4-F—Ph | Me | $\underset{\|\|}{\overset{O}{SCNH-2,4-Me_2-Ph}}$ | |
| | 4-F—Ph | 4-F—Ph | Me | $\underset{\|\|}{\overset{S}{SCNH_2}}$ | |
| | 4-F—Ph | 4-F—Ph | Me | $\underset{\|\|}{\overset{S}{SCNHMe}}$ | |
| | 4-F—Ph | 4-F—Ph | Me | $\underset{\|\|}{\overset{S}{SCNHCH_2CH=CH_2}}$ | |
| | 4-F—Ph | 4-F—Ph | Me | $\underset{\|\|}{\overset{S}{SCNHCH_2Ph}}$ | |
| | 4-F—Ph | 4-F—Ph | Me | $\underset{\|\|}{\overset{S}{SCNH-\underline{n}-Bu}}$ | |
| | 4-F—Ph | 4-F—Ph | Me | $\underset{\|\|}{\overset{S}{SCNHPh}}$ | |
| | 4-F—Ph | 4-F—Ph | Me | $\underset{\|\|}{\overset{S}{SCNH-4-Cl-Ph}}$ | |
| | 4-F—Ph | 4-F—Ph | Me | MeN=C(OMe)S | |
| | 4-F—Ph | 4-F—Ph | Me | PhN=C(OMe)S | |
| | 4-F—Ph | 4-F—Ph | Me | n-BuN=C(OEt)S | |
| 55. | 4-F—Ph | 4-F—Ph | Me | CH₂OH | m.p. 112-116° |

TABLE I-continued

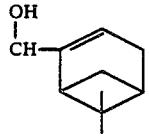

| Cmpd. No. | R₁ | R₂ | R₃ | X | |
|---|---|---|---|---|---|
| 56. | 4-F—Ph | 4-F—Ph | Me | CH(OH)Me | oil[22] |
|  | 4-F—Ph | 4-F—Ph | Me | CH(OH)Et |  |
| 57. | 4-F—Ph | 4-F—Ph | Me | CH(OH)—i-Pr | m.p. 110-113° |
| 58. | 4-F—Ph | 4-F—Ph | Me | CH(OH)Ph | semi-solid[23] |
| 59. | 4-F—Ph | 4-F—Ph | Me | CH(OH)vinyl | m.p. 78-80° |
| 60. | 4-F—Ph | 4-F—Ph | Me | CH(OH)CH=CHCH₃ | m.p. 95-101° |
| 61. | 4-F—Ph | 4-F—Ph | Me | CH(OH)CH=CHPh | glass[24] |
|  | 4-F—Ph | 4-F—Ph | Me | CH(OH)—2-propenyl |  |
| 62. | 4-F—Ph | 4-F—Ph | Me | CH(OH)—C(CH₃)=CHPh | oil[25] |
| 63. | 4-F—Ph | 4-F—Ph | Me | CH(OH)—2,5-MeO₂—Ph | m.p. 120-121° |
| 64. | 4-F—Ph | 4-F—Ph | Me | CH(OH)—2,5-Me₂—Ph | m.p. 140-142° |
|  | 4-F—Ph | 4-F—Ph | Me | CH(OH)—4-Cl—Ph |  |
|  | 4-F—Ph | 4-F—Ph | Me | CH(OH)CH₂Ph |  |
| 65. | 4-F—Ph | 4-F—Ph | Me | (OH-substituted bicyclic group) | m.p. 60-62° |
| 66. | 4-F—Ph | 4-F—Ph | Me | CH(OH)C(=CH₂)CHMe₂ | m.p. 82-85° |
| 67. | 4-F—Ph | 4-F—Ph | Me | CHO | n_D 1.5612 |
| 68. | 4-F—Ph | 4-F—Ph | Me | COMe | oil[26] |
|  | 4-F—Ph | 4-F—Ph | Me | COEt |  |
|  | 4-F—Ph | 4-F—Ph | Me | CO—i-Pr |  |
|  | 4-F—Ph | 4-F—Ph | Me | COCH=CH₂ |  |
|  | 4-F—Ph | 4-F—Ph | Me | COCH=CHCH₃ |  |
|  | 4-F—Ph | 4-F—Ph | Me | COCH=CHPh |  |
| 69. | 4-F—Ph | 4-F—Ph | Me | COC(CH₃)=CHPh | oil[38] |
|  | 4-F—Ph | 4-F—Ph | Me | COC(CH₃)=CH₂ |  |
| 70. | 4-F—Ph | 4-F—Ph | Me | COPh | oil[35] |
| 71. | 4-F—Ph | 4-F—Ph | Me | CO—2,5-MeO₂—Ph | oil[39] |
| 72. | 4-F—Ph | 4-F—Ph | Me | CO—2,5-Me₂—Ph | oil[27] |
|  | 4-F—Ph | 4-F—Ph | Me | CO—4-Cl—Ph |  |
|  | 4-F—Ph | 4-F—Ph | Me | COCH₂Ph |  |
| 73. | 4-F—Ph | 4-F—Ph | Me | COC(=CH₂)CHMe₂ | oil[45] |
| 74. | 4-F—Ph | 4-F—Ph | Me | (CO-substituted bicyclic group) | oil[40] |
| 75. | 4-F—Ph | 4-F—Ph | Me | COC(Me)=CHCH(Me)CH₂CH=CH₂ | oil[41] |
|  | 4-F—Ph | 4-F—Ph | Me | PO(OH)₂ |  |
|  | 4-F—Ph | 4-F—Ph | Me | PO(OMe)₂ |  |
| 76. | 4-F—Ph | 4-F—Ph | Me | PO(OEt)₂ | oil[28] |
|  | 4-F—Ph | 4-F—Ph | Me | PO(OCH₂Ph)₂ |  |
|  | 4-F—Ph | 4-F—Ph | Me | PO(O—i-Pr)₂ |  |
|  | 4-F—Ph | 4-F—Ph | Me | CONH₂ |  |
|  | 4-F—Ph | 4-F—Ph | Me | CONHMe |  |
|  | 4-F—Ph | 4-F—Ph | Me | CONMe₂ |  |
|  | 4-F—Ph | 4-F—Ph | Me | CONHCH₂CH=CH₂ |  |
|  | 4-F—Ph | 4-F—Ph | Me | CONH—n-Bu |  |
|  | 4-F—Ph | 4-F—Ph | Me | CONH—i-Pr |  |
|  | 4-F—Ph | 4-F—Ph | Me | CSNH₂ |  |
|  | 4-F—Ph | 4-F—Ph | Me | CSNMe₂ |  |
|  | 4-F—Ph | 4-F—Ph | Me | CSNHMe |  |
|  | 4-F—Ph | 4-F—Ph | Me | CSNH—i-Pr |  |
|  | 4-F—Ph | 4-F—Ph | Me | CSNHCH₂CH=CH₂ |  |
|  | 4-F—Ph | 4-F—Ph | Me | CSNH—n-Bu |  |
|  | 4-F—Ph | 4-F—Ph | Me | CSNHCH₂Ph |  |
| 77. | 4-F—Ph | 4-F—Ph | Me | CO₂H | m.p. 84-100° |
|  | 4-F—Ph | 4-F—Ph | Me | CO₂Li |  |
| 78. | 4-F—Ph | 4-F—Ph | Me | CO₂Me | oil[29] |
|  | 4-F—Ph | 4-F—Ph | Me | CO₂Et |  |
|  | 4-F—Ph | 4-F—Ph | Me | CO₂CH₂CH=CH₂ |  |
|  | 4-F—Ph | 4-F—Ph | Me | CO₂—t-Bu |  |
|  | 4-F—Ph | 4-F—Ph | Me | CO₂CH₂Ph |  |
|  | 4-F—Ph | 4-F—Ph | Me | CO₂Ph |  |

TABLE I-continued $$R_2-\underset{\underset{R_3}{|}}{\overset{\overset{R_1}{|}}{Si}}-CH_2N\underset{N=}{\overset{\overset{X}{|}}{\underset{|}{C}}}N$$

| Cmpd. No. | $R_1$ | $R_2$ | $R_3$ | X | |
|---|---|---|---|---|---|
| | 4-F—Ph | 4-F—Ph | Me | $CO_2$—4-Me—Ph | |
| | 4-F—Ph | 4-F—Ph | Me | $CS_2H$ | |
| 79. | 4-F—Ph | 4-F—Ph | Me | $CS_2Me$ | m.p. 57–60° C. |
| | 4-F—Ph | 4-F—Ph | Me | $CS_2Et$ | |
| 80. | 4-F—Ph | 4-F—Ph | Me | $CS_2CH_2CH=CH_2$ | $n_D$ 1.6001 |
| | 4-F—Ph | 4-F—Ph | Me | $CS_2CH_2Ph$ | |
| 81. | 4-F—Ph | 4-F—Ph | Me | COSMe | $n_D$ 1.5694 |
| 82. | 4-F—Ph | 4-F—Ph | Me | COSEt | $n_D$ 1.5658 |
| | 4-F—Ph | 4-F—Ph | Me | $COSCH_2Ph$ | |
| 83. | 4-F—Ph | 4-F—Ph | Me | $COSCH_2CH=CH_2$ | $n_D$ 1.5690 |
| | 4-F—Ph | 4-F—Ph | Me | COS—i-Pr | |
| 84. | 4-F—Ph | Ph | Me | SH | m.p. 114–115° |
| 85. | Ph | Ph | Me | SH | m.p. 157–158° |
| 86. | 4-Cl—Ph | 4-Cl—Ph | Me | SH | m.p. 157–158° |
| 87. | 4-Cl—Ph | Ph | Me | SH | m.p. 138–141° |
| | 4-F—Ph | 2-F—Ph | Me | SH | |
| | 4-F—Ph | 2,4-$F_2$—Ph | Me | SH | |
| | 4-F—Ph | 4-F—Ph | vinyl | SH | |
| | 4-F—Ph | 4-F—Ph | allyl | SH | |
| 88. | 4-Ph—Ph | Me | Me | SH | m.p. 153–157° |
| | 4-Ph—Ph | vinyl | vinyl | SH | |
| | 4-F—Ph | 4-F—Ph | OH | SH | |
| | 4-F—Ph | 4-F—Ph | O—t-Bu | SH | |
| | 4-F—Ph | 4-F—Ph | Et | SH | |
| | 2,4-$Cl_2$—Ph | Me | Me | SH | |
| | 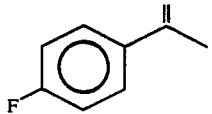 | 4-F—Ph | Me | SH | |
| | 4-F—Ph | Ph | Me | —SS— | |
| | Ph | Ph | Me | —SS— | |
| | 4-Cl—Ph | 4-Cl—Ph | Me | —SS— | |
| | 4-Cl—Ph | Ph | Me | —SS— | |
| | 4-F—Ph | 2-F—Ph | Me | —SS— | |
| | 4-F—Ph | 2,4-$F_2$—Ph | Me | —SS— | |
| | 4-F—Ph | 4-F—Ph | vinyl | —SS— | |
| | 4-F—Ph | 4-F—Ph | allyl | —SS— | |
| | 4-Ph—Ph | Me | Me | —SS— | |
| | 4-Ph—Ph | vinyl | vinyl | —SS— | |
| | 4-F—Ph | 4-F—Ph | OH | —SS— | |
| | 4-F—Ph | 4-F—Ph | O—t-Bu | —SS— | |
| | 4-F—Ph | 4-F—Ph | Et | —SS— | |
| | 2,4-$Cl_2$—Ph | Me | Me | —SS— | |
| | 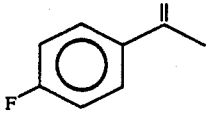 | 4-F—Ph | Me | —SS— | |
| | 4-F—Ph | Ph | Me | SMe | |
| | Ph | Ph | Me | SMe | |
| | 4-Cl—Ph | 4-Cl—Ph | Me | SMe | |
| | 4-Cl—Ph | Ph | Me | SMe | |
| | 4-F—Ph | 2-F—Ph | Me | SMe | |
| | 4-F—Ph | 2,4-$F_2$—Ph | Me | SMe | |
| | 4-F—Ph | 4-F—Ph | vinyl | SMe | |
| | 4-F—Ph | 4-F—Ph | allyl | SMe | |
| | 4-Ph—Ph | Me | Me | SMe | |
| | 4-Ph—Ph | vinyl | vinyl | SMe | |
| | 4-F—Ph | 4-F—Ph | OH | SMe | |
| | 4-F—Ph | 4-F—Ph | O—t-Bu | SMe | |
| | 4-F—Ph | 4-F—Ph | Et | SMe | |
| | 2,4-$Cl_2$—Ph | Me | Me | SMe | |

TABLE I-continued

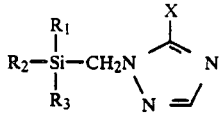

| Cmpd. No. | R₁ | R₂ | R₃ | X |
|---|---|---|---|---|
| | 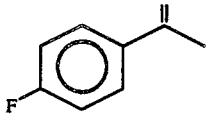 | 4-F—Ph | Me | SMe |
| | 4-F—Ph | Ph | Me | S(O)Me |
| | Ph | Ph | Me | S(O)Me |
| | 4-Cl—Ph | 4-Cl—Ph | Me | S(O)Me |
| | 4-Cl—Ph | Ph | Me | S(O)Me |
| | 4-F—Ph | 2-F—Ph | Me | S(O)Me |
| | 4-F—Ph | 2,4-F₂—Ph | Me | S(O)Me |
| | 4-F—Ph | 4-F—Ph | vinyl | S(O)Me |
| | 4-F—Ph | 4-F—Ph | allyl | S(O)Me |
| | 4-Ph—Ph | Me | Me | S(O)Me |
| | 4-Ph—Ph | vinyl | vinyl | S(O)Me |
| | 4-F—Ph | 4-F—Ph | OH | S(O)Me |
| | 4-F—Ph | 4-F—Ph | O—t-Bu | S(O)Me |
| | 4-F—Ph | 4-F—Ph | Et | S(O)Me |
| | 2,4-Cl₂—Ph | Me | Me | S(O)Me |
| | 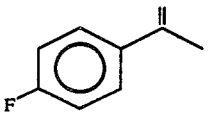 | 4-F—Ph | Me | S(O)Me |
| | 4-F—Ph | Ph | Me | SO₂Me |
| | Ph | Ph | Me | SO₂Me |
| | 4-Cl—Ph | 4-Cl—Ph | Me | SO₂Me |
| | 4-Cl—Ph | Ph | Me | SO₂Me |
| | 4-F—Ph | 2-F—Ph | Me | SO₂Me |
| | 4-F—Ph | 2,4-F₂—Ph | Me | SO₂Me |
| | 4-F—Ph | 4-F—Ph | vinyl | SO₂Me |
| | 4-F—Ph | 4-F—Ph | allyl | SO₂Me |
| | 4-Ph—Ph | Me | Me | SO₂Me |
| | 4-Ph—Ph | vinyl | vinyl | SO₂Me |
| | 4-F—Ph | 4-F—Ph | OH | SO₂Me |
| | 4-F—Ph | 4-F—Ph | O—t-Bu | SO₂Me |
| | 4-F—Ph | 4-F—Ph | Et | SO₂Me |
| | 2,4-Cl₂—Ph | Me | Me | SO₂Me |
| | 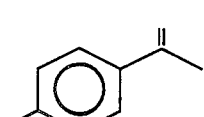 | 4-F—Ph | Me | SO₂Me |
| | 4-F—Ph | Ph | Me | SSMe |
| | Ph | Ph | Me | SSMe |
| | 4-Cl—Ph | 4-Cl—Ph | Me | SSMe |
| | 4-Cl—Ph | Ph | Me | SSMe |
| | 4-F—Ph | 2-F—Ph | Me | SSMe |
| | 4-F—Ph | 2,4-F₂—Ph | Me | SSMe |
| | 4-F—Ph | 4-F—Ph | vinyl | SSMe |
| | 4-F—Ph | 4-F—Ph | allyl | SSMe |
| | 4-Ph—Ph | Me | Me | SSMe |
| | 4-Ph—Ph | vinyl | vinyl | SSMe |
| | 4-F—Ph | 4-F—Ph | OH | SSMe |
| | 4-F—Ph | 4-F—Ph | O—t-Bu | SSMe |
| | 4-F—Ph | 4-F—Ph | Et | SSMe |
| | 2,4-Cl₂—Ph | Me | Me | SSMe |
| | 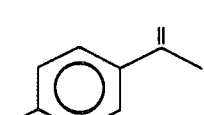 | 4-F—Ph | Me | SSMe |

TABLE I-continued $$\begin{array}{c} R_1 \\ | \\ R_2-Si-CH_2N \\ | \\ R_3 \end{array} \begin{array}{c} X \\ \| \\ \diagdown \diagup \diagdown N \\ | \quad \| \\ N \diagup \end{array}$$

| Cmpd. No. | R₁ | R₂ | R₃ | X |
|---|---|---|---|---|
| | 4-F—Ph | Ph | Me | $\overset{O}{\underset{\|}{SCNHMe}}$ |
| | Ph | Ph | Me | $\overset{O}{\underset{\|}{SCNHMe}}$ |
| | 4-Cl—Ph | 4-Cl—Ph | Me | $\overset{O}{\underset{\|}{SCNHMe}}$ |
| | 4-Cl—Ph | Ph | Me | $\overset{O}{\underset{\|}{SCNHMe}}$ |
| | 4-F—Ph | 2-F—Ph | Me | $\overset{O}{\underset{\|}{SCNHMe}}$ |
| | 4-F—Ph | 2,4-F₂—Ph | Me | $\overset{O}{\underset{\|}{SCNHMe}}$ |
| | 4-F—Ph | 4-F—Ph | vinyl | $\overset{O}{\underset{\|}{SCNHMe}}$ |
| | 4-F—Ph | 4-F—Ph | allyl | $\overset{O}{\underset{\|}{SCNHMe}}$ |
| | 4-Ph—Ph | Me | Me | $\overset{O}{\underset{\|}{SCNHMe}}$ |
| | 4-Ph—Ph | vinyl | vinyl | $\overset{O}{\underset{\|}{SCNHMe}}$ |
| | 4-F—Ph | 4-F—Ph | OH | $\overset{O}{\underset{\|}{SCNHMe}}$ |
| | 4-F—Ph | 4-F—Ph | O—t-Bu | $\overset{O}{\underset{\|}{SCNHMe}}$ |
| | 4-F—Ph | 4-F—Ph | Et | $\overset{O}{\underset{\|}{SCNHMe}}$ |
| | 2,4-Cl₂—Ph | Me | Me | $\overset{O}{\underset{\|}{SCNHMe}}$ |
| | 4-F-C₆H₄-C(=CH₂)- | 4-F—Ph | Me | $\overset{O}{\underset{\|}{SCNHMe}}$ |
| | 4-F—Ph | Ph | Me | $\overset{O}{\underset{\|}{SCNH-\underline{n}\text{-Bu}}}$ |
| | Ph | Ph | Me | $\overset{O}{\underset{\|}{SCNH-\underline{n}\text{-Bu}}}$ |
| | 4-Cl—Ph | 4-Cl—Ph | Me | $\overset{O}{\underset{\|}{SCNH-\underline{n}\text{-Bu}}}$ |

TABLE I-continued $$\text{R}_2-\underset{\underset{\text{R}_3}{|}}{\overset{\overset{\text{R}_1}{|}}{\text{Si}}}-\text{CH}_2\text{N}\diagup\overset{\text{X}}{\underset{\text{N}}{\diagdown}}\diagdown_{\text{N}}$$

| Cmpd. No. | R₁ | R₂ | R₃ | X |
|---|---|---|---|---|
| | 4-Cl—Ph | Ph | Me | $\underset{\text{SCNH}-\underline{n}\text{-Bu}}{\overset{\overset{\text{O}}{\|}}{}}$ |
| | 4-F—Ph | 2-F—Ph | Me | $\underset{\text{SCNH}-\underline{n}\text{-Bu}}{\overset{\overset{\text{O}}{\|}}{}}$ |
| | 4-F—Ph | 2,4-F₂—Ph | Me | $\underset{\text{SCNH}-\underline{n}\text{-Bu}}{\overset{\overset{\text{O}}{\|}}{}}$ |
| | 4-F—Ph | 4-F—Ph | vinyl | $\underset{\text{SCNH}-\underline{n}\text{-Bu}}{\overset{\overset{\text{O}}{\|}}{}}$ |
| | 4-F—Ph | 4-F—Ph | allyl | $\underset{\text{SCNH}-\underline{n}\text{-Bu}}{\overset{\overset{\text{O}}{\|}}{}}$ |
| | 4-Ph—Ph | Me | Me | $\underset{\text{SCNH}-\underline{n}\text{-Bu}}{\overset{\overset{\text{O}}{\|}}{}}$ |
| | 4-Ph—Ph | vinyl | vinyl | $\underset{\text{SCNH}-\underline{n}\text{-Bu}}{\overset{\overset{\text{O}}{\|}}{}}$ |
| | 4-F—Ph | 4-F—Ph | OH | $\underset{\text{SCNH}-\underline{n}\text{-Bu}}{\overset{\overset{\text{O}}{\|}}{}}$ |
| | 4-F—Ph | 4-F—Ph | O—t-Bu | $\underset{\text{SCNH}-\underline{n}\text{-Bu}}{\overset{\overset{\text{O}}{\|}}{}}$ |
| | 4-F—Ph | 4-F—Ph | Et | $\underset{\text{SCNH}-\underline{n}\text{-Bu}}{\overset{\overset{\text{O}}{\|}}{}}$ |
| | 2,4-Cl₂—Ph | Me | Me | $\underset{\text{SCNH}-\underline{n}\text{-Bu}}{\overset{\overset{\text{O}}{\|}}{}}$ |
| | 4-F-C₆H₄-C(=CH₂)- | 4-F—Ph | Me | $\underset{\text{SCNH}-\underline{n}\text{-Bu}}{\overset{\overset{\text{O}}{\|}}{}}$ |
| | 4-F—Ph | Ph | Me | $\underset{\text{SCNHPh}}{\overset{\overset{\text{O}}{\|}}{}}$ |
| | Ph | Ph | Me | $\underset{\text{SCNHPh}}{\overset{\overset{\text{O}}{\|}}{}}$ |
| | 4-Cl—Ph | 4-Cl—Ph | Me | $\underset{\text{SCNHPh}}{\overset{\overset{\text{O}}{\|}}{}}$ |
| | 4-Cl—Ph | Ph | Me | $\underset{\text{SCNHPh}}{\overset{\overset{\text{O}}{\|}}{}}$ |
| | 4-F—Ph | 2-F—Ph | Me | $\underset{\text{SCNHPh}}{\overset{\overset{\text{O}}{\|}}{}}$ |

TABLE I-continued $$R_2-\underset{\underset{R_3}{|}}{\overset{\overset{R_1}{|}}{Si}}-CH_2N\underset{N=\!\!\!\!/}{\overset{\overset{X}{|}}{\diagdown}}N$$

| Cmpd. No. | R₁ | R₂ | R₃ | X |
|---|---|---|---|---|
| | 4-F—Ph | 2,4-F₂—Ph | Me | $\underset{SCNHPh}{\overset{O}{\|}}$ |
| | 4-F—Ph | 4-F—Ph | vinyl | $\underset{SCNHPh}{\overset{O}{\|}}$ |
| | 4-F—Ph | 4-F—Ph | allyl | $\underset{SCNHPh}{\overset{O}{\|}}$ |
| | 4-Ph—Ph | Me | Me | $\underset{SCNHPh}{\overset{O}{\|}}$ |
| | 4-Ph—Ph | vinyl | vinyl | $\underset{SCNHPh}{\overset{O}{\|}}$ |
| | 4-F—Ph | 4-F—Ph | OH | $\underset{SCNHPh}{\overset{O}{\|}}$ |
| | 4-F—Ph | 4-F—Ph | O—t-Bu | $\underset{SCNHPh}{\overset{O}{\|}}$ |
| | 4-F—Ph | 4-F—Ph | Et | $\underset{SCNHPh}{\overset{O}{\|}}$ |
| | 2,4-Cl₂—Ph | Me | Me | $\underset{SCNHPh}{\overset{O}{\|}}$ |
| | 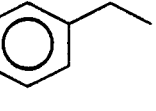 | 4-F—Ph | Me | $\underset{SCNHPh}{\overset{O}{\|}}$ |
| | 4-F—Ph | Ph | Me | F |
| | Ph | Ph | Me | F |
| | 4-Cl—Ph | 4-Cl—Ph | Me | F |
| | 4-Cl—Ph | Ph | Me | F |
| | 4-F—Ph | 2-F—Ph | Me | F |
| | 4-F—Ph | 2,4-F₂—Ph | Me | F |
| | 4-F—Ph | 4-F—Ph | vinyl | F |
| | 4-F—Ph | 4-F—Ph | allyl | F |
| | 4-Ph—Ph | Me | Me | F |
| | 4-Ph—Ph | vinyl | vinyl | F |
| | 4-F—Ph | 4-F—Ph | OH | F |
| | 4-F—Ph | 4-F—Ph | O—t-Bu | F |
| | 4-F—Ph | 4-F—Ph | Et | F |
| | 2,4-Cl₂—Ph | Me | Me | F |
| | 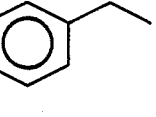 | 4-F—Ph | Me | F |
| | 4-F—Ph | Ph | Me | Cl |
| | Ph | Ph | Me | Cl |
| | 4-Cl—Ph | 4-Cl—Ph | Me | Cl |
| | 4-Cl—Ph | Ph | Me | Cl |
| | 4-F—Ph | 2-F—Ph | Me | Cl |
| | 4-F—Ph | 2,4-F₂—Ph | Me | Cl |
| | 4-F—Ph | 4-F—Ph | vinyl | Cl |
| | 4-F—Ph | 4-F—Ph | allyl | Cl |
| | 4-Ph—Ph | Me | Me | Cl |
| | 4-Ph—Ph | vinyl | vinyl | Cl |

TABLE I-continued

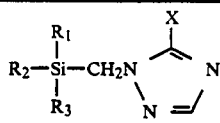

| Cmpd. No. | R₁ | R₂ | R₃ | X |
|---|---|---|---|---|
| | 4-F—Ph | 4-F—Ph | OH | Cl |
| | 4-F—Ph | 4-F—Ph | O—t-Bu | Cl |
| | 4-F—Ph | 4-F—Ph | Et | Cl |
| | 2,4-Cl₂—Ph | Me | Me | Cl |
| | 1-(4-F-Ph)ethenyl | 4-F—Ph | Me | Cl |
| | 4-F—Ph | Ph | Me | CHO |
| | Ph | Ph | Me | CHO |
| | 4-Cl—Ph | 4-Cl—Ph | Me | CHO |
| | 4-Cl—Ph | Ph | Me | CHO |
| | 4-F—Ph | 2-F—Ph | Me | CHO |
| | 4-F—Ph | 2,4-F₂—Ph | Me | CHO |
| | 4-F—Ph | 4-F—Ph | vinyl | CHO |
| | 4-F—Ph | 4-F—Ph | allyl | CHO |
| | 4-Ph—Ph | Me | Me | CHO |
| | 4-Ph—Ph | vinyl | vinyl | CHO |
| | 4-F—Ph | 4-F—Ph | OH | CHO |
| | 4-F—Ph | 4-F—Ph | O—t-Bu | CHO |
| | 4-F—Ph | 4-F—Ph | Et | CHO |
| | 2,4-Cl₂—Ph | Me | Me | CHO |
| | 1-(4-F-Ph)ethenyl | 4-F—Ph | Me | CHO |
| | 4-F—Ph | Ph | Me | I |
| | Ph | Ph | Me | I |
| | 4-Cl—Ph | 4-Cl—Ph | Me | I |
| | 4-Cl—Ph | Ph | Me | I |
| | 4-F—Ph | 2-F—Ph | Me | I |
| | 4-F—Ph | 2,4-F₂—Ph | Me | I |
| | 4-F—Ph | 4-F—Ph | vinyl | I |
| | 4-F—Ph | 4-F—Ph | allyl | I |
| | 4-Ph—Ph | Me | Me | I |
| | 4-Ph—Ph | vinyl | vinyl | I |
| | 4-F—Ph | 4-F—Ph | OH | I |
| | 4-F—Ph | 4-F—Ph | O—t-Bu | I |
| | 4-F—Ph | 4-F—Ph | Et | I |
| | 2,4-Cl₂—Ph | Me | Me | I |
| | 1-(4-F-Ph)ethenyl | 4-F—Ph | Me | I |
| | PhCH=CH— | CH₃ | CH₃ | SH |
| | 4-F—PhCH=CH— | 4-F—Ph | CH₃ | SH |
| | (CH₃)₂C=CH₂— | 2,4-F₂—Ph | CH₃ | SH |
| | CH₂=C(Et)— | 4-Cl—Ph | CH₃ | SH |
| | 1-napthyl | 2-CF₃—Ph | CH₃ | SH |
| | 2-napthyl | CH₃ | CH₃ | SH |
| | PhC≡C— | 4-F—Ph | 4-F—Ph | SH |
| | n-BuC≡C | 4-F—Ph | CH₃ | SH |
| | CH₃C≡C— | 4-F—Ph | 4-F—Ph | SH |
| | 4-Ph—Ph | CH₂CH=C(CH₃)₂ | O—t-Bu | SH |
| | 4-F—Ph | 3-CF₃—Ph | Me | SH |
| | 4-MeO—Ph | 4-Cl—Ph | n-Bu | SH |
| | 4-(4-F—Ph)—Ph | vinyl | O—t-Bu | SH |
| | 4-CHF₂O—Ph | Ph | Me | SH |
| | 4-Br—Ph | n-hexyl | Me | SH |
| | 4-Me—Ph | 4-Me—Ph | Me | SH |
| | 4-CF₃O—Ph | 4-CF₃O—Ph | Me | SH |

TABLE I-continued $$R_2-\underset{\underset{R_3}{|}}{\overset{\overset{R_1}{|}}{Si}}-CH_2N\text{-triazole with X}$$

| Cmpd. No. | R₁ | R₂ | R₃ | X |
|---|---|---|---|---|
| | 4-(n-Bu)—Ph | 4-F—Ph | Me | SH |
| | 2,4-Cl₂—Ph | CH₂C(Me)=CH₂ | CH₂C(Me)=CH₂ | SH |
| | 4-F—Ph | 4-F—Ph | O—n-Bu | SH |
| | t-BuC≡C— | 4-F—Ph | Me | SH |
| | 2,6-MeO₂—Ph | Me | Me | SH |
| | 4-(t-Bu)—Ph | Me | Me | SH |
| | PhC(=CH₂)— (α-methylstyrenyl) | 4-F—Ph | Me | SH |
| | PhCH=CH— | CH₃ | CH₃ | —SS— |
| | 4-F—PhCH=CH— | 4-F—Ph | CH₃ | —SS— |
| | (CH₃)₂C=CH₂— | 2,4-F₂—Ph | CH₃ | —SS— |
| | CH₂=C(Et)— | 4-Cl—Ph | CH₃ | —SS— |
| | 1-napthyl | 2-CF₃—Ph | CH₃ | —SS— |
| | 2-napthyl | CH₃ | CH₃ | —SS— |
| | PhC≡C— | 4-F—Ph | 4-F—Ph | —SS— |
| | n-BuC≡C | 4-F—Ph | CH₃ | —SS— |
| | CH₃C≡C— | 4-F—Ph | 4-F—Ph | —SS— |
| | 4-Ph—Ph | CH₂CH=C(CH₃)₂ | O—t-Bu | —SS— |
| | 4-F—Ph | 3-CF₃—Ph | Me | —SS— |
| | 4-MeO—Ph | 4-Cl—Ph | n-Bu | —SS— |
| | 4-(4-F—Ph)—Ph | vinyl | O—t-Bu | —SS— |
| | 4-CHF₂O—Ph | Ph | Me | —SS— |
| | 4-Br—Ph | n-hexyl | Me | —SS— |
| | 4-Me—Ph | 4-Me—Ph | Me | —SS— |
| | 4-CF₃O—Ph | 4-CF₃O—Ph | Me | —SS— |
| | 4-(n-Bu)—Ph | 4-F—Ph | Me | —SS— |
| | 2,4-Cl₂—Ph | CH₂C(Me)=CH₂ | CH₂C(Me)=CH₂ | —SS— |
| | 4-F—Ph | 4-F—Ph | O—n-Bu | —SS— |
| | t-BuC≡C— | 4-F—Ph | Me | —SS— |
| | 2,6-MeO₂—Ph | Me | Me | —SS— |
| | 4-(t-Bu)—Ph | Me | Me | —SS— |
| | PhC(=CH₂)— (α-methylstyrenyl) | 4-F—Ph | Me | —SS— |
| | PhCH=CH— | CH₃ | CH₃ | —SC(O)NH—n-Bu |
| | 4-F—PhCH=CH— | 4-F—Ph | CH₃ | —SC(O)NH—n-Bu |
| | (CH₃)₂C=CH₂— | 2,4-F₂—Ph | CH₃ | —SC(O)NH—n-Bu |
| | CH₂=C(Et)— | 4-Cl—Ph | CH₃ | —SC(O)NH—n-Bu |
| | 1-napthyl | 2-CF₃—Ph | CH₃ | —SC(O)NH—n-Bu |
| | 2-napthyl | CH₃ | CH₃ | —SC(O)NH—n-Bu |
| | PhC≡C— | 4-F—Ph | 4-F—Ph | —SC(O)NH—n-Bu |

TABLE I-continued $$\begin{array}{c} R_1 \\ | \\ R_2-Si-CH_2N \\ | \\ R_3 \end{array} \begin{array}{c} X \\ \diagdown \\ N \\ \diagup \\ N= \end{array}$$

| Cmpd. No. | R₁ | R₂ | R₃ | X |
|---|---|---|---|---|
| | BuC≡C | 4-F—Ph | CH₃ | $\underset{\text{SCNH}-\underline{n}\text{-Bu}}{\overset{\overset{\text{O}}{\|}}{}}$ |
| | CH₃C≡C— | 4-F—Ph | 4-F—Ph | $\underset{\text{SCNH}-\underline{n}\text{-Bu}}{\overset{\overset{\text{O}}{\|}}{}}$ |
| | 4-Ph—Ph | CH₂CH=C(CH₃)₂ | O—t-Bu | $\underset{\text{SCNH}-\underline{n}\text{-Bu}}{\overset{\overset{\text{O}}{\|}}{}}$ |
| | 4-F—Ph | 3-CF₃—Ph | Me | $\underset{\text{SCNH}-\underline{n}\text{-Bu}}{\overset{\overset{\text{O}}{\|}}{}}$ |
| | 4-MeO—Ph | 4-Cl—Ph | n-Bu | $\underset{\text{SCNH}-\underline{n}\text{-Bu}}{\overset{\overset{\text{O}}{\|}}{}}$ |
| | 4-(4-F—Ph)—Ph | vinyl | O—t-Bu | $\underset{\text{SCNH}-\underline{n}\text{-Bu}}{\overset{\overset{\text{O}}{\|}}{}}$ |
| | 4-CHF₂O—Ph | Ph | Me | $\underset{\text{SCNH}-\underline{n}\text{-Bu}}{\overset{\overset{\text{O}}{\|}}{}}$ |
| | 4-Br—Ph | n-hexyl | Me | $\underset{\text{SCNH}-\underline{n}\text{-Bu}}{\overset{\overset{\text{O}}{\|}}{}}$ |
| | 4-Me—Ph | 4-Me—Ph | Me | $\underset{\text{SCNH}-\underline{n}\text{-Bu}}{\overset{\overset{\text{O}}{\|}}{}}$ |
| | 4-CF₃O—Ph | 4-CF₃O—Ph | Me | $\underset{\text{SCNH}-\underline{n}\text{-Bu}}{\overset{\overset{\text{O}}{\|}}{}}$ |
| | 4-(n-Bu)—Ph | 4-F—Ph | Me | $\underset{\text{SCNH}-\underline{n}\text{-Bu}}{\overset{\overset{\text{O}}{\|}}{}}$ |
| | 2,4-Cl₂—Ph | CH₂C(Me)=CH₂ | CH₂C(Me)=CH₂ | $\underset{\text{SCNH}-\underline{n}\text{-Bu}}{\overset{\overset{\text{O}}{\|}}{}}$ |
| | 4-F—Ph | 4-F—Ph | O—n-Bu | $\underset{\text{SCNH}-\underline{n}\text{-Bu}}{\overset{\overset{\text{O}}{\|}}{}}$ |
| | t-BuC≡C— | 4-F—Ph | Me | $\underset{\text{SCNH}-\underline{n}\text{-Bu}}{\overset{\overset{\text{O}}{\|}}{}}$ |
| | 2,6-MeO₂—Ph | Me | Me | $\underset{\text{SCNH}-\underline{n}\text{-Bu}}{\overset{\overset{\text{O}}{\|}}{}}$ |
| | 4-(t-Bu)—Ph | Me | Me | $\underset{\text{SCNH}-\underline{n}\text{-Bu}}{\overset{\overset{\text{O}}{\|}}{}}$ |

TABLE I-continued

| Cmpd. No. | R₁ | R₂ | R₃ | X |
|---|---|---|---|---|
|  | (1-phenylprop-1-en-2-yl) | 4-F—Ph | Me | SCNH—n-Bu (C=O) |

Footnotes to Table I
NMR Data (CDCl₃); peak position in parts per million downfield from tetramethylsilane.
1. 0.7 (s), 4.2 (s), 7.2 (t), 7.6 (m), 7.8 (s).
2. 0.7 (s), 4.2 (s), 7.1 (m), 7.5 (m), 7.8 (s).
3. 0.7 (s), 4.2 (s), 7.1 (t), 7.4 (m), 7.8 (s).
4. 0.7 (s), 3.7 (d), 4.0 (s), 5.1 (d), 5.2 (d), 5.8 (m), 7.1 (t), 7.5 (m), 7.8 (s).
5. 0.7 (s), 4.0 (d), 4.6 (s), 5.3 (m), 5.4 (d), 5.8 (m), 7.1 (t), 7.5 (m), 7.9 (s).
6. 0.7 (s), 4.0 (s), 4.6 (s), 7.1 (t), 7.5 (m), 7.9 (s).
7. 0.8 (s), 3.9 (s), 4.0 (s), 7.1 (m), 7.5 (m), 7.8 (s).
8. 0.8 (s), 4.1 (ABq), 4.6 (ABq), 7.1 (m), 7.5 (m), 8.0 (s).
9. 0.8 (s), 4.4 (s), 4.6 (s), 7.1 (t), 7.5 (m), 8.0 (s).
10. 0.7 (s), 3.7 (s), 3.9 (s), 4.0 (s), 7.1 (t), 7.7 (m), 7.8 (s).
11. 0.7 (s), 3.7 (s), 4.4 (s), 4.6 (s), 7.1 (t), 7.5 (m), 7.9 (s).
12. 0.7 (s), 2.2 (t), 3.8 (d), 4.1 (s), 7.1 (t), 7.5 (m), 7.8 (s).
13. 0.7 (s), 3.9 (s), 4.3 (s), 7.0 (t), 7.3 (s), 7.4 (m), 7.8 (s).
14. 0.8 (s), 3.3 (s), 4.3 (s), 5.3 (s), 7.1 (t), 7.6 (m), 7.8 (s).
15. 0.7 (s), 2.5 (s), 4.2 (s), 7.1 (t), 7.5 (m), 7.8 (s).
16. 0.7 (s), 1.0 (t), 1.7 (m), 2.8 (t), 4.2 (s), 7.1 (m), 7.5 (m), 7.8 (s).
17. 0.7 (s), 1.3 (d), 3.2 (heptet), 4.2 (s), 7.1 (t), 7.5 (m), 7.8 (s).
18. 0.7 (s), 4.1 (s), 7.1 (t), 7.2–7.6 (m), 7.9 (s).
19. 0.7 (s), 4.4 (s), 7.1 (t), 7.5 (d), 8.1 (s).
20. 0.7 (s), 3.0 (d), 4.2 (s), 7.1 (t), 7.5 (m), 8.4 (s), 10.0 (br s).
21. 0.7 (s), 1.0 (t), 1.4 (m), 1.6 (m), 3.4 (approximate q), 4.2 (s), 7.1 (t), 7.6 (m), 8.4 (s).
22. 0.7 (s), 1.4 (d), 2.9 (br d), 4.2 (s), 4.8 (m), 7.1 (m), 7.4 (m), 7.7 (s).
23. 0.6 (s), 3.6 (d), 3.9 (ABq), 5.8 (d), 6.9–7.1 (m), 7.2–7.4 (m), 7.8 (s).
24. 0.7 (s), 3.5 (br s), 4.2 (s), 5.4 (d), 6.2 (dd), 6.6 (d), 7.0 (m), 7.3 (s), 7.4 (m), 7.8 (s).
25. 0.7 (s), 1.6 (s), 3.9 (br s), 4.1 (ABq), 5.2 (s), 6.6 (s), 7.0 (q), 7.2–7.5 (m), 7.8 (s).
26. 0.7 (s), 2.5 (s), 4.8 (s), 7.0 (t), 7.4 (t), 7.8 (s).
27. 0.8 (s), 2.3 (s), 4.9 (s), 7.0–7.3 (m), 7.5 (t), 7.9 (s).
28. 0.7 (s), 1.3 (t), 4.0 (m), 4.7 (s), 7.0 (t), 7.5 (m), 7.9 (s).
29. 0.7 (s), 3.9 (s), 4.8 (s), 7.2 (m), 7.6 (m), 8.0 (s).
30. 0.6 (s), 3.7, 4.2 (two d, ABq), 4.2, 4.4 (two d, ABq), 7.0 (m), 7.5 (m), 7.9 (s).
31. 0.6 (s), 4.1 (s), 4.5 (s), 7.0–7.7 (m), 7.9 (s).
32. 0.7 (s), 4.1 (s), 4.2 (s), 7.1 (t), 7.5 (s), 7.5 (m), 7.9 (s).
33. 0.8 (s), 4.0 (m), 4.2 (s), 5.3 (m), 5.9 (m), 7.1 (m), 7.5 (m), 8.4 (s), 10.3 (br s).
34. 0.7 (s), 1.3 (d), 4.1 (m), 4.2 (s), 7.1 (m), 7.5 (m), 8.4 (s), 10.1 (br d).
35. 0.7 (s), 4.8 (s), 7.0 (m), 7.4–7.7 (m), 7.9 (s), 8.0 (m).
36. 0.7 (s), 3.7 (s), 4.0 (s), 7.1 (t), 7.5 (m), 7.8 (s), 10.8 (br.s).
37. 0.7 (s), 2.3 (s), 4.0 (two s), 7.1 (t), 7.5 (m), 7.7 (s).
38. 0.7 (s), 2.1 (s), 4.7 (s), 7.1 (t), 7.5 (m), 7.8 (s), 7.9 (s).
39. 0.7 (s), 3.7 (s), 3.8 (s), 4.8 (s), 6.5 (br s), 7.0 (m), 7.4 (m), 7.8 (s).
40. 0.7 (s), 0.8 (s), 1.1 (d), 1.4 (s), 2.2 (m), 2.5 (m), 3.0 (t), 4.7 (ABq), 7.0 (t), 7.2 (m), 7.5 (m), 7.8 (s).
41. 0.7 (s), 1.1 (d), 2.1 (m), 2.7 (m), 4.6 (s), 5.0 (m), 5.7 (m), 6.9 (d), 7.0 (t), 7.5 (m), 7.8 (s).
42. 0.8 (s), 2.3 (s), 4.4 (s), 4.6 (s), 7.1 (m), 7.5 (m), 7.8 (s).
43. 0.7 (s), 3.6 (s), 4.0 (s), 4.1 (s), 4.2 (q), 7.1 (t), 7.5 (m), 7.7 (s), 12.1 (br. s).
44. 0.7 (s), 1.7 (d), 4.1 (s), 4.3 (q), 7.1 (m), 7.5 (m), 7.9 (s).
45. 0.7 (s), 1.0 (d), 3.0 (heptet), 4.7 (s), 5.9 (s), 6.1 (s), 7.0 (t), 7.5 (m), 7.8 (s).
46. 0.7 (s), 4.2 (s), 5.5 (dd), 6.4 (m), 7.1 (m), 7.5 (m), 7.9 (s).

TABLE II

| Cmpd. No. | R₁ | R₂ | R₃ | X |
|---|---|---|---|---|
|  | 4-F—Ph | 4-F—Ph | Me | vinyl |
|  | 4-F—Ph | 4-F—Ph | Me | ethynyl |
|  | 4-F—Ph | 4-F—Ph | Me | F |
|  | 4-F—Ph | 4-F—Ph | Me | Cl |
|  | 4-F—Ph | 4-F—Ph | Me | I |
|  | 4-F—Ph | 4-F—Ph | Me | NO₂ |

TABLE II-continued $$\text{R}_2-\underset{\underset{R_3}{|}}{\overset{\overset{R_1}{|}}{Si}}-\text{CH}-\underset{\underset{N}{\diagdown}}{N}\underset{=\diagup}{\overset{\overset{Me}{|}}{\diagdown}}\overset{X}{\underset{N}{\diagup}}$$

| Cmpd. No. | $R_1$ | $R_2$ | $R_3$ | X | |
|---|---|---|---|---|---|
| | 4-F—Ph | 4-F—Ph | Me | NH$_2$ | |
| | 4-F—Ph | 4-F—Ph | Me | Me$_2$N | |
| | 4-F—Ph | 4-F—Ph | Me | SH | |
| | 4-F—Ph | 4-F—Ph | Me | —SS— | |
| | 4-F—Ph | 4-F—Ph | Me | SMe | |
| | 4-F—Ph | 4-F—Ph | Me | S(O)Me | |
| | 4-F—Ph | 4-F—Ph | Me | SO$_2$Me | |
| | 4-F—Ph | 4-F—Ph | Me | SCCl$_3$ | |
| | 4-F—Ph | 4-F—Ph | Me | SCH$_2$SCN | |
| | 4-F—Ph | 4-F—Ph | Me | S(O)CH$_2$SCN | |
| | 4-F—Ph | 4-F—Ph | Me | SO$_2$CH$_2$SCN | |
| | 4-F—Ph | 4-F—Ph | Me | SCH$_2$CN | |
| | 4-F—Ph | 4-F—Ph | Me | S(O)CH$_2$CN | |
| | 4-F—Ph | 4-F—Ph | Me | SO$_2$CH$_2$CN | |
| | 4-F—Ph | 4-F—Ph | Me | SCH$_2$CO$_2$Me | |
| | 4-F—Ph | 4-F—Ph | Me | S(O)CH$_2$CO$_2$Me | |
| | 4-F—Ph | 4-F—Ph | Me | SO$_2$CH$_2$CO$_2$Me | |
| | 4-F—Ph | 4-F—Ph | Me | SCH$_2$C≡CH | |
| | 4-F—Ph | 4-F—Ph | Me | SO$_2$CH$_2$C≡CH | |
| | 4-F—Ph | 4-F—Ph | Me | SSMe | |
| | 4-F—Ph | 4-F—Ph | Me | SNH$_2$ | |
| | 4-F—Ph | 4-F—Ph | Me | SNHMe | |
| | 4-F—Ph | 4-F—Ph | Me | SNMe$_2$ | |
| | 4-F—Ph | 4-F—Ph | Me | SeH | |
| | 4-F—Ph | 4-F—Ph | Me | —SeSe— | |
| | 4-F—Ph | 4-F—Ph | Me | NHNH$_2$ | |
| | 4-F—Ph | 4-F—Ph | Me | $\overset{\overset{O}{\|}}{SCNHMe}$ | |
| | 4-F—Ph | 4-F—Ph | Me | $\overset{\overset{O}{\|}}{SCNH}$—n-Bu | |
| | 4-F—Ph | 4-F—Ph | Me | $\overset{\overset{O}{\|}}{SCNH}$—i-Pr | |
| | 4-F—Ph | 4-F—Ph | Me | $\overset{\overset{O}{\|}}{SCNHCH_2CH=CH_2}$ | |
| | 4-F—Ph | 4-F—Ph | Me | $\overset{\overset{O}{\|}}{SCNHPh}$ | |
| | 4-F—Ph | 4-F—Ph | Me | $\overset{\overset{S}{\|}}{SCNH}$—n-Bu | |
| | 4-F—Ph | 4-F—Ph | Me | $\overset{\overset{S}{\|}}{SCNHPh}$ | |
| | 4-F—Ph | 4-F—Ph | Me | MeN=C(OMe)S | |
| | 4-F—Ph | 4-F—Ph | Me | CH(OH)vinyl | |
| 89. | 4-F—Ph | 4-F—Ph | Me | CH(OH)CH=CHCH$_3$ | m.p. 90-92° |
| | 4-F—Ph | 4-F—Ph | Me | CH(OH)CH=CHPh | |
| | 4-F—Ph | 4-F—Ph | Me | CH(OH)—4-Cl—Ph | |
| | 4-F—Ph | 4-F—Ph | Me | CHO | |
| | 4-F—Ph | 4-F—Ph | Me | CO—i-Pr | |
| | 4-F—Ph | 4-F—Ph | Me | COCH=CH$_2$ | |
| | 4-F—Ph | 4-F—Ph | Me | COCH=CHCH$_3$ | |
| | 4-F—Ph | 4-F—Ph | Me | COCH=CHPh | |
| | 4-F—Ph | 4-F—Ph | Me | COPh | |
| | 4-F—Ph | 4-F—Ph | Me | CO—4-Cl—Ph | |
| | 4-F—Ph | 4-F—Ph | Me | PO(OEt)$_2$ | |
| | 4-F—Ph | 4-F—Ph | Me | CONHMe | |
| | 4-F—Ph | 4-F—Ph | Me | CONHPh | |
| | 4-F—Ph | 4-F—Ph | Me | CONH—n-Bu | |
| | 4-F—Ph | 4-F—Ph | Me | CSNHMe | |
| | 4-F—Ph | 4-F—Ph | Me | CSNH—n-Bu | |
| | 4-F—Ph | 4-F—Ph | Me | CO$_2$Me | |

TABLE II-continued $$\underset{R_3}{\overset{R_1}{\underset{|}{R_2-Si-}}}\overset{Me}{\underset{|}{CH}}-\underset{N}{\overset{}{N}}\underset{\underset{N}{\diagdown}}{\overset{X}{\diagup}}\underset{\diagdown}{\overset{}{N}}$$

| Cmpd. No. | R₁ | R₂ | R₃ | X |
|---|---|---|---|---|
| | 4-F—Ph | 4-F—Ph | Me | CS₂Me |
| | 4-F—Ph | 4-F—Ph | Me | COSMe |
| | 4-F—Ph | Ph | Me | SH |
| | Ph | Ph | Me | SH |
| | 4-Cl—Ph | 4-Cl—Ph | Me | SH |
| | 4-Cl—Ph | Ph | Me | SH |
| | 4-F—Ph | 2-F—Ph | Me | SH |
| | 4-F—Ph | 2,4-F₂—Ph | Me | SH |
| | 4-F—Ph | 4-F—Ph | vinyl | SH |
| | 4-F—Ph | 4-F—Ph | allyl | SH |
| | 4-Ph—Ph | Me | Me | SH |
| | 4-Ph—Ph | vinyl | vinyl | SH |
| | 4-F—Ph | 4-F—Ph | OH | SH |
| | 4-F—Ph | 4-F—Ph | O—t-Bu | SH |
| | 4-F—Ph | 4-F—Ph | Et | SH |
| | 2,4-Cl₂—Ph | Me | Me | SH |
| | 4-F-C₆H₄-C(=CH₂)- | 4-F—Ph | Me | SH |
| | 4-F—Ph | Ph | Me | —SS— |
| | Ph | Ph | Me | —SS— |
| | 4-Cl—Ph | 4-Cl—Ph | Me | —SS— |
| | 4-Cl—Ph | Ph | Me | —SS— |
| | 4-F—Ph | 2-F—Ph | Me | —SS— |
| | 4-F—Ph | 2,4-F₂—Ph | Me | —SS— |
| | 4-F—Ph | 4-F—Ph | vinyl | —SS— |
| | 4-F—Ph | 4-F—Ph | allyl | —SS— |
| | 4-Ph—Ph | Me | Me | —SS— |
| | 4-Ph—Ph | vinyl | vinyl | —SS— |
| | 4-F—Ph | 4-F—Ph | OH | —SS— |
| | 4-F—Ph | 4-F—Ph | O—t-Bu | —SS— |
| | 4-F—Ph | 4-F—Ph | Et | —SS— |
| | 2,4-Cl₂—Ph | Me | Me | —SS— |
| | 4-F-C₆H₄-C(=CH₂)- | 4-F—Ph | Me | —SS— |
| | 4-F—Ph | Ph | Me | SSMe |
| | Ph | Ph | Me | SSMe |
| | 4-Cl—Ph | 4-Cl—Ph | Me | SSMe |
| | 4-Cl—Ph | Ph | Me | SSMe |
| | 4-F—Ph | 2-F—Ph | Me | SSMe |
| | 4-F—Ph | 2,4-F₂—Ph | Me | SSMe |
| | 4-F—Ph | 4-F—Ph | vinyl | SSMe |
| | 4-F—Ph | 4-F—Ph | allyl | SSMe |
| | 4-Ph—Ph | Me | Me | SSMe |
| | 4-Ph—Ph | vinyl | vinyl | SSMe |
| | 4-F—Ph | 4-F—Ph | OH | SSMe |
| | 4-F—Ph | 4-F—Ph | O—t-Bu | SSMe |
| | 4-F—Ph | 4-F—Ph | Et | SSMe |
| | 2,4-Cl₂—Ph | Me | Me | SSMe |
| | 4-F-C₆H₄-C(=CH₂)- | 4-F—Ph | Me | SSMe |
| | 4-F—Ph | Ph | Me | $\underset{\text{SCNH—n-Bu}}{\overset{O}{\|}}$ |

TABLE II-continued

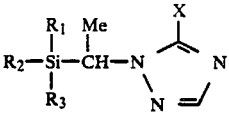

| Cmpd. No. | R₁ | R₂ | R₃ | X |
|---|---|---|---|---|
| | Ph | Ph | Me | $\underset{\|}{\overset{O}{\|}}$ SCNH—n-Bu |
| | 4-Cl—Ph | 4-Cl—Ph | Me | $\overset{O}{\|}$ SCNH—n-Bu |
| | 4-Cl—Ph | Ph | Me | $\overset{O}{\|}$ SCNH—n-Bu |
| | 4-F—Ph | 2-F—Ph | Me | $\overset{O}{\|}$ SCNH—n-Bu |
| | 4-F—Ph | 2,4-F₂—Ph | Me | $\overset{O}{\|}$ SCNH—n-Bu |
| | 4-F—Ph | 4-F—Ph | vinyl | $\overset{O}{\|}$ SCNH—n-Bu |
| | 4-F—Ph | 4-F—Ph | allyl | $\overset{O}{\|}$ SCNH—n-Bu |
| | 4-Ph—Ph | Me | Me | $\overset{O}{\|}$ SCNH—n-Bu |
| | 4-Ph—Ph | vinyl | vinyl | $\overset{O}{\|}$ SCNH—n-Bu |
| | 4-F—Ph | 4-F—Ph | OH | $\overset{O}{\|}$ SCNH—n-Bu |
| | 4-F—Ph | 4-F—Ph | O—t-Bu | $\overset{O}{\|}$ SCNH—n-Bu |
| | 4-F—Ph | 4-F—Ph | Et | $\overset{O}{\|}$ SCNH—n-Bu |
| | 2,4-Cl₂—Ph | Me | Me | $\overset{O}{\|}$ SCNH—n-Bu |
| |  | 4-F—Ph | Me | $\overset{O}{\|}$ SCNH—n-Bu |
| | 4-F—Ph | Ph | Me | CHO |
| | Ph | Ph | Me | CHO |
| | 4-Cl—Ph | 4-Cl—Ph | Me | CHO |
| | 4-Cl—Ph | Ph | Me | CHO |
| | 4-F—Ph | 2-F—Ph | Me | CHO |
| | 4-F—Ph | 2,4-F₂—Ph | Me | CHO |
| | 4-F—Ph | 4-F—Ph | vinyl | CHO |
| | 4-F—Ph | 4-F—Ph | allyl | CHO |
| | 4-Ph—Ph | Me | Me | CHO |
| | 4-Ph—Ph | vinyl | vinyl | CHO |
| | 4-F—Ph | 4-F—Ph | OH | CHO |
| | 4-F—Ph | 4-F—Ph | O—t-Bu | CHO |

TABLE II-continued $$R_2-\underset{\underset{R_3}{|}}{\overset{\overset{R_1}{|}}{Si}}-\underset{\underset{}{}}{\overset{Me}{C}H}-N\underset{N}{\overset{\diagup}{\diagdown}}\underset{}{\overset{X}{\diagup\diagdown}}N$$

| Cmpd. No. | R₁ | R₂ | R₃ | X |
|---|---|---|---|---|
| | 4-F—Ph | 4-F—Ph | Et | CHO |
| | 2,4-Cl₂—Ph | Me | Me | CHO |
| | [4-fluorophenyl-isopropenyl group] | 4-F—Ph | Me | CHO |

TABLE III $$R_2-\underset{\underset{R_3}{|}}{\overset{\overset{R_1}{|}}{Si}}-CH_2N\underset{N}{\overset{\diagup}{\diagdown}}\underset{Y}{\overset{}{\diagup\diagdown}}N$$

| Cmpd. No. | R₁ | R₂ | R₃ | Y | |
|---|---|---|---|---|---|
| | 4-F—Ph | 4-F—Ph | Me | F | |
| | 4-F—Ph | 4-F—Ph | Me | Cl | |
| | 4-F—Ph | 4-F—Ph | Me | Br | |
| | 4-F—Ph | 4-F—Ph | Me | I | |
| 90. | 4-F—Ph | 4-F—Ph | Me | NH₂ | m.p. 116–117° |
| 91. | 4-F—Ph | 4-F—Ph | Me | NH₃⁺Cl⁻ | m.p. 191–194° |
| 92. | 4-F—Ph | 4-F—Ph | Me | SH | m.p. 164–165° |
| 93. | 4-F—Ph | 4-F—Ph | Me | —SS— | oil¹ |
| 94. | 4-F—Ph | 4-F—Ph | Me | SMe | oil² |
| | 4-F—Ph | 4-F—Ph | Me | S(O)Me | |
| | 4-F—Ph | 4-F—Ph | Me | SO₂Me | |
| | 4-F—Ph | 4-F—Ph | Me | SEt | |
| | 4-F—Ph | 4-F—Ph | Me | S(O)Et | |
| | 4-F—Ph | 4-F—Ph | Me | SO₂Et | |
| | 4-F—Ph | 4-F—Ph | Me | S—n-Pr | |
| | 4-F—Ph | 4-F—Ph | Me | S(O)—n-Pr | |
| | 4-F—Ph | 4-F—Ph | Me | SO₂—n-Pr | |
| | 4-F—Ph | 4-F—Ph | Me | SCH₂CHMe₂ | |
| | 4-F—Ph | 4-F—Ph | Me | S(O)CH₂CHMe₂ | |
| | 4-F—Ph | 4-F—Ph | Me | SO₂CH₂CHMe₂ | |
| | 4-F—Ph | 4-F—Ph | Me | SCH₂CH=CH₂ | |
| | 4-F—Ph | 4-F—Ph | Me | S(O)CH₂CH=CH₂ | |
| | 4-F—Ph | 4-F—Ph | Me | SO₂CH₂CH=CH₂ | |
| 95. | 4-F—Ph | 4-F—Ph | Me | SCH₂SCN | oil³ |
| | 4-F—Ph | 4-F—Ph | Me | S(O)CH₂SCN | |
| 96. | 4-F—Ph | 4-F—Ph | Me | SO₂CH₂SCN | oil⁴ |
| | 4-F—Ph | 4-F—Ph | Me | SCH₂CN | |
| | 4-F—Ph | 4-F—Ph | Me | S(O)CH₂CN | |
| | 4-F—Ph | 4-F—Ph | Me | SO₂CH₂CN | |
| | 4-F—Ph | 4-F—Ph | Me | SSMe | |
| | 4-F—Ph | 4-F—Ph | Me | SSEt | |
| | 4-F—Ph | 4-F—Ph | Me | SS—n-Pr | |
| | 4-F—Ph | 4-F—Ph | Me | SS—i-Pr | |
| | 4-F—Ph | 4-F—Ph | Me | SS—n-Bu | |
| | 4-F—Ph | 4-F—Ph | Me | SSCH₂Ph | |
| | 4-F—Ph | 4-F—Ph | Me | SSCCl₃ | |
| | 4-F—Ph | 4-F—Ph | Me | SSPh | |
| | 4-F—Ph | 4-F—Ph | Me | SS—4-F—Ph | |
| | 4-F—Ph | 4-F—Ph | Me | SS—3-CF₃—Ph | |
| | 4-F—Ph | 4-F—Ph | Me | SS—4-MeO—Ph | |
| | 4-F—Ph | 4-F—Ph | Me | $\underset{\text{SCNH}_2}{\overset{\overset{O}{\|}}{}}$ | |
| | 4-F—Ph | 4-F—Ph | Me | $\underset{\text{SCNHMe}}{\overset{\overset{O}{\|}}{}}$ | |

TABLE III-continued $$R_2-\underset{\underset{R_3}{|}}{\overset{\overset{R_1}{|}}{Si}}-CH_2N\underset{N}{\overset{\frown}{\diagdown}}\underset{Y}{\overset{N}{\diagup}}$$

| Cmpd. No. | R₁ | R₂ | R₃ | Y |
|---|---|---|---|---|
| | 4-F—Ph | 4-F—Ph | Me | $\underset{SCNHEt}{\overset{O}{\|}}$ |
| | 4-F—Ph | 4-F—Ph | Me | $\underset{SCNH-n\text{-}Pr}{\overset{O}{\|}}$ |
| | 4-F—Ph | 4-F—Ph | Me | $\underset{SCNH-n\text{-}Bu}{\overset{O}{\|}}$ |
| | 4-F—Ph | 4-F—Ph | Me | $\underset{SCNH-i\text{-}Pr}{\overset{O}{\|}}$ |
| | 4-F—Ph | 4-F—Ph | Me | $\underset{SCNH-t\text{-}Bu}{\overset{O}{\|}}$ |
| | 4-F—Ph | 4-F—Ph | Me | $\underset{SCNH-s\text{-}Bu}{\overset{O}{\|}}$ |
| | 4-F—Ph | 4-F—Ph | Me | $\underset{SCNHCH_2Ph}{\overset{O}{\|}}$ |
| | 4-F—Ph | 4-F—Ph | Me | $\underset{SCNHCH_2CH=CH_2}{\overset{O}{\|}}$ |
| | 4-F—Ph | 4-F—Ph | Me | $\underset{SCNHPh}{\overset{O}{\|}}$ |
| | 4-F—Ph | 4-F—Ph | Me | $\underset{SCNH-4\text{-}Cl-Ph}{\overset{O}{\|}}$ |
| | 4-F—Ph | 4-F—Ph | Me | $\underset{SCNH-4\text{-}F-Ph}{\overset{O}{\|}}$ |
| | 4-F—Ph | 4-F—Ph | Me | $\underset{SCNH-3\text{-}Me-Ph}{\overset{O}{\|}}$ |
| | 4-F—Ph | 4-F—Ph | Me | $\underset{SCNH-2\text{-}CF_3-Ph}{\overset{O}{\|}}$ |
| | 4-F—Ph | 4-F—Ph | Me | $\underset{SCNH-4\text{-}MeO-Ph}{\overset{O}{\|}}$ |
| | 4-F—Ph | 4-F—Ph | Me | $\underset{SCNH-4\text{-}Me-Ph}{\overset{O}{\|}}$ |
| | 4-F—Ph | 4-F—Ph | Me | $\underset{SCNH-3,5\text{-}Cl_2-Ph}{\overset{O}{\|}}$ |
| | 4-F—Ph | 4-F—Ph | Me | $\underset{SCNH-3\text{-}MeO-Ph}{\overset{O}{\|}}$ |
| | 4-F—Ph | 4-F—Ph | Me | $\underset{SCNH-4\text{-}NO_2-Ph}{\overset{O}{\|}}$ |

TABLE III-continued

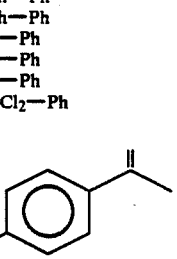

| Cmpd. No. | R₁ | R₂ | R₃ | Y |
|---|---|---|---|---|
| | 4-F—Ph | 4-F—Ph | Me | $\overset{O}{\underset{\|}{S}}CNH-2,6-Cl_2-Ph$ |
| | 4-F—Ph | 4-F—Ph | Me | $\overset{O}{\underset{\|}{S}}CNH-4-MeO-Ph$ |
| | 4-F—Ph | 4-F—Ph | Me | $\overset{O}{\underset{\|}{S}}CNH-2,4-Me_2-Ph$ |
| | 4-F—Ph | 4-F—Ph | Me | $\overset{S}{\underset{\|}{S}}CNH_2$ |
| | 4-F—Ph | 4-F—Ph | Me | $\overset{S}{\underset{\|}{S}}CNHMe$ |
| | 4-F—Ph | 4-F—Ph | Me | $\overset{S}{\underset{\|}{S}}CNHCH_2CH=CH_2$ |
| | 4-F—Ph | 4-F—Ph | Me | $\overset{S}{\underset{\|}{S}}CNHCH_2Ph$ |
| | 4-F—Ph | 4-F—Ph | Me | $\overset{S}{\underset{\|}{S}}CNH-\underline{n}-Bu$ |
| | 4-F—Ph | 4-F—Ph | Me | $\overset{S}{\underset{\|}{S}}CNHPh$ |
| | 4-F—Ph | 4-F—Ph | Me | $\overset{S}{\underset{\|}{S}}CNH-4-Cl-Ph$ |
| | 4-F—Ph | 4-F—Ph | Me | CHO |
| | 4-F—Ph | 4-F—Ph | Me | CO₂Me |
| | 4-F—Ph | Ph | Me | SH |
| | Ph | Ph | Me | SH |
| | 4-Cl—Ph | 4-Cl—Ph | Me | SH |
| | 4-F—Ph | 2-F—Ph | Me | SH |
| | 4-F—Ph | 2,4-F₂—Ph | Me | SH |
| | 4-F—Ph | 4-F—Ph | vinyl | SH |
| | 4-F—Ph | 4-F—Ph | allyl | SH |
| | 4-Ph—Ph | Me | Me | SH |
| | 4-Ph—Ph | vinyl | vinyl | SH |
| | 4-F—Ph | 4-F—Ph | OH | SH |
| | 4-F—Ph | 4-F—Ph | O—t-Bu | SH |
| | 4-F—Ph | 4-F—Ph | Er | SH |
| | 2,4-Cl₂—Ph | Me | Me | SH |
| | 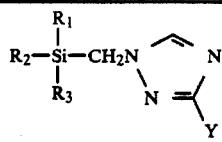 | 4-F—Ph | Me | SH |
| | 4-F—Ph | Ph | Me | —SS— |
| | Ph | Ph | Me | —SS— |
| | 4-Cl—Ph | 4-Cl—Ph | Me | —SS— |
| | 4-Cl—Ph | Ph | Me | —SS— |
| | 4-F—Ph | 2-F—Ph | Me | —SS— |
| | 4-F—Ph | 2,4-F₂—Ph | ME | —SS— |
| | 4-F—Ph | 4-F—Ph | vinyl | —SS— |
| | 4-F—Ph | 4-F—Ph | allyl | —SS— |
| | 4-Ph—Ph | Me | Me | —SS— |
| | 4-Ph—Ph | vinyl | vinyl | —SS— |
| | 4-F—Ph | 4-F—Ph | OH | —SS— |

TABLE III-continued $$R_2-\underset{\underset{R_3}{|}}{\overset{\overset{R_1}{|}}{Si}}-CH_2N\text{-triazole-}Y$$

| Cmpd. No. | R₁ | R₂ | R₃ | Y |
|---|---|---|---|---|
| | 4-F—Ph | 4-F—Ph | O—t-Bu | —SS— |
| | 4-F—Ph | 4-F—Ph | Et | —SS— |
| | 2,4-Cl₂—Ph | Me | Me | —SS— |
| | 1-(4-F-Ph)vinyl | 4-F—Ph | Me | —SS— |
| | 4-F—Ph | Ph | Me | SMe |
| | Ph | Ph | ME | SMe |
| | 4-Cl—Ph | 4-Cl—Ph | Me | SMe |
| | 4-Cl—Ph | Ph | Me | SMe |
| | 4-F—Ph | 2-F—Ph | Me | SMe |
| | 4-F—Ph | 2,4-F₂—Ph | Me | SMe |
| | 4-F—Ph | 4-F—Ph | vinyl | SMe |
| | 4-F—Ph | 4-F—Ph | allyl | SMe |
| | 4-Ph—Ph | Me | Me | SMe |
| | 4-Ph—Ph | vinyl | vinyl | SMe |
| | 4-F—Ph | 4-F—Ph | OH | SMe |
| | 4-F—Ph | 4-F—Ph | O—t-Bu | SMe |
| | 4-F—Ph | 4-F—Ph | Et | SMe |
| | 2,4-Cl₂—Ph | Me | Me | SMe |
| | 1-(4-F-Ph)vinyl | 4-F—Ph | Me | SMe |
| | 4-F—Ph | Ph | Me | S(O)Me |
| | Ph | Ph | Me | S(O)Me |
| | 4-Cl—Ph | 4-Cl—Ph | Me | S(O)Me |
| | 4-Cl—Ph | Ph | Me | S(O)Me |
| | 4-F—Ph | 2-F—Ph | Me | S(O)Me |
| | 4-F—Ph | 2,4-F₂—Ph | Me | S(O)Me |
| | 4-F—Ph | 4-F—Ph | vinyl | S(O)Me |
| | 4-F—Ph | 4-F—Ph | allyl | S(O)Me |
| | 4-Ph—Ph | Me | Me | S(O)Me |
| | 4-Ph—Ph | vinyl | vinyl | S(O)Me |
| | 4-F—Ph | 4-F—Ph | OH | S(O)Me |
| | 4-F—Ph | 4-F—Ph | O—t-Bu | S(O)Me |
| | 4-F—Ph | 4-F—Ph | Et | S(O)Me |
| | 2,4-Cl₂—Ph | Me | Me | S(O)Me |
| | 1-(4-F-Ph)vinyl | 4-F—Ph | Me | S(O)Me |
| | 4-F—Ph | Ph | Me | SO₂Me |
| | Ph | Ph | Me | SO₂Me |
| | 4-Cl—Ph | 4-Cl—Ph | Me | SO₂Me |
| | 4-Cl—Ph | Ph | Me | SO₂Me |
| | 4-F—Ph | 2-F—Ph | Me | SO₂Me |
| | 4-F—Ph | 2,4-F₂—Ph | Me | SO₂Me |
| | 4-F—Ph | 4-F—Ph₂ | vinyl | SO₂Me |
| | 4-F—Ph | 4-F—Ph₂ | allyl | SO₂Me |
| | 4-Ph—Ph | Me | Me | SO₂Me |
| | 4-Ph—Ph | vinyl² | vinyl | SO₂Me |
| | 4-F—Ph | 4-F—Ph₂ | OH | SO₂Me |
| | 4-F—Ph | 4-F—Ph₂ | O—t-Bu | SO₂Me |
| | 4-F—Ph | 4-F—Ph | Et | SO₂Me |
| | 2,4-Cl₂—Ph | Me | Me | SO₂Me |

TABLE III-continued $$R_2-\underset{\underset{R_3}{|}}{\overset{\underset{|}{R_1}}{Si}}-CH_2N\underset{N}{\overset{\frown}{\underset{\|}{\diagdown}}}\overset{N}{\underset{Y}{\diagup}}$$

| Cmpd. No. | R₁ | R₂ | R₃ | Y |
|---|---|---|---|---|
| | 4-(1-propenyl)-4-F-Ph | 4-F—Ph | Me | SO₂Me |
| | 4-F—Ph | Ph | Me | SSMe |
| | Ph | Ph | Me | SSMe |
| | 4-Cl—Ph | 4-Cl—Ph | Me | SSMe |
| | 4-F—Ph | 2-F—Ph | Me | SSMe |
| | 4-F—Ph | 2,4-F₂—Ph | Me | SSMe |
| | 4-F—Ph | 4-F—Ph | vinyl | SSMe |
| | 4-F—Ph | 4-F—Ph | allyl | SSMe |
| | 4-Ph—Ph | Me | Me | SSMe |
| | 4-Ph—Ph | vinyl | vinyl | SSMe |
| | 4-F—Ph | 4-F—Ph | OH | SSMe |
| | 4-F—Ph | 4-F—Ph | O—t-Bu | SSMe |
| | 4-F—Ph | 4-F—Ph | Et | SSMe |
| | 2,4-Cl₂—Ph | Me | Me | SSMe |
| | 4-(1-propenyl)-4-F-Ph | 4-F—Ph | Me | SSMe |
| | 4-F—Ph | Ph | Me | $\underset{\|}{\overset{O}{\|}}$SCNHMe |
| | Ph | Ph | Me | $\overset{O}{\underset{\|}{\|}}$SCNHMe |
| | 4-Cl—Ph | 4-Cl—Ph | Me | $\overset{O}{\underset{\|}{\|}}$SCNHMe |
| | 4-Cl—Ph | Ph | Me | $\overset{O}{\underset{\|}{\|}}$SCNHMe |
| | 4-F—Ph | 2-F—Ph | Me | $\overset{O}{\underset{\|}{\|}}$SCNHMe |
| | 4-F—Ph | 2,4-F₂—Ph | Me | $\overset{O}{\underset{\|}{\|}}$SCNHMe |
| | 4-F—Me | 4-F—Ph | vinyl | $\overset{O}{\underset{\|}{\|}}$SCNHMe |
| | 4-F—Ph | 4-F—Ph | allyl | $\overset{O}{\underset{\|}{\|}}$SCNHMe |
| | 4-Ph—Ph | Me | Me | $\overset{O}{\underset{\|}{\|}}$SCNHMe |
| | 4-Ph—Ph | vinyl | vinyl | $\overset{O}{\underset{\|}{\|}}$SCNHMe |
| | 4-F—Ph | 4-F—Ph | OH | $\overset{O}{\underset{\|}{\|}}$SCNHMe |
| | 4-F—Ph | 4-F—Ph | O—t-Bu | $\overset{O}{\underset{\|}{\|}}$SCNHMe |

TABLE III-continued $$\begin{array}{c} R_1 \\ | \\ R_2-Si-CH_2N \\ | \\ R_3 \end{array} \diagdown \begin{array}{c} N \\ \| \\ N \\ | \\ Y \end{array}$$

| Cmpd. No. | R₁ | R₂ | R₃ | Y |
|---|---|---|---|---|
| | 4-F—Ph | 4-F—Ph | Et | $\underset{SCNHMe}{\overset{O}{\|}}$ |
| | 2,4-Cl₂—Ph | Me | Me | $\underset{SCNHMe}{\overset{O}{\|}}$ |
| | 4-F-C₆H₄-C(=CH₂)- | 4-F—Ph | Me | $\underset{SCNHMe}{\overset{O}{\|}}$ |
| | 4-F—Ph | Ph | Me | $\underset{SCNH-\underline{n}\text{-}Bu}{\overset{O}{\|}}$ |
| | Ph | Ph | Me | $\underset{SCNH-\underline{n}\text{-}Bu}{\overset{O}{\|}}$ |
| | 4-Cl—Ph | 4-Cl—Ph | Me | $\underset{SCNH-\underline{n}\text{-}Bu}{\overset{O}{\|}}$ |
| | 4-Cl—Ph | Ph | Me | $\underset{SCNH-\underline{n}\text{-}Bu}{\overset{O}{\|}}$ |
| | 4-F—Ph | 2-F—Ph | Me | $\underset{SCNH-\underline{n}\text{-}Bu}{\overset{O}{\|}}$ |
| | 4-F—Ph | 2,4-F₂—Ph | Me | $\underset{SCNH-\underline{n}\text{-}Bu}{\overset{O}{\|}}$ |
| | 4-F—Ph | 4-F—Ph | vinyl | $\underset{SCNH-\underline{n}\text{-}Bu}{\overset{O}{\|}}$ |
| | 4-F—Ph | 4-F—Ph | allyl | $\underset{SCNH-\underline{n}\text{-}Bu}{\overset{O}{\|}}$ |
| | 4-Ph—Ph | Me | Me | $\underset{SCNH-\underline{n}\text{-}Bu}{\overset{O}{\|}}$ |
| | 4-Ph—Ph | vinyl | vinyl | $\underset{SCNH-\underline{n}\text{-}Bu}{\overset{O}{\|}}$ |
| | 4-F—Ph | 4-F—Ph | OH | $\underset{SCNH-\underline{n}\text{-}Bu}{\overset{O}{\|}}$ |
| | 4-F—Ph | 4-F—Ph | O—t-Bu | $\underset{SCNH-\underline{n}\text{-}Bu}{\overset{O}{\|}}$ |
| | 4-F—Ph | 4-F—Ph | Et | $\underset{SCNH-\underline{n}\text{-}Bu}{\overset{O}{\|}}$ |
| | 2,4-Cl—Ph | Me | Me | $\underset{SCNH-\underline{n}\text{-}Bu}{\overset{O}{\|}}$ |

TABLE III-continued

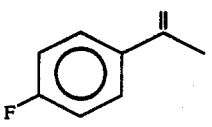

| Cmpd. No. | R₁ | R₂ | R₃ | Y |
|---|---|---|---|---|
| | 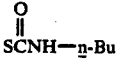 | 4-F—Ph | Me | $\underset{\text{SCNH—n-Bu}}{\overset{\text{O}}{\|}}$ |
| | 4-F—Ph | Ph | Me | $\underset{\text{SCNHPh}}{\overset{\text{O}}{\|}}$ |
| | Ph | Ph | Me | $\underset{\text{SCNHPh}}{\overset{\text{O}}{\|}}$ |
| | 4-Cl—Ph | 4-Cl—Ph | Me | $\underset{\text{SCNHPh}}{\overset{\text{O}}{\|}}$ |
| | 4-Cl—Ph | Ph | Me | $\underset{\text{SCNHPh}}{\overset{\text{O}}{\|}}$ |
| | 4-F—Ph | 2-F—Ph | Me | $\underset{\text{SCNHPh}}{\overset{\text{O}}{\|}}$ |
| | 4-F—Ph | 2,4-F₂—Ph | Me | $\underset{\text{SCNHPh}}{\overset{\text{O}}{\|}}$ |
| | 4-F—Ph | 4-F—Ph | vinyl | $\underset{\text{SCNHPh}}{\overset{\text{O}}{\|}}$ |
| | 4-F—Ph | 4-F—Ph | allyl | $\underset{\text{SCNHPh}}{\overset{\text{O}}{\|}}$ |
| | 4-Ph—Ph | Me | Me | $\underset{\text{SCNHPh}}{\overset{\text{O}}{\|}}$ |
| | 4-Ph—Ph | vinyl | vinyl | $\underset{\text{SCNHPh}}{\overset{\text{O}}{\|}}$ |
| | 4-F—Ph | 4-F—Ph | OH | $\underset{\text{SCNHPh}}{\overset{\text{O}}{\|}}$ |
| | 4-F—Ph | 4-F—Ph | O—t-Bu | $\underset{\text{SCNHPh}}{\overset{\text{O}}{\|}}$ |
| | 4-F—Ph | 4-F—Ph | Et | $\underset{\text{SCNHPh}}{\overset{\text{O}}{\|}}$ |
| | 2,4-Cl₂—Ph | Me | Me | $\underset{\text{SCNHPh}}{\overset{\text{O}}{\|}}$ |
| | 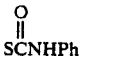 | 4-F—Ph | Me | $\underset{\text{SCNHPh}}{\overset{\text{O}}{\|}}$ |
| | 4-F—Ph | Ph | Me | F |
| | Ph | Ph | Me | F |
| | 4-Cl—Ph | 4-Cl—Ph | Me | F |
| | 4-Cl—Ph | Ph | Me | F |

TABLE III-continued $$R_2-\underset{\underset{R_3}{|}}{\overset{\underset{|}{R_1}}{Si}}-CH_2N\diagdown\underset{\underset{Y}{}}{\overset{}{N}}\diagup N$$

| Cmpd. No. | R₁ | R₂ | R₃ | Y |
|---|---|---|---|---|
| | 4-F—Ph | 2-F—Ph | Me | F |
| | 4-F—Ph | 2,4-F₂—Ph | Me | F |
| | 4-F—Ph | 4-F—Ph | vinyl | F |
| | 4-F—Ph | 4-F—Ph | allyl | F |
| | 4-Ph—Ph | Me | Me | F |
| | 4-Ph—Ph | vinyl | vinyl | F |
| | 4-F—Ph | 4-F—Ph | OH | F |
| | 4-F—Ph | 4-F—Ph | O—t-Bu | F |
| | 4-F—Ph | 4-F—Ph | Et | F |
| | 2,4-Cl₂—Ph | Me | Me | F |
| | 4-F-C₆H₄-C(=CH₂)- | 4-F—Ph | Me | F |
| | 4-F—Ph | Ph | Me | Cl |
| | Ph | Ph | Me | Cl |
| | 4-Cl—Ph | 4-Cl—Ph | Me | Cl |
| | 4-Cl—Ph | Ph | Me | Cl |
| | 4-F—Ph | 2-F—Ph | Me | Cl |
| | 4-F—Ph | 2,4-F₂—Ph | Me | Cl |
| | 4-F—Ph | 4-F—Ph | vinyl | Cl |
| | 4-F—Ph | 4-F—Ph | allyl | Cl |
| | 4-Ph—Ph | Me | Me | Cl |
| | 4-Ph—Ph | vinyl | vinyl | Cl |
| | 4-F—Ph | 4-F—Ph | OH | Cl |
| | 4-F—Ph | 4-F—Ph | O—t-Bu | Cl |
| | 4-F—Ph | 4-F—Ph | Et | Cl |
| | 2,4-Cl₂—Ph | Me | Me | Cl |
| | 4-F-C₆H₄-C(=CH₂)- | 4-F—Ph | Me | Cl |
| | 4-F—Ph | Ph | Me | CHO |
| | Ph | Ph | Me | CHO |
| | 4-Cl—Ph | 4-Cl—Ph | Me | CHO |
| | 4-Cl—Ph | Ph | Me | CHO |
| | 4-F—Ph | 2-F—Ph | Me | CHO |
| | 4-F—Ph | 2,4-F₂—Ph | Me | CHO |
| | 4-F—Ph | 4-F—Ph | vinyl | CHO |
| | 4-F—Ph | 4-F—Ph | allyl | CHO |
| | 4-Ph—Ph | Me | Me | CHO |
| | 4-Ph—Ph | vinyl | vinyl | CHO |
| | 4-F—Ph | 4-F—Ph | OH | CHO |
| | 4-F—Ph | 4-F—Ph | O—t-Bu | CHO |
| | 4-F—Ph | 4-F—Ph | Et | CHO |
| | 2,4-Cl₂—Ph | Me | Me | CHO |
| | 4-F-C₆H₄-C(=CH₂)- | 4-F—Ph | Me | CHO |
| | PhCH=CH— | CH₃ | CH₃ | SH |
| | 4-F—PhCH—CH— | 4-F—Ph | CH₃ | SH |
| | (CH₃)₂C=CH₂— | 2,4-F₂—Ph | CH₃ | SH |
| | CH₂=C(Et)= | 4-Cl—Ph | CH₃ | SH |
| | 1-naphthyl | 2-CF₃—Ph | CH₃ | SH |
| | 2-naphthyl | CH₃ | CH₃ | SH |
| | PhC≡C— | 4-F—Ph | 4-F—Ph | SH |
| | n-Buc≡C | 4-F—Ph | CH₃ | SH |
| | CH₃C≡C— | 4-F—Ph | 4-F—Ph | SH |
| | 4-Ph—Ph | CH₂CH=C(CH₃)₂ | O—t-Bu | SH |

TABLE III-continued

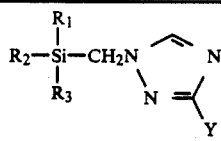

| Cmpd. No. | R₁ | R₂ | R₃ | Y |
|---|---|---|---|---|
| | 4-F—Ph | 3-CF₃—Ph | Me | SH |
| | 4-MeO—Ph | 4-Cl—Ph | n-Bu | SH |
| | 4-(4-F—Ph)pH | vinyl | O—t-Bu | SH |
| | 4-CHF₂O—Ph | Ph | Me | SH |
| | 4-Br—Ph | n-hexyl | Me | SH |
| | 4-Me—Ph | 4-Me—Ph | Me | SH |
| | 4-CF₃O—Ph | 4-CF₃O—Ph | Me | SH |
| | 4-(n-Bu)—Ph | 4-F—Ph | Me | SH |
| | 2,4-Cl₂—Ph | CH₂C(Me)=CH₂ | CH₂C(Me)=CH₂ | SH |
| | 4-F—Ph | 4-F—Ph | O—n-Bu | SH |
| | t-BuC≡C— | 4-F—Ph | Me | SH |
| | 2,6-MeO₂—Ph | Me | Me | SH |
| | 4-(t-Bu)—Ph | Me | Me | SH |
| | Ph-C(=CH₂)(CH₃)- (α-methylstyryl) | 4-F—Ph | Me | SH |
| | PhCH=CH— | CH₃ | CH₃ | —SS— |
| | 4-F—PhCH=CH— | 4-F—Ph | CH₃ | —SS— |
| | (CH₃)₂C=CH₂— | 2,4-F₂—Ph | CH₃ | —SS— |
| | CH₂=C(Et)— | 4-Cl—Ph | CH₃ | —SS— |
| | 1-naphthyl | 2-CF₃—Ph | CH₃ | —SS— |
| | 2-naphthyl | CH₃ | CH₃ | —SS— |
| | PhC≡C— | 4-F—Ph | 4-F—Ph | —SS— |
| | n-BuC≡C | 4-F—Ph | CH₃ | —SS— |
| | CH₃C≡C— | 4-F—Ph | 4-F—Ph | —SS— |
| | 4-Ph—Ph | CH₂CH=C(CH₃)₂ | O—t-Bu | —SS— |
| | 4-F—Ph | 3-CF₃—Ph | Me | —SS— |
| | 4-MeO—Ph | 4-Cl—Ph | n-Bu | —SS— |
| | 4-(4-F—Ph)—Ph | vinyl | O—t-Bu | —SS— |
| | 4-CHF₂O—Ph | Ph | Me | —SS— |
| | 4-Br—Ph | n-hexyl | Me | —SS— |
| | 4-Me—Ph | 4-Me—Ph | Me | —SS— |
| | 4-CF₃O—Ph | 4-CF₃O—Ph | Me | —SS— |
| | 4-(n-Bu)—Ph | 4-F—Ph | Me | —SS— |
| | 2,4-Cl₂—Ph | CH₂C(Me)=CH₂ | CH₂C(Me)=CH₂ | —SS— |
| | 4-F—Ph | 4-F—Ph | O—n-Bu | —SS— |
| | t-BuC≡C— | 4-F—Ph | Me | —SS— |
| | 2,6-MeO₂—Ph | Me | Me | —SS— |
| | 4-(t-Bu)—Ph | Me | Me | —SS— |
| | Ph-C(=CH₂)(CH₃)- (α-methylstyryl) | 4-F—Ph | Me | —SS— |
| | PhCH=CH— | CH₃ | CH₃ | SCNH—n-Bu (C=O) |
| | 4-F—PhCH=CH— | 4-F—Ph | CH₃ | SCNH—n-Bu (C=O) |
| | (CH₃)₂C=CH₂— | 2,4-F₂—Ph | CH₃ | SCNH—n-Bu (C=O) |
| | CH₂=C(Et)— | 4-Cl—Ph | CH₃ | SCNH—n-Bu (C=O) |
| | 1-naphthyl | 2-CF₃—Ph | CH₃ | SCNH—n-Bu (C=O) |

TABLE III-continued

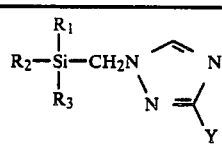

| Cmpd. No. | R₁ | R₂ | R₃ | Y |
|---|---|---|---|---|
| | 2-naphthyl | CH₃ | CH₃ | $\underset{\text{SCNH}-\underline{n}\text{-Bu}}{\overset{\overset{\displaystyle O}{\|}}{}}$ |
| | PhC≡C— | 4-F—Ph | 4-F—Ph | $\underset{\text{SCNH}-\underline{n}\text{-Bu}}{\overset{\overset{\displaystyle O}{\|}}{}}$ |
| | BuC≡C | 4-F—Ph | CH₃ | $\underset{\text{SCNH}-\underline{n}\text{-Bu}}{\overset{\overset{\displaystyle O}{\|}}{}}$ |
| | CH₃C≡C— | 4-F—Ph | 4-F—Ph | $\underset{\text{SCNH}-\underline{n}\text{-Bu}}{\overset{\overset{\displaystyle O}{\|}}{}}$ |
| | 4-Ph—Ph | CH₂CH=C(CH₃)₂ | O—t-Bu | $\underset{\text{SCNH}-\underline{n}\text{-Bu}}{\overset{\overset{\displaystyle O}{\|}}{}}$ |
| | 4-F—Ph | 3-CF₃—Ph | Me | $\underset{\text{SCNH}-\underline{n}\text{-Bu}}{\overset{\overset{\displaystyle O}{\|}}{}}$ |
| | 4-MeO—Ph | 4-Cl—Ph | n-Bu | $\underset{\text{SCNH}-\underline{n}\text{-Bu}}{\overset{\overset{\displaystyle O}{\|}}{}}$ |
| | 4-(4-F—Ph)—Ph | vinyl | O—t-Bu | $\underset{\text{SCNH}-\underline{n}\text{-Bu}}{\overset{\overset{\displaystyle O}{\|}}{}}$ |
| | 4-CHF₂O—Ph | Ph | Me | $\underset{\text{SCNH}-\underline{n}\text{-Bu}}{\overset{\overset{\displaystyle O}{\|}}{}}$ |
| | 4-Br—Ph | n-hexyl | Me | $\underset{\text{SCNH}-\underline{n}\text{-Bu}}{\overset{\overset{\displaystyle O}{\|}}{}}$ |
| | 4-Me—Ph | 4-Me—Ph | Me | $\underset{\text{SCNH}-\underline{n}\text{-Bu}}{\overset{\overset{\displaystyle O}{\|}}{}}$ |
| | 4-CF₃O—Ph | 4-CF₃O—Ph | Me | $\underset{\text{SCNH}-\underline{n}\text{-Bu}}{\overset{\overset{\displaystyle O}{\|}}{}}$ |
| | 4-(n-Bu)—Ph | 4-F—Ph | Me | $\underset{\text{SCNH}-\underline{n}\text{-Bu}}{\overset{\overset{\displaystyle O}{\|}}{}}$ |
| | 2,4-Cl₂—Ph | CH₂C(Me)=CH₂ | CH₂C(Me)=CH₂ | $\underset{\text{SCNH}-\underline{n}\text{-Bu}}{\overset{\overset{\displaystyle O}{\|}}{}}$ |
| | 4-F—Ph | 4-F—Ph | O—n-Bu | $\underset{\text{SCNH}-\underline{n}\text{-Bu}}{\overset{\overset{\displaystyle O}{\|}}{}}$ |
| | t-BuC≡C— | 4-F—Ph | Me | $\underset{\text{SCNH}-\underline{n}\text{-Bu}}{\overset{\overset{\displaystyle O}{\|}}{}}$ |
| | 2,6-MeO₂—Ph | Me | Me | $\underset{\text{SCNH}-\underline{n}\text{-Bu}}{\overset{\overset{\displaystyle O}{\|}}{}}$ |

TABLE III-continued

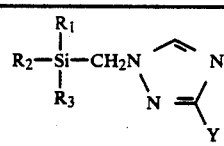

| Cmpd. No. | R₁ | R₂ | R₃ | Y |
|---|---|---|---|---|
| | 4-(t-Bu)—Ph | Me | Me | $\underset{\text{SCNH}-\underline{n}\text{-Bu}}{\overset{\text{O}}{\parallel}}$ |
| | 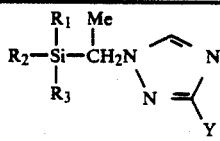 | 4-F—Ph | Me | $\underset{\text{SCNH}-\underline{n}\text{-Bu}}{\overset{\text{O}}{\parallel}}$ |

Footnotes to Table III
NMR Data (CDCl₃): peak position in parts per million downfield from tetramethylsilane.
1. 0.7 (s), 4.1 (s), 7.1 (m), 7.4 (m), 7.7 (s).
2. 0.7 (s), 2.5 (s), 4.1 (s), 7.1 (m), 7.5 (m), 7.7 (s).
3. 0.7 (s), 4.2 (s), 4.6 (s), 7.1 (m), 7.4 (m), 7.8 (s).
4. 0.7 (s), 4.3 (s), 4.4 (s), 7.1 (m), 7.5 (m), 7.9 (s).

TABLE IV

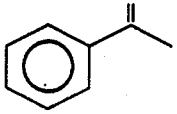

| Cmpd. No. | R₁ | R₂ | R₃ | Y |
|---|---|---|---|---|
| | 4-F—Ph | 4-F—Ph | Me | F |
| | 4-F—Ph | 4-F—Ph | Me | Cl |
| | 4-F—Ph | 4-F—Ph | Me | I |
| | 4-F—Ph | 4-F—Ph | Me | NH₂ |
| | 4-F—Ph | 4-F—Ph | Me | SH |
| | 4-F—Ph | 4-F—Ph | Me | —SS— |
| | 4-F—Ph | 4-F—Ph | Me | SMe |
| | 4-F—Ph | 4-F—Ph | Me | S(O)Me |
| | 4-F—Ph | 4-F—Ph | Me | SO₂Me |
| | 4-F—Ph | 4-F—Ph | Me | SCH₂SCN |
| | 4-F—Ph | 4-F—Ph | Me | S(O)CH₂SCN |
| | 4-F—Ph | 4-F—Ph | Me | SO₂CH₂SCN |
| | 4-F—Ph | 4-F—Ph | Me | SCH₂CN |
| | 4-F—Ph | 4-F—Ph | Me | S(O)CH₂CN |
| | 4-F—Ph | 4-F—Ph | Me | SO₂CH₂CN |
| | 4-F—Ph | 4-F—Ph | Me | SSMe |
| | 4-F—Ph | 4-F—Ph | Me | $\underset{\text{SCNH}_2}{\overset{\text{O}}{\parallel}}$ |
| | 4-F—Ph | 4-F—Ph | Me | $\underset{\text{SCNHMe}}{\overset{\text{O}}{\parallel}}$ |
| | 4-F—Ph | 4-F—Ph | Me | $\underset{\text{SCNH}-\underline{n}\text{-Bu}}{\overset{\text{O}}{\parallel}}$ |
| | 4-F—Ph | 4-F—Ph | Me | $\underset{\text{SCNH}-\underline{i}\text{-Pr}}{\overset{\text{O}}{\parallel}}$ |
| | 4-F—Ph | 4-F—Ph | Me | $\underset{\text{SCNHCH}_2\text{CH}=\text{CH}_2}{\overset{\text{O}}{\parallel}}$ |
| | 4-F—Ph | 4-F—Ph | Me | $\underset{\text{SCNHPh}}{\overset{\text{O}}{\parallel}}$ |

TABLE IV-continued

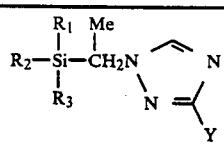

| Cmpd. No. | R₁ | R₂ | R₃ | Y |
|---|---|---|---|---|
| | 4-F—Ph | 4-F—Ph | Me | $\overset{S}{\underset{\|}{SCNH-\text{n-Bu}}}$ |
| | 4-F—Ph | 4-F—Ph | Me | $\overset{S}{\underset{\|}{SCNHPh}}$ |
| | 4-F—Ph | 4-F—Ph | Me | CHO |
| | 4-F—Ph | 4-F—Ph | Me | CO₂Me |
| | 4-F—Ph | Ph | Me | SH |
| | Ph | Ph | Me | SH |
| | 4-Cl—Ph | 4-Cl—Ph | Me | SH |
| | 4-Cl—Ph | Ph | Me | SH |
| | 4-F—Ph | 2-F—Ph | Me | SH |
| | 4-F—Ph | 2,4-F₂—Ph | Me | SH |
| | 4-F—Ph | 4-F—Ph | vinyl | SH |
| | 4-F—Ph | 4-F—Ph | allyl | SH |
| | 4-Ph—Ph | vinyl | vinyl | SH |
| | 4-F—Ph | 4-F—Ph | OH | SH |
| | 4-F—Ph | 4-F—Ph | O—t-Bu | SH |
| | 4-F—Ph | 4-F—Ph | Et | SH |
| | 2,4-Cl₂—Ph | Me | Me | SH |
| | 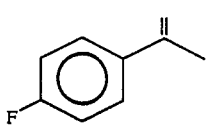 | 4-F—Ph | Me | SH |
| | 4-F—Ph | Ph | Me | —SS— |
| | Ph | PH | Me | —SS— |
| | 4-Cl—Ph | 4-Cl—Ph | Me | —SS— |
| | 4-Cl—Ph | Ph | Me | —SS— |
| | 4-F—Ph | 2-F—Ph | Me | —SS— |
| | 4-F—Ph | 2,4-F₂—Ph | Me | —SS— |
| | 4-F—Ph | 4-F—Ph | vinyl | —SS— |
| | 4-F—Ph | 4-F—Ph | allyl | —SS— |
| | 4-Ph—Ph | vinyl | vinyl | —SS— |
| | 4-F—Ph | 4-F—Ph | OH | —SS— |
| | 4-F—Ph | 4-F—Ph | O—t-Bu | —SS— |
| | 4-F—Ph | 4-F—Ph | Et | —SS— |
| | 2,4-Cl₂—Ph | Me | Me | —SS— |
| | 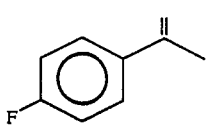 | 4-F—Ph | Me | —SS— |
| | 4-F—Ph | Ph | Me | SSMe |
| | Ph | Ph | Me | SSMe |
| | 4-Cl—Ph | 4-Cl—Ph | Me | SSMe |
| | 4-Cl—Ph | Ph | Me | SSMe |
| | 4-F—Ph | 2-F—Ph | Me | SSMe |
| | 4-F—Ph | 2,4-F₂—Ph | Me | SSMe |
| | 4-F—Ph | 4-F—Ph | vinyl | SSMe |
| | 4-F—Ph | 4-F—Ph | allyl | SSMe |
| | 4-Ph—Ph | vinyl | vinyl | SSMe |
| | 4-F—Ph | 4-F—Ph | OH | SSMe |
| | 4-F—Ph | 4-F—Ph | O—t-Bu | SSMe |
| | 4-F—Ph | 4-F—Ph | Et | SSMe |
| | 2,4-Cl₂—Ph | Me | Me | SSMe |
| | 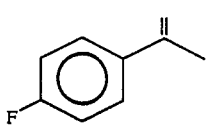 | 4-F—Ph | Me | SSMe |

TABLE IV-continued $$\begin{array}{c} R_1 \quad Me \\ R_2-Si-CH_2N \\ R_3 \end{array}$$ (triazole with Y)

| Cmpd. No. | R₁ | R₂ | R₃ | Y |
|---|---|---|---|---|
| | 4-F—Ph | Ph | Me | SCNH—n-Bu (C=O) |
| | Ph | Ph | Me | SCNH—n-Bu (C=O) |
| | 4-Cl—Ph | 4-Cl—Ph | Me | SCNH—n-Bu (C=O) |
| | 4-Cl—Ph | Ph | Me | SCNH—n-Bu (C=O) |
| | 4-F—Ph | 2-F—Ph | Me | SCNH—n-Bu (C=O) |
| | 4-F—Ph | 2,4-F₂—Ph | Me | SCNH—n-Bu (C=O) |
| | 4-F—Ph | 4-F—Ph | vinyl | SCNH—n-Bu (C=O) |
| | 4-F—Ph | 4-F—Ph | allyl | SCNH—n-Bu (C=O) |
| | 4-Ph—Ph | Me | Me | SCNH—n-Bu (C=O) |
| | 4-Ph—Ph | vinyl | vinyl | SCNH—n-Bu (C=O) |
| | 4-F—Ph | 4-F—Ph | OH | SCNH—n-Bu (C=O) |
| | 4-F—Ph | 4-F—Ph | O—t-Bu | SCNH—n-Bu (C=O) |
| | 4-F—Ph | 4-F—Ph | Et | SCNH—n-Bu (C=O) |
| | 2,4-Cl₂—Ph | Me | Me | SCNH—n-Bu (C=O) |
| | CH₂=C(4-F-C₆H₄)— | 4-F—Ph | Me | SCNH—n-Bu (C=O) |
| | 4-F—Ph | Ph | Me | CHO |
| | Ph | Ph | Me | CHO |
| | 4-Cl—Ph | 4-Cl—Ph | Me | CHO |
| | 4-Cl—Ph | Ph | Me | CHO |
| | 4-F—Ph | 2-F—Ph | Me | CHO |
| | 4-F—Ph | 2,4-F₂—Ph | Me | CHO |

TABLE IV-continued $$R_2-\underset{\underset{R_3}{|}}{\overset{\overset{R_1}{|}}{Si}}-\underset{}{\overset{\overset{Me}{|}}{CH_2N}} \diagdown\text{(imidazole ring with Y)}$$

| Cmpd. No. | $R_1$ | $R_2$ | $R_3$ | Y |
|---|---|---|---|---|
| | 4-F—Ph | 4-F—Ph | vinyl | CHO |
| | 4-F—Ph | 4-F—Ph | allyl | CHO |
| | 4-Ph—Ph | vinyl | vinyl | CHO |
| | 4-F—Ph | 4-F—Ph | OH | CHO |
| | 4-F—Ph | 4-F—Ph | O—t-Bu | CHO |
| | 4-F—Ph | 4-F—Ph | Et | CHO |
| | 2,4-Cl$_2$—Ph | Me | Me | CHO |
| | α-methylstyryl | 4-F—Ph | Me | CHO |

TABLE V $$R_2-\underset{\underset{R_3}{|}}{\overset{\overset{R_1}{|}}{Si}}-CH_2N \diagdown\text{(imidazole ring with X)}$$

| Cmpd. No. | $R_1$ | $R_2$ | $R_3$ | X | |
|---|---|---|---|---|---|
| 97. | 4-F—Ph | 4-F—Ph | Me | I | oil[1] |
| 98. | 4-F—Ph | 4-F—Ph | Me | SH | m.p. 130–139° |
| | 4-F—Ph | 4-F—Ph | Me | —SS— | |
| 99. | 4-F—Ph | 4-F—Ph | Me | SO$_2$OH | m.p. 208–218° |
| | 4-F—Ph | 4-F—Ph | Me | SEt | |
| | 4-F—Ph | 4-F—Ph | Me | SPr | |
| | 4-F—Ph | 4-F—Ph | Me | S—i-Pr | |
| | 4-F—Ph | 4-F—Ph | Me | SBu | |
| | 4-F—Ph | 4-F—Ph | Me | SCH$_2$CHMe$_2$ | |
| | 4-F—Ph | 4-F—Ph | Me | SCH(Me)Et | |
| | 4-F—Ph | 4-F—Ph | Me | SCMe$_3$ | |
| | 4-F—Ph | 4-F—Ph | Me | SCH$_2$CN | |
| | 4-F—Ph | 4-F—Ph | Me | SCH$_2$SCN | |
| | 4-F—Ph | 4-F—Ph | Me | S(O)Et | |
| | 4-F—Ph | 4-F—Ph | Me | S(O)Pr | |
| | 4-F—Ph | 4-F—Ph | Me | S(O)—i-Pr | |
| | 4-F—Ph | 4-F—Ph | Me | S(O)Bu | |
| | 4-F—Ph | 4-F—Ph | Me | S(O)CH$_2$CHMe$_2$ | |
| | 4-F—Ph | 4-F—Ph | Me | S(O)CH(Me)Et | |
| | 4-F—Ph | 4-F—Ph | Me | S(O)CMe$_3$ | |
| | 4-F—Ph | 4-F—Ph | Me | S(O)CH$_2$CN | |
| | 4-F—Ph | 4-F—Ph | Me | S(O)CH$_2$SCN | |
| | 4-F—Ph | 4-F—Ph | Me | SO$_2$Et | |
| | 4-F—Ph | 4-F—Ph | Me | SO$_2$Pr | |
| | 4-F—Ph | 4-F—Ph | Me | SO$_2$—i-Pr | |
| | 4-F—Ph | 4-F—Ph | Me | SO$_2$Bu | |
| | 4-F—Ph | 4-F—Ph | Me | SO$_2$CH$_2$CHMe$_2$ | |
| | 4-F—Ph | 4-F—Ph | Me | SO$_2$CH(Me)Et | |
| | 4-F—Ph | 4-F—Ph | Me | SO$_2$CMe$_3$ | |
| | 4-F—Ph | 4-F—Ph | Me | SO$_2$CH$_2$CN | |
| | 4-F—Ph | 4-F—Ph | Me | SO$_2$CH$_2$SCN | |
| | 4-F—Ph | Ph | Me | I | |
| | Ph | Ph | Me | I | |
| | 4-Cl—Ph | 4-Cl—Ph | Me | I | |
| | 4-Cl—Ph | Ph | Me | I | |
| | 4-F—Ph | 2-F—Ph | Me | I | |
| | 4-F—Ph | 2,4-F$_2$—Ph | Me | I | |
| | 4-F—Ph | 4-F—Ph | vinyl | I | |
| | 4-F—Ph | 4-F—Ph | allyl | I | |
| | 4-Ph—Ph | Me | Me | I | |
| | 4-Ph—Ph | vinyl | vinyl | I | |
| | 4-F—Ph | 4-F—Ph | OH | I | |
| | 4-F—Ph | 4-F—Ph | O—t-Bu | I | |
| | 4-F—Ph | 4-F—Ph | Et | I | |
| | 2,4-Cl$_2$—Ph | Me | Me | I | |

TABLE V-continued

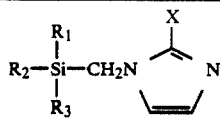

| Cmpd. No. | R₁ | R₂ | R₃ | X |
|---|---|---|---|---|
| | 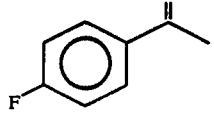 | 4-F—Ph | Me | I |
| | 4-F—Ph | Ph | Me | SH |
| | Ph | Ph | Me | SH |
| | 4-Cl—Ph | 4-Cl—Ph | Me | SH |
| | 4-Cl—Ph | Ph | Me | SH |
| | 4-F—Ph | 2-F—Ph | Me | SH |
| | 4-F—Ph | 2,4-F₂—Ph | Me | SH |
| | 4-F—Ph | 4-F—Ph | vinyl | SH |
| | 4-F—Ph | 4-F—Ph | allyl | SH |
| | 4-Ph—Ph | Me | Me | SH |
| | 4-Ph—Ph | vinyl | vinyl | SH |
| | 4-F—Ph | 4-F—Ph | OH | SH |
| | 4-F—Ph | 4-F—Ph | O—t-Bu | SH |
| | 4-F—Ph | 4-F—Ph | Et | SH |
| | 2,4-Cl—Ph | Me | Me | SH |
| | 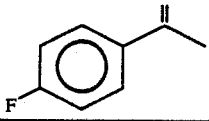 | 4-F—Ph | Me | SH |

Footnotes to Table V
NMR Data (CDCl₃): peak position in parts per million downfield from tetramethylsilane.
¹0.6 (s), 4.0 (s), 6.6 (s), 7.0 (s), 7.1 (m), 7.4 (m).

Utility

The compounds of this invention are useful as plant disease control agents. They are effective in controlling a broad spectrum of plant diseases, particularly foliar pathogens of ornamental, vegetable, field, cereal and fruit crops, such as, *Puccinia recondita, Sphaerotheca fuliginea, Erysiphe graminis, Podosphaera leucotricha, Venturia inaequalis, Pyricularia oryzae, Bipolaris oryzae, Cercospora arachidicola, Cercospora beticola* and *Monilinia fructicola.* They also control soil borne pathogens such as *Rhizoctonia solani.*

Formulation

The compounds of this invention will generally be used in formulations with a liquid or solid diluent or with an organic solvent. Useful formulations of the compounds of Formula I can be prepared in conventional ways. They include dusts, granules, pellets, solutions, emulsions, wettable powders, emulsifiable concentrates and the like. Many of these may be applied directly. Sprayable formulations may be extended in suitable media and used at spray volumes of from about one to several hundred liters per hectare. High strength compositions are primarily used as intermediates for further formulation. The formulations, broadly, contain about 1% to 99% by weight of active ingredient(s) and at least one of (a) about 0.1% to 35% surfactant(s) and (b) about 5% to 99% solid or liquid inert diluent(s). More specifically, they will contain these ingredients in the following approximate proportions:

| | Active Ingredient | Percent by Weight | |
|---|---|---|---|
| | | Diluent(s) | Surfactant(s) |
| Wettable Powders | 20-90 | 0-74 | 1-10 |
| Oil Suspensions, Emulsions, Solutions, (including Emulsifiable Concentrates) | 5-50 | 40-95 | 0-35 |
| Aqueous Suspensions | 10-50 | 40-84 | 1-20 |
| Dusts | 1-25 | 70-99 | 0-5 |
| Granules and Pellets | 1-95 | 5-99 | 0-15 |
| High Strength Compositions | 90-99 | 0-10 | 0-2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for the wettable powders and the denser ones for dusts. Typical liquid diluents and solvents are described in Marsden, "Solvents Guide," 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 4th Edn., McGraw-Hill, N.Y., 1963, pp. 8–59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, Mar. 14, 1967, Col. 5, Line 43 through Col. 7, Line 62 and Examples 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3, Line 66 through Col. 5, Line 17 and Examples 1–4.

G. C. Klingman, "Weed Control as a Science", John Wiley and Sons, Inc., New York, 1961, pp. 81–96.

J. D. Fryer and S. A. Evans, "Weed Control Handbook", 5th Edn. Blackwell Scientific Publications, Oxford, 1968, pp. 101–103.

Examples of useful formulations of compounds of the present invention are as follows.

EXAMPLE 16

Wettable Powder

| | |
|---|---|
| 1-[bis(4-fluorophenyl)(methyl)silylmethyl]-1H—1,2,4-triazole-5-thiol | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled, re-blended and packaged.

EXAMPLE 17

High Strength Concentrate

| | |
|---|---|
| 1-[bis(4-fluorophenyl)(methyl)silylmethyl]-5-iodo-1H—1,2,4-triazole | 98.5% |
| silica aerogel | 0.5% |
| synthetic amorphous fine silica | 1.0% |

The ingredients are blended and ground in a hammermill to produce a high strength concentrate essentially all passing a U.S.S. No. 50 sieve (0.3 mm openings). This material may then be formulated in a variety of ways.

EXAMPLE 18

Aqueous Suspension

| | |
|---|---|
| 1-[bis(4-fluorophenyl)(methyl)silylmethyl]-1H—1,2,4-triazole-5-thiol | 25% |
| hydrated attapulgite | 3% |
| crude calcium ligninsulfonate | 10% |
| sodium dihydrogen phosphate | 0.5% |
| water | 61.5% |

The ingredients are ground together in a ball, sand, or roller mill until the solid particles have been reduced to diameters under 10 microns.

EXAMPLE 19

Solution

| | |
|---|---|
| 1-[bis(4-fluorophenyl)(methyl)silylmethyl]-2-iodo-1H—imidazole | 30% |
| dimethylformamide | 70% |

The ingredients are combined and stirred to produce a solution, which can be used for low volume applications.

EXAMPLE 20

Emulsifiable Concentrate

| | |
|---|---|
| 1-[bis(4-fluorophenyl)(methyl)silylmethyl]-5-(cyanomethylsulfonyl)-1H—1,2,4-triazole | 15% |
| blend of calcium sulfonates and nonionic surfactants | 25% |
| xylene | 60% |

The ingredients are combined and stirred until the active is dissolved. A fine screen filter is included in packaging operation to insure the absence of any extraneous undissolved material in the product.

EXAMPLE 21

Granule

| | |
|---|---|
| wettable powder of Example 16 | 15% |
| gypsum | 69% |
| potassium sulfate | 16% |

The ingredients are blended in a rotating or fluid bed mixer and water sprayed on to accomplish granulation. When most of the material has reached the desired range of 1.0 to 0.42 mm. (U.S.S. No. 18 to 40 sieves), the granules are removed, dried, and screened. Oversize material is crushed to produce additional material in the desired range.

The compounds of this invention can be mixed with fungicides, bactericides, acaricides, nematicides, insecticides, or other biologically active compounds in order to achieve desired results with a minimum expenditure of time, effort and material. Amounts of these biologically active materials added for each part by weight of the composition of this invention may vary from 0.05 to 45 parts by weight. Suitable agents of this type are well-known to those skilled in the art. Some are listed below:

Fungicides:
methyl 2-benzimidazolecarbamate (carbendazim)

tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
2-cyano-N-ethylcarbamoyl-2-methoxyiminoacetamide (cymoxanil)
N-trichloromethylthiotetrahydrophthalimide (captan)
N-trichloromethylthiophthalimide (folpet)
dimethyl(4,4'-o-phenylene)bis(3-thioallophanate) (thiophanate-methyl)
2-(thiazol-4-yl)benzimidazole (thiabendazole)
aluminum tris(O-ethyl phosphonate) ("Aliette")
tetrachloroisophthalonitrile (chlorothalonil)
2,6-dichloro-4-nitroaniline (dichloran)
N-(2,6-dimethylphenyl)-N-(methoxyacetyl)alanine methyl ester (metalaxyl)
cis-N-[(1,1,2,2-tetrachloroethyl)thio]-4-cyclohexene-1,2-dicarbioximide (captafol)
3-(3,5-dichlorophenyl)-N-(1-methyl-ethyl)-2,4-dioxo-1-imidazolidine carboxamide (iprodione)
3-(3,5-dichlorophenyl)-5-ethenyl-5-methyl-2,4-oxazolidinedione (vinclozolin)
2,6-dimethyl-4-tridecylmorpholine (tridemorph)
kasugamycin
O-ethyl S,S-diphenyl phosphorodithioate (edifenphos)
Bactericides:
tribasic copper sulfate
streptomycin sulfate
oxytetracycline
Acaricides:
senecioic acid, ester with 2-sec-butyl-4,6-dinitrophenol (binapacryl)
6-methyl-1,3-dithiolo[2,3-β]quinonolin-2-one (oxythioquinox)
2,2,2-trichloro-1,1-bis(4-chlorophenyl)ethanol (dicofol)
bis(pentachloro-2,4-cyclopentadien-1-yl) (dienochlor)
tricyclohexyltin hydroxide (cyhexatin)
hexakis(2-methyl-2-phenylpropyl)distannoxane (fenbutin oxide)
Nematicides:
2-[diethoxyphosphinylimino]-1,3-dithietane (fosthietan)
S-methyl-1-(dimethylcarbamoyl)-N-(methylcarbamoyloxy)thioformimidate (oxamyl)
S-methyl-1-carbamoyl-N-(methylcarbamoyloxy)thioformimidate
N-isopropylphosphoramidic acid, O-ethyl-O'-[4-(methylthio)-m-tolyl]diester (fenamiphos)
Insecticides:
3-hydroxy-N-methylcrotonamide(dimethylphosphate)ester (monocrotophos)
methylcarbamic acid, ester with 2,3-dihydro-2,2-dimethyl-7-benzofuranol (carbofuran)
O-[2,4,5-trichloro-α-(chloromethyl)benzyl]phosphoric acid, O',O'-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-p-nitrophenyl ester (methyl parathion)
methylcarbamic acid, ester with α-naphthol (carbaryl)
methyl N-[[(methylamino)carbonyl]oxy]ethanimidothioate (methomyl)
N'-(4-chloro-o-tolyl)-N,N-dimethylformamidine (chlordimeform)
O,O-diethyl-O-(2-isopropyl-4-methyl-6-pyrimidyl)-phosphorothioate (diazinon)
octachlorocamphene (toxaphene)
O-ethyl O-p-nitrophenyl phenylphosphonothioate (EPN)
cyano(3-phenoxyphenyl)-methyl 4-chloro-α-(1-methylethyl)benzeneacetate (fenvalerate)
(3-phenoxyphenyl)methyl (±)-cis,trans-3-(2,2-dichloroethenyl)-2,2-dimethylcyclopropanecarboxylate (permethrin)
dimethyl N,N'-[thiobis][(N-methylimino)carbonyloxy]]-bis[ethanimidothioate] (thiodicarb)
phosphorothiolothionic acid, O-ethyl-O-[4-(methylthio)phenyl]-S-n-propyl ester (sulprofos)
α-cyano-3-phenoxybenzyl 3-(2,2-dichlorovinyl)-2,2-dimethylcyclopropane carboxylate (cypermethrin)
cyano(3-phenoxyphenyl)methyl 4-(difluoromethoxy)-α-(methylethyl)benzeneacetate ("Payoff")
O,O-diethyl-O-(3,5,6-trichloro-2-pyridyl)phosphorothioate (chlorpyrifos)
O,O-dimethyl-S-[(4-oxo-1,2,3-benzotriazin-3-(4H)-yl)methyl]phosphorodithioate (azinphos-methyl)
5,6-dimethyl-2-dimethylamino-4-pyrimidinyl dimethyl carbamate ("Pirimor")
S-(N-formyl-N-methylcarbamoylmethyl-O,O-dimethyl phosphorodithioate (formothion)
S-2-(ethylthioethyl)-O,O-dimethyl phosphiorothioate (demeton-S-methyl)
α-cyano-3-phenoxybenzyl cis-3-(2,2-dibromovinyl)-2,2-dimethylcyclopropane carboxylate (deltamethrin)
cyano(3-phenoxyphenyl)methyl ester of N-(2-chloro-4-trifluoromethylphenyl)alanine (fluvalinate)
trans-5-(4-chlorophenyl)-N-cyclohexyl-4-methyl-2-oxothiazolidine-3-carboxamide (hexythiazox)

Application

Disease control is ordinarily accomplished by applying an effective amount of the compound, normally as part of a formulation containing it, either pre- or post-infection to the portion of the plant to be protected, such as the roots, stems, foliage, fruit, seeds, tubers or bulbs, or to the medium (soil or sand) in which the plants to be protected are growing. The compound may also be applied to the seed from which the plants to be protected are to be grown.

Rates of application for these compounds can be influenced by many factors of the environment and should be determined under actual use conditions. Nevertheless, foliage can normally be protected when treated at a rate of from 1 gram or less up to 5000 grams of active ingredient per hectare. Plants growing in soil that is treated at a concentration from about 0.1 to about 20 kg of active ingredient per hectare can be protected from disease. Seed and seedlings can normally be protected when seed is treated at a rate of from about 0.06 to about 3 grams of active ingredient per kilogram of seed.

In the following Examples 22–34, the percent disease control is determined as the percent growth inhibition of colonies on treated plants as compared to untreated plants. Results for Examples 22–34 are given in Table VI. In the table, a rating of 100 indicates 100% disease control and a rating of 0 indicates no disease control relative to the controls. A "-" entry indicates that no test was performed with the specified compound. The number of the test compound corresponds to the similarly numbered compound in Tables I–V.

EXAMPLE 22

The test compounds were dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on apple seedlings. The following day plants were inoculated with a spore suspension of *Venturia inaequalis*, the causal agent of apple scab, and incubated in a saturated humidity chamber at 20° C. for 24 hours and then in a growth chamber at 22° C. for 11 days, when disease ratings were made.

EXAMPLE 23

The test compounds were dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on peanut seedlings. The following day plants were inoculated with a spore suspension of *Cercosporidium personatum*, the causal agent of Peanut Late Leafspot, and incubated in a saturated humidity chamber at 22° C. for 24 hours and then in a high humidity chamber at 27° C. for 7 days, and then in a growth chamber at 29° C. for 7 days, when disease ratings were made.

EXAMPLE 24

The test compounds were dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on broad bean seedlings. The following day plants were inoculated with a spore suspension of *Botrytis cinerea*, the causal agent of bean grey mold, and incubated in a saturated humidity chamber at 20° C. for 24 hours when disease ratings were made.

EXAMPLE 25

The test compounds were dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on wheat seedlings. The following day plants were inoculated with a spore dust of *Erysiphe graminis* f. sp. tritici, the causal agent of wheat powdery mildew, and incubated in a saturated humidity chamber at 20° C. for 6 days when disease ratings were made.

EXAMPLE 26

The test compounds were dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on rice seedlings. The following day plants were inoculated with a spore suspension of *Pyricularia oryzae*, the causal agent of rice blast, and incubated in a saturated humidity chamber at 27° C. for 24 hours and then in a growth chamber at 29° C. for 4 days, when disease ratings were made.

EXAMPLE 27

The test compounds were dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on rice seedlings. The following day plants were inoculated with a spore suspension of *Rhizoctonia solani*, the causal agent of rice sheath blight, and incubated in a saturated humidity chamber at 27° C. for 48 hours and then in a growth chamber at 29° C. for 4 days, when disease ratings were made.

EXAMPLE 28

The test compounds were dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on wheat seedlings. The following day plants were inoculated with a spore suspension of *Puccinia recondita*, the causal agent of wheat leaf rust, and incubated in a saturated humidity chamber at 20° C. for 24 hours and then in a growth chamber at 20° C. for 8 days, when disease ratings were made.

EXAMPLE 29

The test compounds were dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on tomato seedlings. The following day plants were inoculated with a spore suspension of *Phytophthora infestans*, the causal agent of tomato late blight, and incubated in a saturated humidity chamber at 20° C. for 24 hours and then in a growth chamber at 20° C. for 5 days, when disease ratings were made.

EXAMPLE 30

The test compounds were dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on grape seedlings. The following day plants were inoculated with a spore suspension of *Plasmorpara viticola*, the causal agent of grape downy mildew, and incubated in a saturated humidity chamber at 20° C. for 24 hours and then in a growth chamber at 20° C. for 7 days and then held in a saturated humidity chamber at 20° C. for 24 hours, when disease ratings were made.

EXAMPLE 31

The test compounds were dissolved in acetone so that 1 ml of solution yielded a concentration of 0.5 kilogram/hectare when added to cucumber seeds and soil in pots. Seeds and soil were then inoculated with a mixture of sand, cereal and mycelium of the fungus *Pythium aphanadermatum*, causal agent of cucumber damping off, and incubated in a growth chamber at 30° C. for 14 days. Disease ratings were then made.

EXAMPLE 32

The test compounds were dissolved in acetone so that 1 ml of solution yielded a concentration of 0.5 kilogram/hectare when added to cotton seeds and soil in pots. Seeds and soil were then inoculated with a mixture of sand, cereal and mycelium of the fungus *Rhizoctonia solani*, causal agent of cotton blight, and incubated in a growth chamber at 30° C. for 14 days. Disease ratings were then made.

EXAMPLE 33

The test compounds were dissolved in acetone so that 1 ml of solution yielded a concentration of 0.5 kilogram/hectare when added to cucumber seeds and soil in pots. Seeds and soil were then inoculated with a mixture of sand, cereal and mycelium of the fungus *Fusarium oxysporum* f. sp. *cucumerinum*, causal agent of cucumber wilt, and incubated in a growth chamber at 30° C. for 14 days. Disease ratings were then made.

EXAMPLE 34

The test compounds were dissolved in acetone so that 1 ml of solution yielded a concentration of 0.5 kilogram/hectare when added to lima bean seeds and soil in pots. Seeds and soil were then inoculated with a mixture of sand, cereal and mycelium of the fungus *Sclerotium rolfsii*, causal agent of southern blight, and incubated in a growth chamber at 30° C. for 14 days. Disease ratings were then made.

TABLE VI

PLANT DISEASE CONTROL DATA

| Cmpd No. | EX. 22 | EX. 23 | EX. 24 | EX. 25 | EX. 26 | EX. 27 | EX. 28 | EX. 29 | EX. 30 | EX. 31 | EX. 32 | EX. 33 | EX. 34 |
|---|---|---|---|---|---|---|---|---|---|---|---|---|---|
| 30 | 100 | 89 | 43 | 84 | 0 | 0 | 38 | 0 | 0 | 0 | 0 | 0 | 0 |
| 5 | 90 | 95 | 90 | 61 | 0 | 0 | 46 | 0 | 98 | 0 | 0 | 50 | 0 |
| 46 | 41 | 53 | 93 | 86 | 2 | 0 | 48 | 26 | 77 | 0 | 0 | 0 | 0 |
| 90 | 0 | 92 | 90 | 55 | 51 | 0 | 0 | 0 | 0 | 0 | 0 | 0 | 0 |
| 45 | 77 | 75 | 38 | 94 | 20 | 0 | 0 | 0 | 92 | 0 | 0 | 0 | 0 |
| 91 | 77 | 0 | 86 | 84 | 0 | 0 | 0 | 0 | 59 | 0 | 0 | 0 | 0 |
| 8 | 80 | 0 | 80 | — | 0 | 0 | 100 | 0 | — | — | — | — | — |
| 9 | 100 | — | 0 | — | 80 | 90 | 100 | 0 | — | — | — | — | — |
| 10 | 100 | — | 0 | — | 80 | 0 | 90 | 0 | — | — | — | — | — |
| 12 | — | 95 | 41 | 100 | 28 | 0 | 47 | 0 | 0 | 0 | 0 | 0 | 0 |
| 15 | — | 75 | 0 | 93 | 0 | 0 | 0 | 0 | — | 0 | 0 | 0 | 0 |
| 13 | — | 73 | 56 | 100 | 36 | 0 | 11 | 81 | 37 | 0 | 0 | 0 | 0 |
| 14 | — | 2 | 56 | 80 | 36 | 0 | 0 | 0 | 37 | 0 | 0 | 0 | 0 |
| 16 | — | 0 | 56 | 100 | 0 | 0 | 11 | 26 | 0 | 0 | 0 | 0 | 0 |
| 17 | — | 47 | 27 | 93 | 0 | 0 | 0 | 81 | 0 | 0 | 0 | 0 | 0 |
| 23 | 75 | 98 | 72 | 91 | 3 | 0 | 90 | 0 | 26 | 0 | 0 | 0 | 0 |
| 29 | 97 | 100 | 54 | 57 | 3 | 62 | 48 | 0 | 0 | 0 | 0 | 0 | 0 |
| 27 | 100 | 98 | 54 | 74 | 3 | 0 | 48 | 0 | 0 | 0 | 0 | 0 | 0 |
| 28 | 97 | 100 | 90 | 91 | 3 | 73 | 77 | 0 | 0 | 0 | 0 | 0 | 0 |
| 63 | 53 | 98 | 54 | 29 | 0 | 0 | 0 | 0 | 86 | 0 | 0 | 0 | 0 |
| 67 | 95 | 88 | 30 | 100 | 52 | 28 | 58 | 30 | 100 | 0 | 0 | 0 | 0 |
| 55 | 100 | 49 | 38 | 90 | 34 | 8 | 0 | 0 | 15 | 0 | 0 | 0 | 0 |
| 2 | 81 | 100 | 63 | 100 | 34 | 8 | 0 | — | 15 | 0 | 0 | 0 | 0 |
| 6 | 100 | 100 | 74 | 100 | 70 | 32 | 96 | 0 | 12 | 0 | 0 | 0 | 0 |
| 21 | 72 | 96 | 65 | 58 | 63 | 0 | 23 | 0 | 59 | 0 | 0 | 0 | 0 |
| 40 | 100 | 96 | 65 | 98 | 0 | 19 | 85 | 0 | 16 | 0 | 0 | 0 | 0 |
| 24 | 100 | 82 | 63 | 82 | 45 | 0 | 54 | 0 | 12 | 0 | 0 | 0 | 0 |
| 25 | 100 | 95 | 84 | 100 | 49 | 33 | 63 | 0 | 41 | 0 | 0 | 0 | 0 |
| 26 | 100 | 100 | 84 | 100 | 49 | 48 | 63 | 0 | 18 | 0 | 0 | 0 | 0 |
| 50 | 100 | 91 | 91 | 94 | 90 | 16 | 63 | 0 | 0 | 0 | 0 | 0 | 0 |
| 49 | 100 | 91 | 91 | 94 | 49 | 16 | 63 | 0 | 18 | 0 | 0 | 0 | 0 |
| 42 | 100 | 96 | 75 | 85 | 44 | 86 | 61 | 0 | 42 | 0 | 0 | 0 | 0 |
| 52 | 100 | 100 | 91 | 98 | 89 | 57 | 61 | 21 | 60 | 0 | 0 | 0 | 0 |
| 53 | 100 | 92 | 75 | 95 | 44 | 57 | 61 | 0 | 19 | 0 | 0 | 0 | 0 |
| 54 | 100 | 96 | 85 | 85 | 0 | 42 | 12 | 0 | 0 | 0 | 0 | 0 | 0 |
| 43 | 100 | 100 | 98 | 95 | 86 | 16 | 66 | 23 | 86 | 0 | 0 | 0 | 0 |
| 39 | 100 | 98 | 96 | 86 | 97 | 16 | 66 | 0 | 74 | 0 | 0 | 0 | 0 |
| 41 | 100 | 98 | 94 | 91 | 86 | 16 | 66 | 0 | 0 | 0 | 0 | 0 | 0 |
| 44 | 100 | 98 | 94 | 91 | 31 | 0 | 66 | 0 | 56 | 0 | 0 | 0 | 0 |
| 73 | 93 | 52 | 53 | 76 | 31 | 0 | 24 | 0 | 0 | 0 | 0 | 0 | 0 |
| 72 | 100 | 85 | 53 | 76 | 86 | 0 | 24 | 0 | 0 | 0 | 0 | 0 | 0 |
| 62 | 93 | 96 | 94 | 86 | 97 | 0 | 66 | 0 | 94 | 0 | 0 | 0 | 0 |
| 66 | 40 | 66 | 67 | 95 | 0 | 0 | 0 | 0 | 85 | 0 | 0 | 0 | 0 |
| 65 | 40 | 28 | 80 | 95 | 0 | 0 | 0 | 0 | 20 | 0 | 0 | 0 | 0 |
| 69 | 0 | 100 | 0 | 98 | 19 | 0 | 3 | 0 | 20 | 0 | 0 | 0 | 0 |
| 71 | 62 | 93 | 9 | 98 | 19 | 0 | 3 | 0 | 20 | 0 | 0 | 0 | 0 |
| 76 | 77 | 93 | 80 | 95 | 19 | 0 | 3 | 0 | 0 | 0 | 0 | 0 | 0 |
| 4 | 100 | 100 | 9 | 98 | 19 | 19 | 91 | 0 | 0 | 0 | 0 | 0 | 0 |
| 64 | 40 | 66 | 67 | 37 | 19 | 0 | 3 | 0 | 0 | 0 | 0 | 0 | 0 |
| 75 | 98 | 100 | 45 | 95 | 19 | 0 | 56 | 0 | 20 | 0 | 0 | 0 | 0 |
| 93 | 68 | 89 | 47 | 75 | 0 | 0 | 83 | 0 | 21 | 0 | 0 | 0 | 0 |
| 92 | 0 | 49 | 81 | 32 | 0 | 0 | 61 | 0 | 0 | 0 | 0 | 0 | 0 |
| 94 | 68 | 0 | 93 | 32 | 0 | 0 | 61 | 0 | 92 | 0 | 0 | 0 | 0 |
| 95 | 75 | 58 | 0 | 32 | 30 | 0 | 44 | 0 | 0 | 0 | 0 | 0 | 0 |
| 56 | 20 | 75 | 62 | 57 | 0 | 13 | 0 | 0 | 20 | 0 | 0 | 0 | 0 |
| 68 | 0 | 75 | 62 | 74 | 49 | 0 | 0 | 0 | 97 | 0 | 0 | 0 | 0 |
| 11 | 100 | 100 | 100 | 92 | 0 | 0 | 50 | 0 | 0 | 0 | 0 | 0 | 0 |
| 96 | 94 | 0 | 87 | 29 | 0 | 0 | 16 | 26 | 99 | 0 | 0 | 0 | 0 |
| 74 | 100 | 100 | 81 | 100 | 0 | 32 | 91 | 0 | 7 | 0 | 0 | 0 | 0 |
| 1 | 73 | 95 | 87 | 84 | 18 | 0 | 72 | 0 | 0 | 0 | 0 | 0 | 0 |
| 89 | 40 | 18 | 54 | 83 | 31 | 0 | 80 | 0 | 21 | 0 | 0 | 0 | 0 |
| 70 | 72 | 97 | 11 | 48 | 0 | 0 | 4 | 0 | 100 | 0 | 0 | 0 | 0 |
| 58 | 53 | 97 | 11 | 14 | 0 | 0 | 4 | 0 | 98 | 0 | 0 | 0 | 0 |
| 88 | 85 | 100 | 97 | 43 | 78 | 0 | 63 | 0 | 21 | 0 | 0 | 0 | 0 |
| 86 | 85 | 100 | 85 | 79 | 50 | 0 | 93 | 0 | 0 | 0 | 0 | 0 | 0 |
| 20 | 100 | 100 | 97 | 43 | 0 | 0 | 18 | 0 | 79 | 0 | 70 | 0 | 0 |

TABLE VI-continued

PLANT DISEASE CONTROL DATA

| Cmpd No. | EX. 22 | EX. 23 | EX. 24 | EX. 25 | EX. 26 | EX. 27 | EX. 28 | EX. 29 | EX. 30 | EX. 31 | EX. 32 | EX. 33 | EX. 34 |
|---|---|---|---|---|---|---|---|---|---|---|---|---|---|
| 22 | 100 | 100 | 91 | 95 | 78 | 0 | 100 | 0 | 65 | 0 | 0 | 60 | 0 |
| 79 | 72 | 67 | 32 | 79 | 50 | 0 | 63 | 0 | 65 | 0 | 60 | 80 | 0 |
| 78 | 98 | 100 | 85 | 92 | 0 | 0 | 18 | 0 | 79 | 0 | 0 | 0 | 0 |
| 85 | 85 | 97 | 93 | 81 | 0 | 0 | 57 | 0 | 0 | 0 | 0 | 0 | 0 |
| 87 | 98 | 100 | 96 | 96 | 0 | 33 | 89 | 0 | 49 | 0 | 0 | 0 | 0 |
| 84 | 100 | 100 | 89 | 100 | 52 | 33 | 89 | 0 | 49 | 0 | 0 | 0 | 0 |
| 80 | 94 | 93 | 66 | 97 | 0 | 0 | 0 | 0 | 0 | 0 | 0 | 0 | 0 |
| 81 | 100 | 100 | 88 | 100 | 0 | 0 | 0 | 0 | 22 | 0 | 0 | 0 | 0 |
| 82 | 100 | 100 | 0 | 50 | 0 | 0 | 0 | 0 | 21 | 0 | 0 | 0 | 0 |
| 83 | 100 | 95 | 0 | 50 | 0 | 0 | 0 | 0 | 21 | 0 | 0 | 0 | 0 |
| 77 | 71 | 100 | 74 | 100 | 28 | 18 | 86 | 0 | 33 | 0 | 0 | 0 | 0 |
| 60 | 83 | 97 | 86 | 100 | 61 | 35 | 29 | 0 | 16 | 0 | 70 | 0 | 0 |
| 59 | 17 | 93 | 78 | 85 | 46 | 18 | 29 | 0 | 59 | 0 | 0 | 0 | 0 |
| 18 | 68 | 97 | 78 | 100 | 0 | 0 | 29 | 0 | 16 | 0 | 0 | 0 | 0 |
| 31 | 83 | 84 | 92 | 31 | 46 | 0 | 0 | 0 | 84 | 0 | 0 | 0 | 0 |
| 34 | 83 | 97 | 86 | 98 | 46 | 0 | 0 | 0 | 16 | 100 | 0 | 0 | 0 |
| 35 | 83 | 84 | 86 | 98 | 46 | 0 | 0 | 0 | 0 | 0 | 0 | 0 | 0 |
| 38 | 68 | 97 | 78 | 94 | 46 | 0 | 29 | 0 | 0 | 0 | 0 | 0 | 0 |
| 36 | 68 | 7 | 71 | 92 | 44 | 0 | 7 | 0 | 0 | 0 | 0 | 0 | 0 |
| 37 | 100 | 91 | 71 | 77 | 0 | 0 | 58 | 0 | 0 | 0 | 0 | 0 | 0 |
| 19 | 100 | 100 | 82 | 92 | 0 | 0 | 58 | 0 | 45 | 0 | 0 | 0 | 0 |
| 61 | 100 | 100 | 71 | 86 | 0 | 0 | 58 | 0 | 0 | 0 | 60 | 0 | 0 |
| 57 | 68 | 81 | 82 | 77 | 0 | 0 | 58 | 0 | 0 | 0 | 0 | 0 | 0 |
| 48 | 100 | 100 | 82 | 95 | 0 | 0 | 81 | 0 | 0 | 0 | 0 | 0 | 0 |
| 7 | 100 | 100 | 94 | 100 | 0 | 0 | 58 | 0 | 0 | 0 | 0 | 60 | 0 |
| 32 | 83 | 91 | 96 | 61 | 0 | 0 | 7 | 0 | 0 | 0 | 0 | 0 | 0 |
| 33 | 98 | 100 | 20 | 92 | 0 | 0 | 7 | 0 | 0 | 0 | 0 | 0 | 0 |
| 47 | 100 | 100 | 82 | 95 | 0 | 0 | 58 | 0 | 0 | 0 | 0 | 0 | 0 |
| 51 | 100 | 100 | 89 | 100 | 0 | 0 | 58 | 0 | 0 | 0 | 0 | 0 | 0 |
| 3 | 0 | 50 | 0 | — | 0 | 0 | 0 | 0 | — | 6 | 0 | 0 | 6 |
| 97 | 91 | 98 | 81 | 92 | 42 | 62 | 91 | 23 | 62 | 0 | 0 | 0 | 0 |
| 98 | 100 | 60 | 91 | 96 | 0 | 71 | 0 | 25 | 33 | 0 | 0 | 0 | 0 |
| 99 | 53 | 98 | 91 | 97 | 63 | 0 | 36 | 0 | 52 | 0 | 0 | 0 | 0 |

What is claimed:

1. A compound of the general formula:

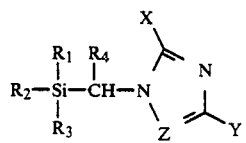

wherein $R_1$ is

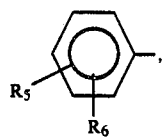

naphthyl, $-CR_7=CHR_8$, or $-C\equiv CR_7$:

$R_2$ and $R_3$ are independently $C_1-C_6$ alkyl, vinyl, $CH_2CR_9=CR_{10}R_{11}$,

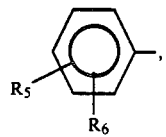

or $OR_{12}$ provided that both $R_2$ and $R_3$ may not be $OR_{12}$:

$R_4$ is H or $CH_3$:

$R_5$ and $R_6$ are independently H, F, Cl, Br, $OCH_3$, $SCH_3$, $OCF_2H$, $OCF_3$, $C_1-C_4$ alkyl, $C_1-C_4$ haloalkyl, phenyl, or halophenyl:

$R_7$ and $R_8$ are independently H, $C_1-C_4$ alkyl, or

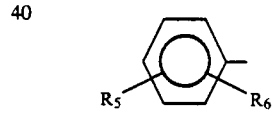

$R_9$, $R_{10}$ and $R_{11}$ are independently H or $CH_3$;

Z is N or CH;

when Z is N,

X is H, $C_2-C_4$ alkenyl, ethynyl, F, Cl, Br, I, $NO_2$, SH and its corresponding disulfide, SeH and its corresponding diselenide,

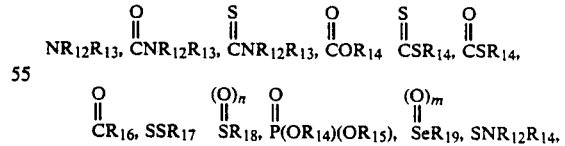

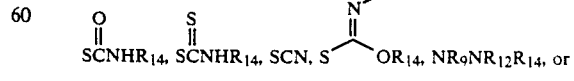

$$\overset{OH}{\underset{|}{CHR_{16}}};$$

Y is H, F, Cl, Br, I,

SSR$_{17}$, CO$_2$CH$_3$, CHO, or SH and its corresponding disulfide;
m is 0 or 1;
n is 0, 1, or 2;
R$_{12}$ is H or C$_1$-C$_4$ alkyl;
R$_{13}$ is H, C$_1$-C$_4$ alkyl, allyl, benzyl, C$_1$-C$_4$ alkylcarbonyl, C$_1$-C$_4$ haloalkylcarbonyl;
R$_{14}$ and R$_{15}$ are independently H, C$_1$-C$_4$ alkyl, allyl, benzyl, or phenyl optionally substituted with 1-3 substituents independently selected from halogen, C$_1$-C$_4$ alkyl, C$_1$-C$_4$ haloalkyl, C$_1$-C$_4$ alkoxy, NO$_2$ or SCH$_3$;
R$_{16}$ is H, C$_1$-C$_8$ alkyl, C$_3$-C$_8$ cycloalkyl, C$_2$-C$_8$ alkenyl, C$_4$-C$_8$ cycloalkenyl, alpha-pinenyl, aralkyl, aralkenyl, or phenyl optionally substituted with 1-3 substituents independently selected from halogen, C$_1$-C$_4$ alkyl, C$_1$-C$_4$ haloalkyl, C$_1$-C$_4$ alkoxy, NO$_2$ or SCH$_3$;
R$_{17}$ is C$_1$-C$_4$ alkyl, C$_1$-C$_4$ haloalkyl, allyl, benzyl or phenyl optionally substituted with 1-3 substituents independently selected from halogen, C$_1$-C$_4$ alkyl, C$_1$-C$_4$ haloalkyl, C$_1$-C$_4$ alkoxy, NO$_2$ or SCH$_3$;
R$_{18}$ is C$_1$-C$_5$ alkyl, C$_1$-C$_4$ haloalkyl, CH$_2$SCN, C$_2$-C$_4$ alkenyl, CHR$_9$(CHR$_{10}$)$_m$CN, CH$_2$CO$_2$R$_{14}$, C$_3$-C$_4$ alkynyl, CH$_2$NO$_2$, benzyl, CH$_2$OCH$_3$,

R$_{19}$ is CH$_3$, phenyl, or benzyl;
R$_{20}$ is C$_1$-C$_4$ alkyl, CH$_2$CN, CH$_2$SCN, or allyl;
provided that either X or Y must be H but both X and Y cannot be H simultaneously;
when Z is CH, Y is H and X is S(O)$_n$R$_{21}$, SO$_2$OH, I or SH and its corresponding disulfide;
R$_{21}$ is C$_2$-C$_4$ alkyl, CH$_2$CN or CH$_2$SCN.

2. The compound of claim 1 wherein

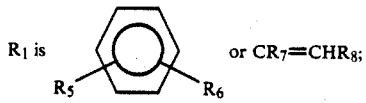

R$_5$ and R$_6$ are independently H, F, Cl, Br, phenyl, or halophenyl;
R$_2$ is C$_1$-C$_4$ alkyl or

R$_3$ is C$_1$-C$_4$ alkyl, vinyl, allyl, or OR$_{12}$; R$_4$ is H; X is F, Cl, I,

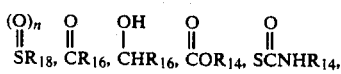

SSR$_{17}$, or SH and its corresponding disulfide; and Y is H.

3. The compound of claim 2 wherein
R$_3$ is C$_1$-C$_4$ alkyl, allyl, or OR$_{12}$;
R$_5$ and R$_6$ are independently H, F, Cl, Br, phenyl, or halophenyl substituted at the 4-position; and
X is I,

SSR$_{17}$, or SH and its corresponding disulfide.

4. The compound of claim 3 wherein
X is I,

SSR$_{17}$, or SH and its corresponding disulfide.

5. The compound of claim 1 which is 1-[bis(4-fluorophenyl)(methyl)silylmethyl]-1H-1,2,4-triazole-5-thiol.

6. The compound of claim 1 which is 1-[bis(4-fluorophenyl)(methyl)silylmethyl]-5-iodo-1H-1,2,4-triazole.

7. The compound of claim 1 which is 1-[bis(4-fluorophenyl)(methyl)silylmethyl]-5-(cyanomethylsulfonyl)-1H-1,2,4-triazole.

8. The compound of claim 1 which is 1-[bis(4-fluorophenyl)(methyl)silylmethyl]-2-iodo-1H-imidazole.

9. A composition for controlling fungus disease which comprises an effective amount of a compound of claim 1 and at least one of the following: surfactant, solid or liquid inert diluent.

10. A composition for controlling fungus disease which comprises an effective amount of a compound of claim 2 and at least one of the following: surfactant, solid or liquid inert diluent.

11. A composition for controlling fungus disease which comprises an effective amount of a compound of claim 3 and at least one of the following: surfactant, solid or liquid inert diluent.

12. A composition for controlling fungus disease which comprises an effective amount of a compound of claim 4 and at least one of the following; surfactant, solid or liquid inert diluent.

13. A composition for controlling fungus disease which comprises an effective amount of a compound of claim 5 and at least one of the following: surfactant, solid or liquid inert diluent.

14. A composition for controlling fungus disease which comprises an effective amount of a compound of claim 6 and at least one of the following: surfactant, solid or liquid inert diluent.

15. A composition for controlling fungus disease which comprises an effective amount of a compound of claim 7 and at least one of the following: surfactant, solid or liquid inert diluent.

16. A composition for controlling fungus disease which comprises an effective amount of a compound of claim 8 and at least one of the following: surfactant, solid or liquid inert diluent.

17. A method for controlling fungus disease which comprises applying to the locus of infestation to be protected an effective amount of a compound of claim 1.

18. A method for controlling fungus disease which comprises applying to the locus of infestation to be protected an effective amount of a compound of claim 2.

19. A method for controlling fungus disease which comprises applying to the locus of infestation to be protected an effective amount of a compound of claim 3.

20. A method for controlling fungus disease which comprises applying to the locus of infestation to be protected an effective amount of a compound of claim 4.

21. A method for controlling fungus disease which comprises applying to the locus of infestation to be protected an effective amount of a compound of claim 5.

22. A method for controlling fungus disease which comprises applying to the locus of infestation to be protected an effective amount of a compound of claim 6.

23. A method for controlling fungus disease which comprises applying to the locus of infestation to be protected an effective amount of a compound of claim 7.

24. A method for controlling fungus disease which comprises applying to the locus of infestation to be protected an effective amount of a compound of claim 8.

* * * * *